United States Patent
Andjouh et al.

(10) Patent No.: US 10,487,071 B2
(45) Date of Patent: Nov. 26, 2019

(54) BIS-TRIAZOLE COMPOUNDS WITH ANTI-BIOFILM AND ANTI-CORROSION PROPERTIES

(71) Applicant: Université de Toulon, La Garde (FR)

(72) Inventors: Sofyane Andjouh, Toulon (FR); Francois-Xavier Perrin, La Farlede (FR); Yves Guy Blache, Gareoult (FR)

(73) Assignee: Universite de Toulon, La Garde (FR)

( * ) Notice: Subject to any disclaimer, the term of this patent is extended or adjusted under 35 U.S.C. 154(b) by 0 days.

(21) Appl. No.: 16/061,767

(22) PCT Filed: Dec. 14, 2016

(86) PCT No.: PCT/EP2016/081068
§ 371 (c)(1),
(2) Date: Jun. 13, 2018

(87) PCT Pub. No.: WO2017/102883
PCT Pub. Date: Jun. 22, 2017

(65) Prior Publication Data
US 2018/0370953 A1    Dec. 27, 2018

(30) Foreign Application Priority Data

Dec. 14, 2015   (WO) .................. PCT/IB2015/002582

(51) Int. Cl.
| | | |
|---|---|---|
| *C07D 403/10* | (2006.01) | |
| *C07D 403/06* | (2006.01) | |
| *C07D 403/12* | (2006.01) | |
| *C07D 249/06* | (2006.01) | |
| *A01N 43/647* | (2006.01) | |
| *C23F 11/14* | (2006.01) | |

(52) U.S. Cl.
CPC ......... *C07D 403/10* (2013.01); *A01N 43/647* (2013.01); *C07D 249/06* (2013.01); *C07D 403/06* (2013.01); *C07D 403/12* (2013.01); *C23F 11/149* (2013.01)

(58) Field of Classification Search
CPC .. C07D 403/10; C07D 249/06; C07D 403/06; C07D 403/12; A01N 43/647
See application file for complete search history.

(56) References Cited

FOREIGN PATENT DOCUMENTS

CN    104725393 A    6/2015

OTHER PUBLICATIONS

El Malah et al.,Nanoscale,2012,4,467-472.*
Hirsch et al. The Journal of Chemical Physics, 142, 2015, pp. 101914-101914-12.*
Schulze et al., Dalton Trans. 2009, pp. 787-794.*
Ozkal et al., Adv. Synth. Catal., 2014, 356, pp. 857-869.*
Synøve et al., "Self-assembled palladium(II) "click" cages: synthesis, structural modification and stability," Dalton Transactions: The International Journal of Inorganic, Organometallic and Bioinorganic Chemistry, 40: 12117-12124 (2011).
Camps et al., "Antifouling activity of commercial biocides vs. natural and natural-derived products assessed by marine bacteria adhesion bioassay," Marine Pollution Bulletin, 62: 1032-1040 (2011).
International Search Report issued in corresponding International Patent Application No. PCT/EP2016/081068 dated Feb. 15, 2017.
Written Opinion issued in corresponding International Patent Application No. PCT/EP2016/081068 dated Feb. 15, 2017.

* cited by examiner

*Primary Examiner* — Rebecca L Anderson
(74) *Attorney, Agent, or Firm* — Morgan, Lewis & Bockius LLP

(57) ABSTRACT

The present invention deals with novel bis-triazole compounds, compositions comprising these compounds, and their uses as a medicament, an antibacterial agent, an anti-biofilm agent, an anti-fouling agent and/or an anti-corrosion agent.

12 Claims, 2 Drawing Sheets

BIS-TRIAZOLE COMPOUNDS WITH ANTI-BIOFILM AND ANTI-CORROSION PROPERTIES

TECHNICAL FIELD

The present invention deals with novel bis-triazole compounds, compositions comprising said compounds, and their uses as a medicament, an antibacterial agent, an anti-biofilm agent, an anti-fouling agent and/or an anti-corrosion agent.

BACKGROUND

Over the past few years, biofilms have become a major concern in many different industries such as food-processing, maritime transport, aquaculture, offshore drilling but also in the domestic and medical environment.

Biofilm formation is a process comprising three different steps. The first step consists in the attachment of mobile microorganisms, such as bacteria and microalgae, on a surface. In the second step, the microorganisms produce polysaccharides which consolidate the interface between the microorganisms and the surface. The final step leading to a biofilm involves colonization, growth and division of the microorganisms on the surface. A fully developed biofilm will contain an exopolymeric matrix and mushroom-shaped structures separated by interstitial spaces. Biofilms have a heterogeneous structure and are capable of mass internal transport.

In a marine environment, biofilms are subsequently colonized with macrofoulers, such as macroalgae and invertebrates. Marine biofouling is an invasive phenomenon causing significant problems on immerged marine structures used in the shipping, aquaculture and offshore petroleum industry, such as an increase in weight, fuel consumption and frictional drag.

Conventionally, metal-based paints have been used to control development, maturation, and growth of biofouling processes. Organotin-based paints have especially been used due to their biocide properties and their efficiency to prevent marine fouling. Unfortunately, organotin coatings were found to adversely affect the environment due to the collateral damage inflicted on the marine ecosystem and non-target species. Organotins are now banned from use by the International Maritime Organisation (IMO) and there is thus a need for non-toxic compounds that can effectively prevent biofilm formation.

After extensive research, Applicant has found that bis-triazole compounds of general formula (I) exhibit excellent anti-biofilm activities. Surprisingly, these compounds also exhibit excellent anticorrosion properties. Since corrosion is another problem frequently encountered in immerged marine structures, the compounds of the present invention can advantageously be used to simultaneously protect said structures from fouling and corrosion.

SUMMARY OF THE INVENTION

A first object of the present invention is thus a compound of general formula (I):

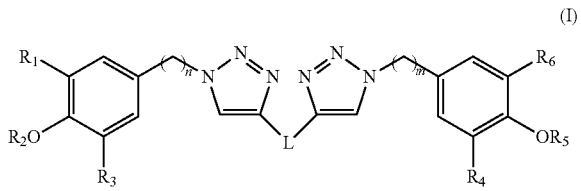

wherein L, $R_1$, $R_2$, $R_3$, $R_4$, $R_5$, $R_6$, n and m are as defined herein;

and salts thereof.

Another object of the present invention is a compound of general formula (I) as defined herein for use as a medicament.

Another object of the present invention is a composition comprising a compound of general formula (I) and a carrier.

Yet another object of the present invention is the non-therapeutic use of a compound of general formula (I) as an antibacterial agent.

Yet another object of the present invention is the non-therapeutic use of a compound of general formula (I) as an anti-biofilm agent.

Yet another object of the present invention is the non-therapeutic use of a compound of general formula (I) as an anti-fouling agent.

Yet another object of the present invention is the non-therapeutic use of a compound of general formula (I) as an anti-corrosion agent.

DEFINITIONS

The term "alkyl" means any monovalent radical of a linear or branched hydrocarbon chain comprising 1 to 18 carbon atoms. The expression "$C_1$-$C_6$ alkyl" represents an alkyl having 1 to 6 carbon atoms. Examples of $C_1$-$C_6$ alkyl groups include methyl, ethyl, n-propyl, i-propyl, n-butyl, i-butyl, s-butyl or t-butyl, n-pentyl, n-hexyl.

The term "alkanediyl" means any divalent radical of a linear or branched hydrocarbon chain comprising 1 to 18 carbon atoms.

The expression "arylene" represents any divalent radical of an aromatic hydrocarbon comprising 6 to 18 carbon atoms. Examples of $C_6$-$C_{18}$ arylene groups include phenylene and naphthylene, phenanthrylene.

The expression "heteroarylene" represents any divalent radical of a monocyclic or bicyclic 5 to 10 membered aromatic group comprising from 1 to 3 heteroatoms independently selected from oxygen, nitrogen and sulfur. Examples of $C_5$-$C_{10}$ heteroaryl groups include furyl, thienyl, pyrrolyl, pyrazoyl, imidazolyl, isoxazolyl, isothiazoyl, thiazolyl, oxazolyl, 1,2,3-triazolyl, 1,2,4-triazolyl, 1-benzofuryl, 1-benzothienyl, indolyl, benzimidazolyl, indazolyl, 1,2-benzisoxazolyl, 2,1-benzisoxazolyl, 1,2-benzisothiazolyl, 2,1-benzisothiazolyl, benzothiazolyl, benzoxazolyl, benzotriazolyl, pyridyl, pyridinium, quinolinyl, isoquinolinyl, pyridazinyl, cinnolinyl, phthalazinyl, pyrimidinyl, quinazolinyl, pyrazinyl and quinoxalinyl.

Unless mentioned otherwise, the groups and radicals defined hereinabove may be unsubstituted or substituted by one or more substituents such as, for example, halogen, alkyl, alkoxy, aryl, heteroaryl, haloalkyl, haloalkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino.

DETAILED DESCRIPTION OF THE INVENTION

Compounds of General Formula (I)

Compounds of the present invention correspond to compounds of general formula (I):

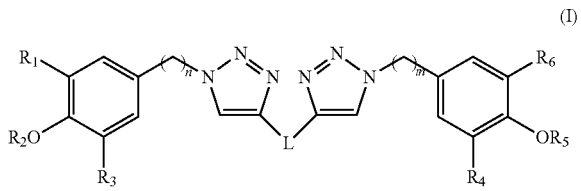

wherein
L is selected from a substituted or unsubstituted alkanediyl radical, —$(CR_aR_b)_p$—X—$(CR_aR_b)_q$— or a substituted or unsubstituted arylene or heteroarylene directly branched with the triazole groups;
$R_1$, $R_3$, $R_4$ and $R_6$ are independently selected from H, Br, Cl, I and F;
$R_2$ and $R_5$ are independently selected from H or a substituted or unsubstituted alkyl;
X is selected from O, NR', S or S=O;
R', $R_a$ and $R_b$ are independently H or $(C_1$-$C_6)$alkyl;
n and m are independently 0, 1, 2, 3 or 4;
p and q are independently 1, 2 or 3;
and salts thereof;
with the proviso that said compound is not

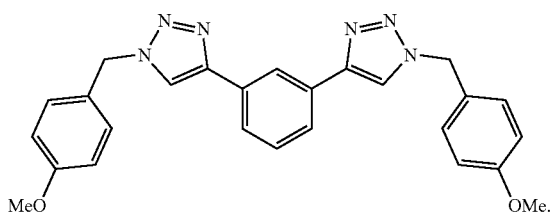 [SMILES: COc1ccc(Cn2cc(-c3cccc(-c4cn(Cc5ccc(OC)cc5)nn4)c3)nn2)cc1]

The linker L of the compound of general formula (I) may be selected from a substituted or unsubstituted alkanediyl radical. In particular, L may be selected from a substituted or unsubstituted alkanediyl radical having 1 to 10 carbon atoms, more particularly 2 to 8 carbon atoms, even more particularly 3 to 6 carbon atoms.

The linker L may also be selected from —$(CR_aR_b)_p$—X—$(CR_aR_b)_q$— wherein:
X is selected from O, NR', S or S=O;
R', $R_a$ and $R_b$ are independently H or $(C_1$-$C_6)$alkyl; and
p and q are independently 1, 2 or 3.

In particular, L may be selected from —$(CH_2)_p$—O—$(CH_2)_q$— or —$(CH_2)_p$—NH—$(CH_2)_q$— and p and q are independently 1 or 2. More particularly, L may be selected from —$CH_2$—O—$CH_2$— and —$CH_2$—NH—$CH_2$—.

The linker L may further be selected from a substituted or unsubstituted arylene or heteroarylene directly branched with the triazole groups. The term "directly branched with the triazole groups" means that the substituted or unsubstituted arylene or heteroarylene is connected to the triazole groups by means of a bond, i.e. there is no other atom intercalated between the arylene or heteroarylene and the triazole groups. More particularly, L may be a substituted or unsubstituted phenylene, preferably an unsubstituted phenylene directly branched in positions 1,3 or 1,4 with the triazole groups.

According to one embodiment, the linker L may be as defined above and $R_1$, $R_3$, $R_4$ are $R_6$ are independently selected from H, Br, Cl, I and F. In particular, $R_1$, $R_3$, $R_4$ and $R_6$ may all be H or may all be Br. Alternatively, at least one of $R_1$ and $R_3$ is Br, Cl or I and at least one of $R_4$ and $R_6$ is Br, Cl or I, more particularly, one of $R_1$ and $R_3$ is H and the other is Br, Cl or I and one of $R_4$ and $R_6$ is H and the other is Br, Cl or I.

According to another embodiment, L, $R_1$, $R_3$, $R_4$ are $R_6$ are as defined above and $R_2$ and $R_5$ are independently selected from H or a substituted or unsubstituted alkyl. In particular, $R_2$ and $R_5$ are independently selected from H, unsubstituted $(C_1$-$C_6)$alkyl, and $(C_1$-$C_6)$alkyl substituted by at least one group selected from amino, $(C_1$-$C_6)$alkylamino, (di$(C_1$-$C_6)$alkyl)amino group or an ammonium salt thereof. More particularly $R_2$ and $R_5$ are independently selected from H, methyl, methyl(dimethylamino), ethyl(dimethylamino), propyl(dimethylamino), the trifluoroacetate ammonium salt of ethyl(dimethylamino) or the trifluoroacetate ammonium salt of propyl(dimethylamino).

According to yet another embodiment, L, $R_1$, $R_2$, $R_3$, $R_4$, $R_5$ and $R_6$ are as defined above and n and m are independently 0, 1, 2, 3 or 4. In particular, n and m are independently 0, 1, 2 or 3. More particularly, n and m are 2.

Also encompassed in the compounds of the present invention are the salts of compounds of general formula (I). Examples of suitable salts include non-toxic acid addition salts and base salts. For example, the acid addition salt may be selected from hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate, and pamoate. Suitable base salts include sodium, potassium, calcium, magnesium, ammonium, N-methylglucamine, alkanolammonium, and salts of organic amines.

In a preferred embodiment, the compounds of the present invention correspond to general formula (I) wherein L, $R_1$, $R_2$, $R_3$, $R_4$, $R_5$, $R_6$ n and m are as defined above and wherein:
$R_1$ and $R_6$ are identical;
$R_2$ and $R_5$ are identical;
$R_3$ and $R_4$ are identical; and
n and m are identical.

Indeed, the synthesis of such compounds is easy and convergent.

In a preferred embodiment, the compounds of the present invention correspond to general formula (I) wherein:
L is selected from a substituted or unsubstituted alkanediyl radical having 3 to 6 carbon atoms, $CH_2$—O—$CH_2$—, —$CH_2$—NH—$CH_2$; or a substituted or unsubstituted phenylene directly branched with the triazole groups;
$R_1$, $R_3$, $R_4$ and $R_6$ are independently selected from H, Br, Cl and I;
$R_2$ and $R_5$ are independently selected from H, unsubstituted $(C_1$-$C_6)$alkyl, and $(C_1$-$C_6)$alkyl substituted by a (di$(C_1$-$C_6)$alkyl)amino group or an ammonium salt thereof;
n and m are 0, 1, 2 or 3.

In a particularly preferred embodiment, the compounds of the present invention correspond to one of the following formulae:

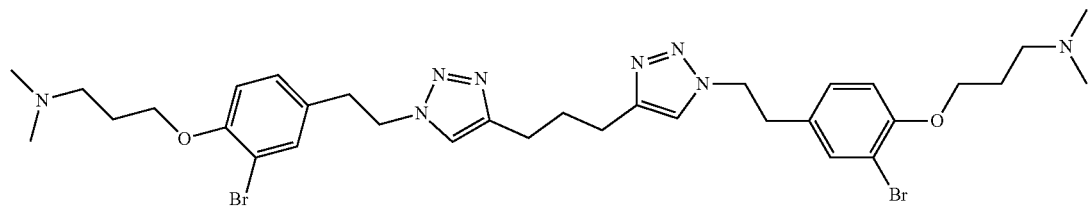
AS168
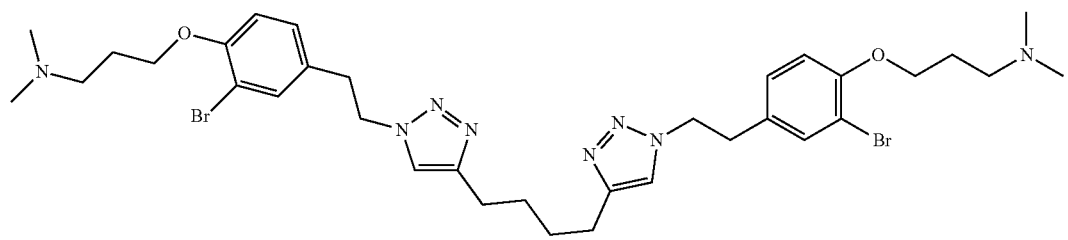
AS169
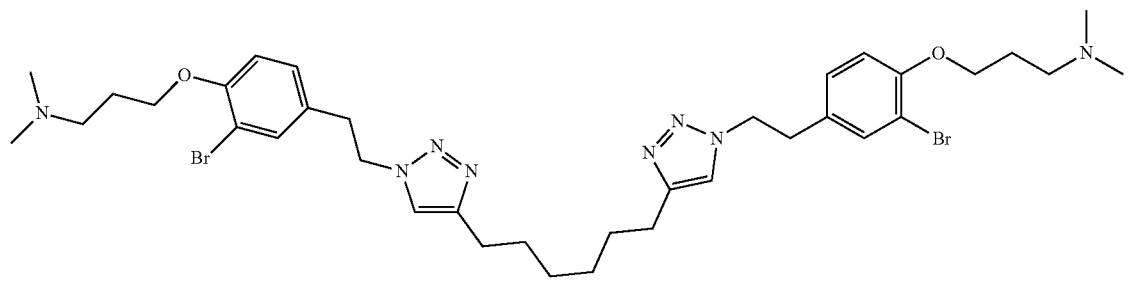
AS170
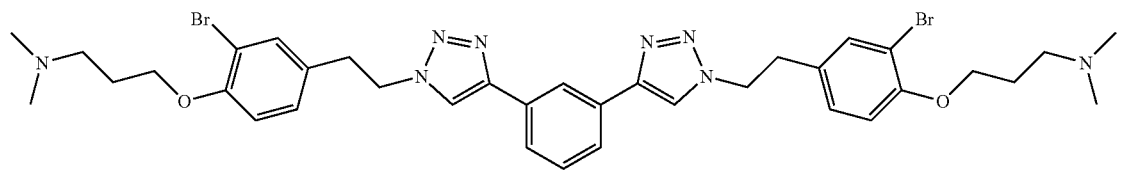
AS171
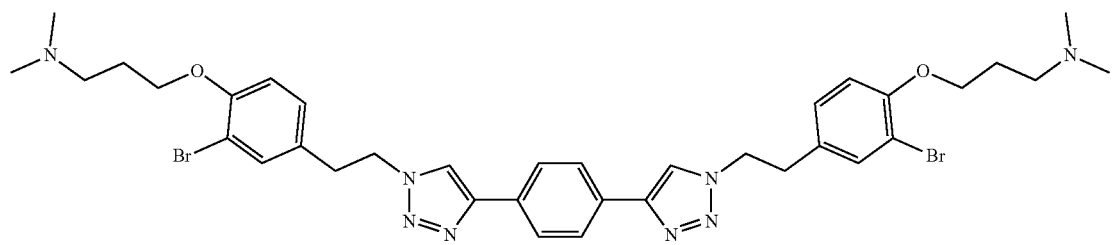
AS172
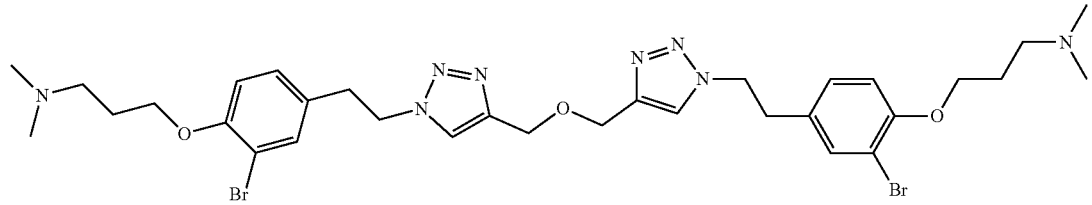
AS173
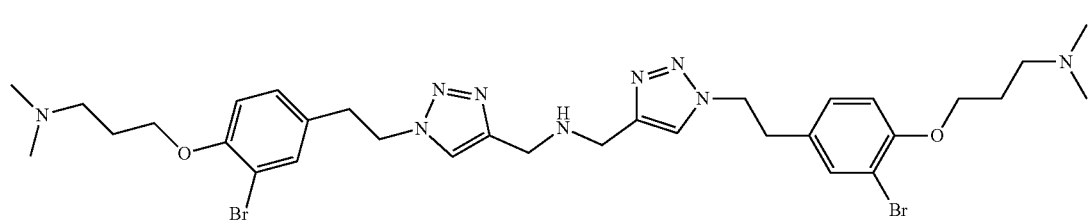
AS174

-continued
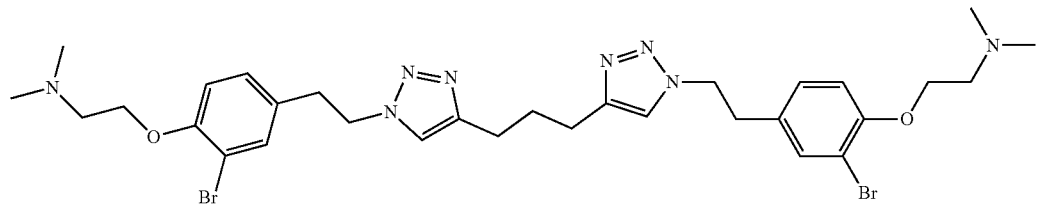
AS158
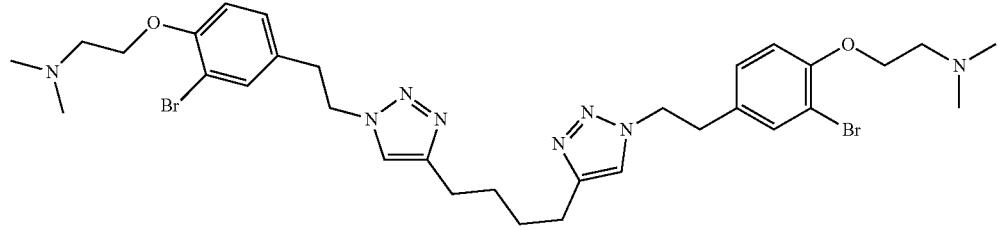
AS159
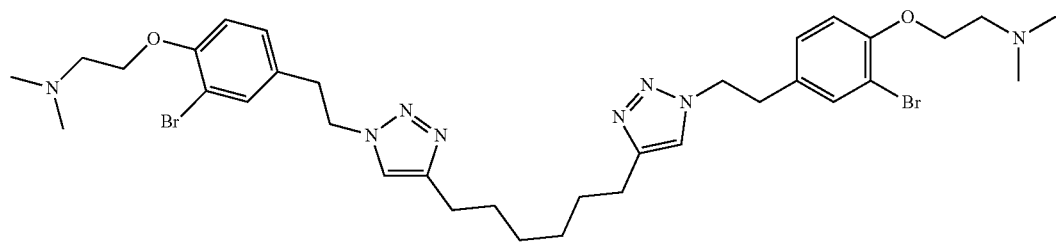
AS160
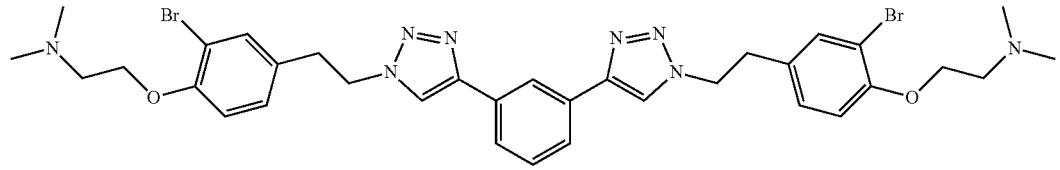
AS161
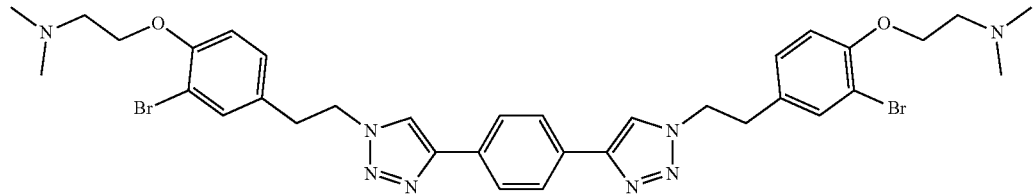
AS162
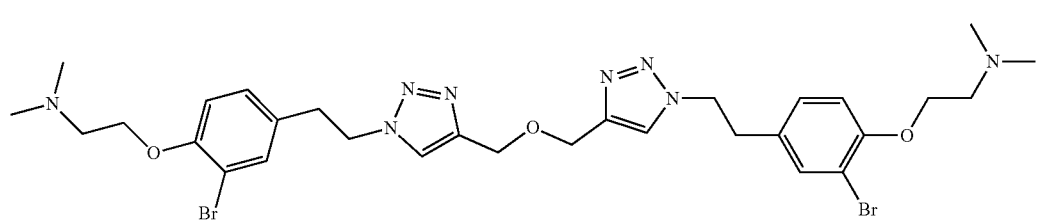
AS163
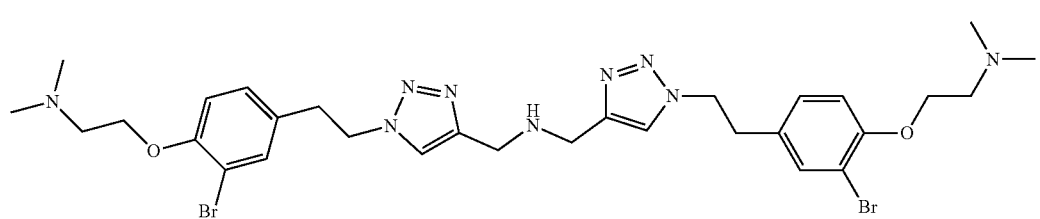
AS164

-continued
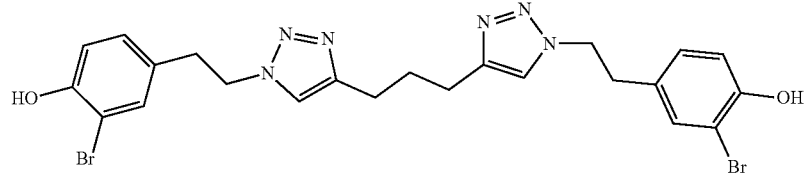
NT21
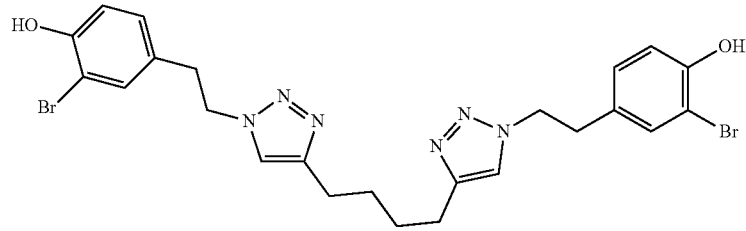
NT22
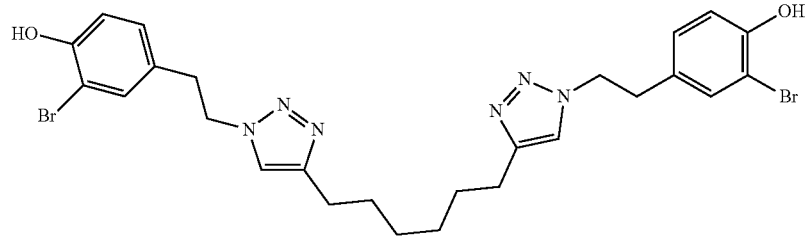
NT25
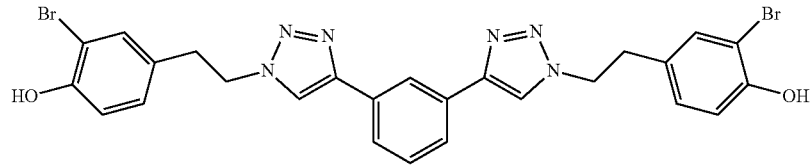
NT24
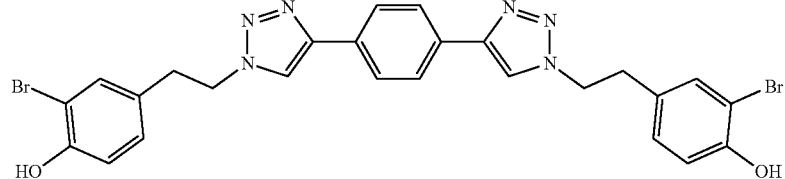
NT23
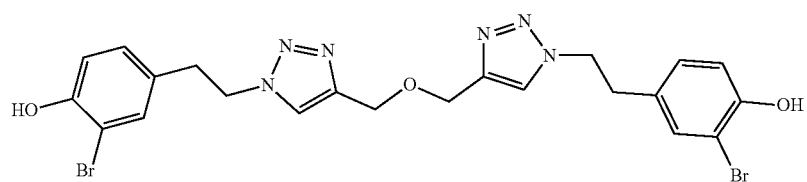
NT26
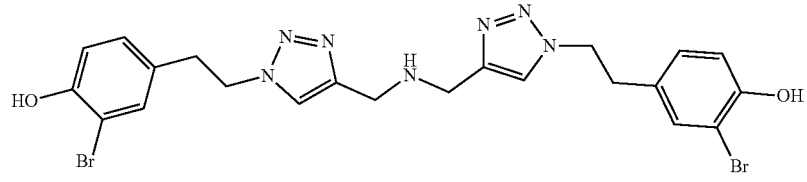
NT27
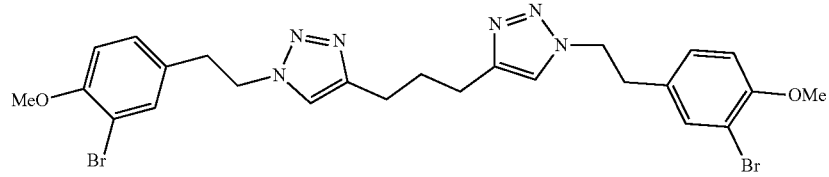
NT10

-continued
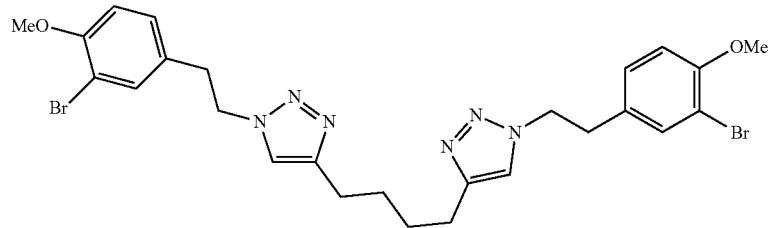
NT3
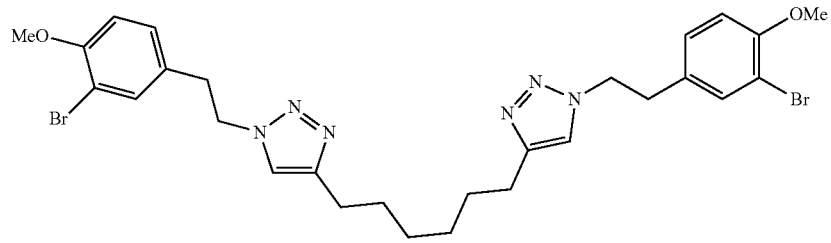
NT4
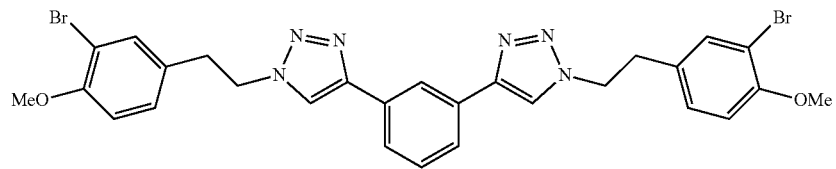
NT5
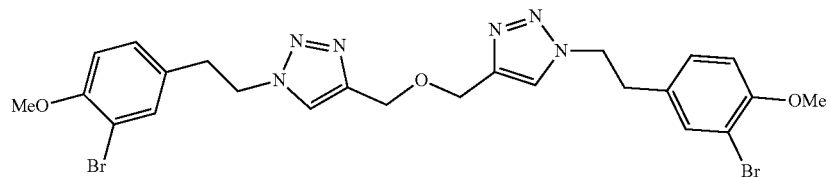
NT6
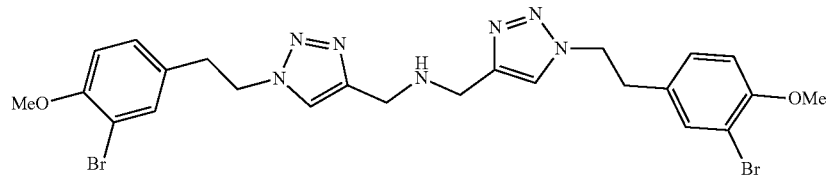
NT7
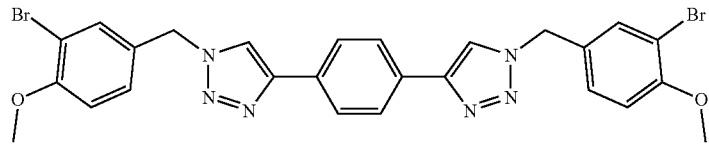
SA8
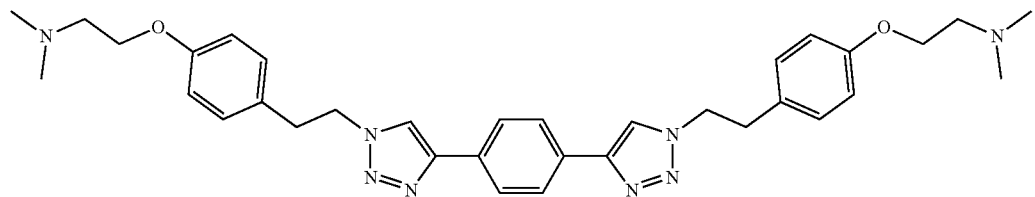
SA11

-continued
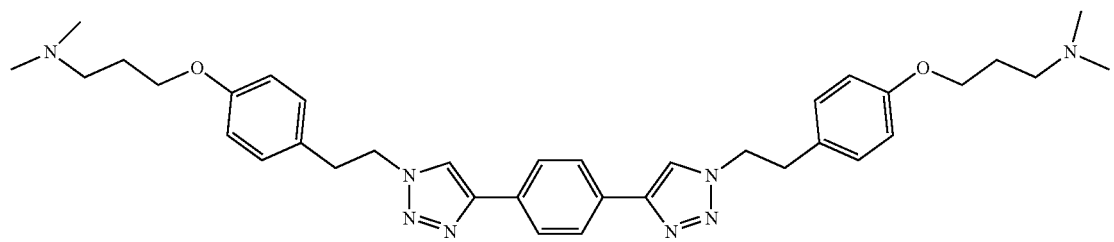
SA12
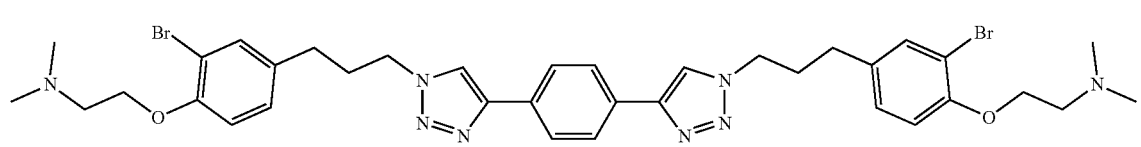
SA31
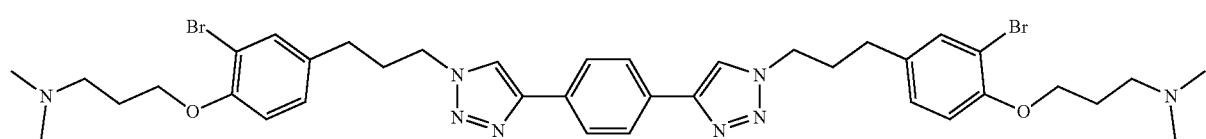
SA32
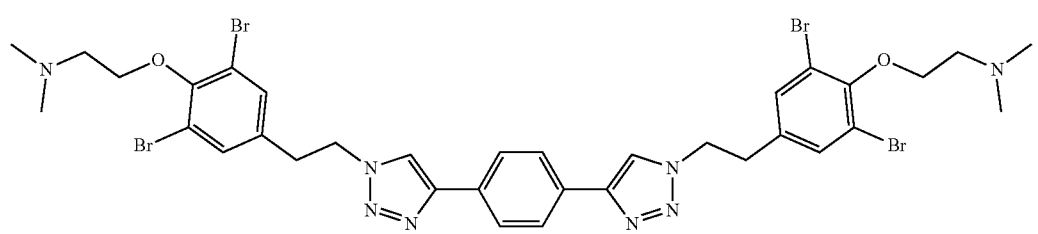
SA33
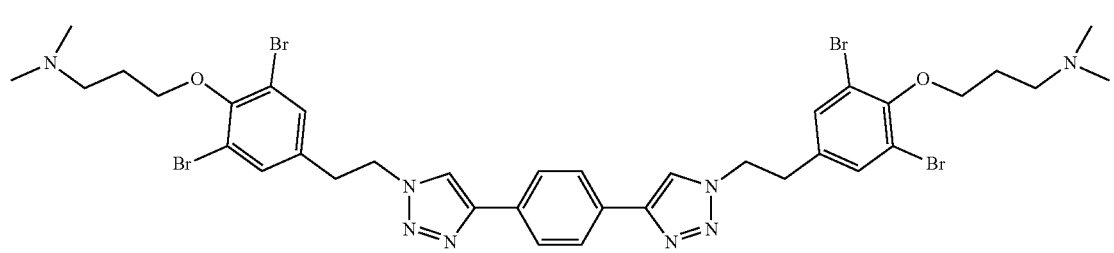
SA34
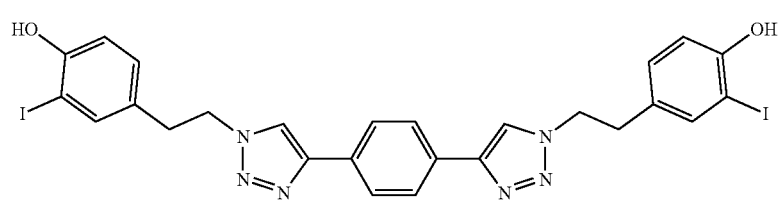
SA43
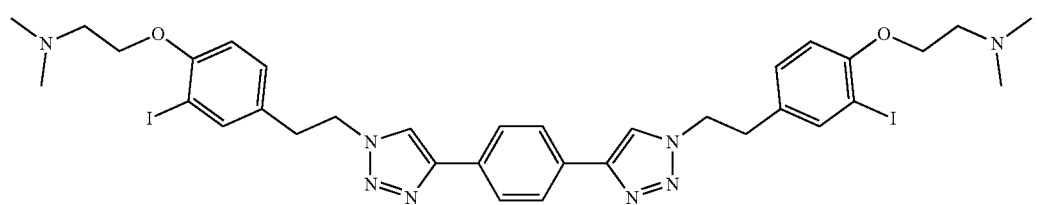
SA45

SA46
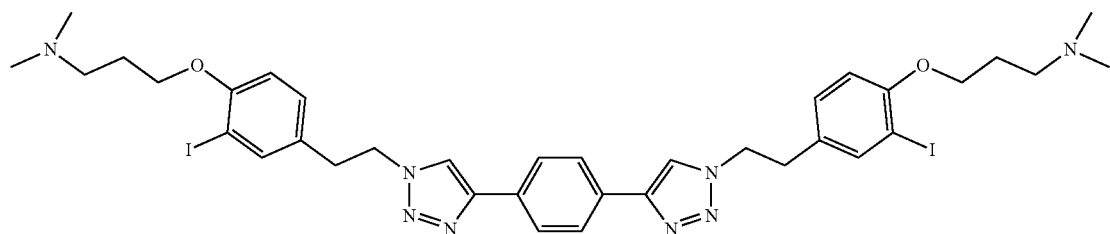
SA61
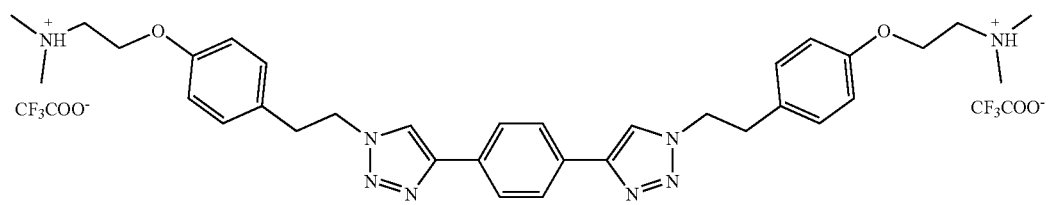
SA63
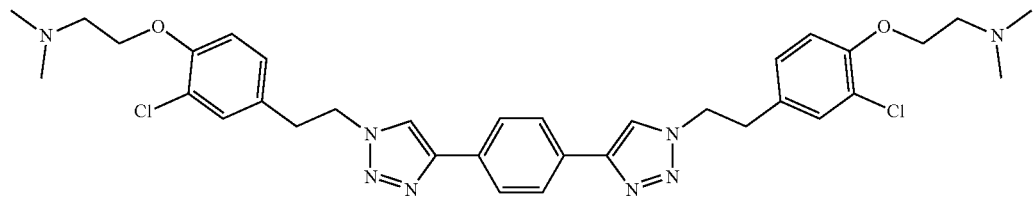
SA64
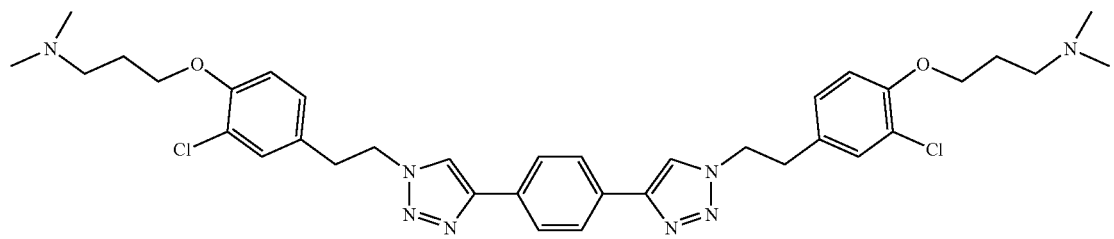
SA66
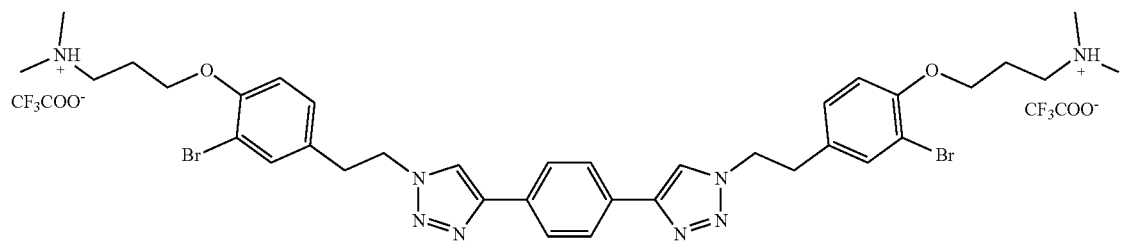
Compounds of general formula (I) may be prepared according to various methods well known in the art. For example, said compounds may be obtained in an easy and convergent manner from a dialkyne and two azides using a copper(I)-catalyzed Azide-Alkyne Cycloaddition (CuAAC) according to the following synthetic route:
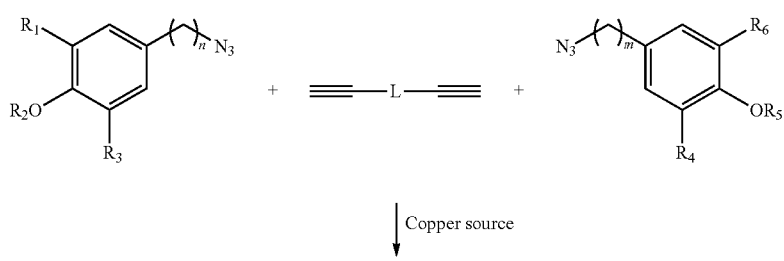

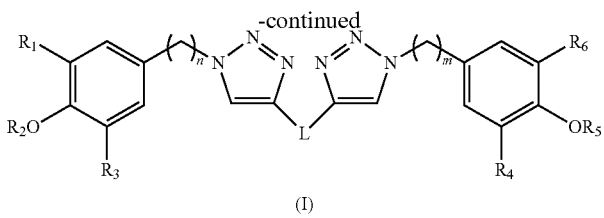

(I)

The copper source used in the reaction may be a copper (II) salt or a cooper (I) salt, in particular copper(II) sulfate pentahydrate, copper(II) acetate hydrate, copper(I) iodide, copper(I) triflate or tetrakis(acetonitrile)copper(I) hexafluorophosphate, preferably copper(II) sulfate pentahydrate.

The reaction may be conducted in a solvent selected from water, an alcohol such as tert-butanol, dimethylformamide, acetonitrile, dimethylsulfoxide, toluene, tetrahydrofurane, and mixtures thereof, preferably a mixture of water and dimethylformamide.

The reaction may be carried out using an additive such as an in situ reducing agent, a ligand, a base and mixtures thereof. Examples of suitable in situ reducing agents are sodium ascorbate, ascorbic acid, tris(2-carboxyethyl)phosphine (TCEP), preferably sodium ascorbate. Examples of suitable ligands are tris(triazolylmethyl)amines such as tris[(1-benzyl-1H-1,2,3-triazol-4-yl)methyl]amine (TBTA), tris[(1-hydroxypropyl-1H-1,2,3-triazol-4-yl)methyl]amine (THPTA), 3-[4-{(bis[(1-tert-butyl-1H-1,2,3-triazol-4-yl)methyl]amino)methyl}-1H-1,2,3-triazol-1-yl]propanol (BTTP), 2-[4-{(bis[(1-tert-butyl-1H-1,2,3-triazol-4-yl)methyl]amino)methyl}-1H-1,2,3-triazol-1-yl]acetic acid (BTTAA), 2-[4-{(bis[(1-tert-butyl-1H-1,2,3-triazol-4-yl)methyl]amino)methyl}-1H-1,2,3-triazol-1-yl]ethyl hydrogen sulfate (BTTES), 3-[4-{(bis[(1-tert-butyl-1H-1,2,3-triazol-4-yl)methyl]amino)methyl}-1H-1,2,3-triazol-1-yl]propyl hydrogen sulfate (BTTPS); tris(heteroarylmethyl)amine ligands such as tris(pyridylmethyl)amines, tris(benzothiazolylmethyl)amines and tris(2-benzimidazolylmethyl)amines; 2,2'-bipyridine and 1,10-phenanthroline derivatives; phosphoramidite ligand MonoPhos, triphenylphosphine; copper(I) bromide dimethyl sulfide complex. Examples of suitable bases are triethylamine, N,N-diisopropylethylamine (DIPEA), pyridine and 2,6-lutidine.

The reaction may be carried out at a temperature of 0° C. to 25° C., in particular 20° C., during 6 to 24 hours, in particular 24 hours.

Composition

The composition according to the present invention comprises a compound of general formula (I) and a carrier.

The carrier may be solid or liquid.

In one embodiment, the composition of the present invention comprises a compound of general formula (I), a solvent, a binder and optionally a filler, a pigment and/or additives. Said composition is suitable for use as a paint, varnish or lacquer to prevent biofilm formation and corrosion of a surface in contact with a liquid.

The solvent may be water or an organic solvent such as hydrocarbons, for example toluene, xylene, and petroleum distillates; alcohols, for example ethanol, isopropanol, n-butanol, isobutanol 2-hexylethanol, isononanol, isodecanol or benzyl alcohol; alkyl ethers or dialkyl ethers of ethylene glycol or propylene glycol, for example hexylene glycol, butylglycol, methyldiglycol, ethyldiglycol, butyldiglycol, butylglycol acetate or propylene glycol methyl ether; esters, for example ethyl acetate, isopropyl acetate, butyl acetate, isobutyl acetate or amyl acetate; ketones, for example methylethylketone, methylbutylketone, methylisobutylketone, cyclohexanone, isophorone, N-methylpyrrolidinone or 4-hydroxy-4-methylpentan-2-one; and mixtures thereof.

The binder is the film-forming component of the composition. The binder may be any binder conventionally used in the formulation of paints and lacquers. Typical binders include synthetic resins, such as alkyds, acrylics, vinylacrylics, vinyl acetate/ethylene (VAE), polyurethanes, polyesters, melamine resins, phenolic resins, epoxy, oils, silicones, and mixtures thereof. Natural resins, such as damar, copal, colophany and lacquer, as well as natural bitumens may also be used as a binder.

Fillers are granular solids that are incorporated to the composition to impart toughness, texture or to reduce its cost. Fillers may be selected from barite, calcium carbonate, dolomite, silica, kaolin, talc, mica, calcium silicate, and mixtures thereof.

Pigments are used to impart a desired color to the composition. The pigments may be any pigments conventionally used in the formulation of paints and lacquers. Suitable pigments include mineral pigments, inorganic pigments, bio-sourced pigments, synthetic pigments and mixtures thereof.

Typical mineral pigments include cadmium pigments, such as cadmium yellow, cadmium red, cadmium green, cadmium orange and cadmium sulfoselenide; chromium pigments, such as chrome yellow and chrome green; cobalt pigments, such as cobalt violet, cobalt blue, cerulean blue and aureolin; copper pigments, such as Azurite, Egyptian blue and malachite; iron oxide pigments, such as oxide red and red ochre; lead pigments, such as lead white, cremnitz white, Naples yellow, red lead and lead-tin-yellow; manganese pigments, such as manganese violet; mercury pigments, such as vermilion; titanium pigments, such as titanium yellow, titanium beige, titanium white and titanium black; and zinc pigments, such as zinc white and zinc ferrite.

Inorganic pigments include carbon pigments, such as carbon black and ivory black; clay earth pigments or iron oxides, such as yellow ochre, raw sienna, burnt sienna, raw umber and burnt umber; and ultramarine pigments, such as ultramarine and ultramarine green shade.

Bio-sourced pigments include gamboge, cochineal red, rose madder, indigo, Indian yellow and Tyrian purple.

Synthetic pigments include alizarin, alizarin crimson, quinacridone, magenta, Phthalocyanine Green G, Phthalocyanine Blue BN, pigment red 170 and diarylide yellow.

Additives that can be introduced in the composition of the invention include surfactants, thickening agents, antifoaming agents, plasticizers, hardeners, and mixtures thereof.

According to one embodiment the amount of compound of general formula (I) in the composition of the present invention is from 0.01 to 10% by weight, in particular 0.1 to 8%, more particularly 0.5 to 6% by weight based on the weight of the composition.

Medical Use

Another object of the present invention is a compound of general formula (I) as defined herein for use as a medicament.

According to an embodiment, the compound of general formula (I) may be used to prevent biofilm formation in the oral cavity of a subject.

In particular, the compound of general formula (I) may be used to prevent the formation of dental plaque.

The compound of general formula (I) may also be used to prevent endodontic infection in the dental root canal.

Non-Therapeutic Use

Another object of the present invention is the non-therapeutic use of a compound of general formula (I) as an anti-biofilm agent, an anti-fouling agent, an antibacterial agent, and/or an anti-corrosion agent.

Compounds of general formula (I) are able to prevent biofilm formation on a surface by preventing the adhesion of micoorganisms on said surface. As such, the compounds of general formula (I) can be used as anti-biofilm agents and more widely as antibacterial agents and anti-fouling agents.

For example, compounds of general formula (I) may be used to prevent biofilm formation on surgical instruments, drip chambers and catheters or on medical devices prior to their implantation in a subject for example on a prosthesis, a pacemaker, an intrauterine device, an endotracheal tube, a heart valve, or a stent.

Compounds of general formula (I) may also be used to prevent biofilm formation on a surface in contact with a liquid, for example on a ship, on an offshore platform, on nets and cages used in aquaculture, on tanks and pipes used in the food-processing industry, heat exchangers and water distribution systems.

According to another embodiment, the compounds of general formula (I) may also be used as anti-corrosion agents. In particular, compounds of general formula (I) may be used to inhibit corrosion of metallic surfaces in contact with a liquid.

The invention will now be described in more detail with the following examples which are given for purely illustrative purposes and which are not intended to limit the scope of this invention in any manner.

EXAMPLES

Figures

Figure 3:
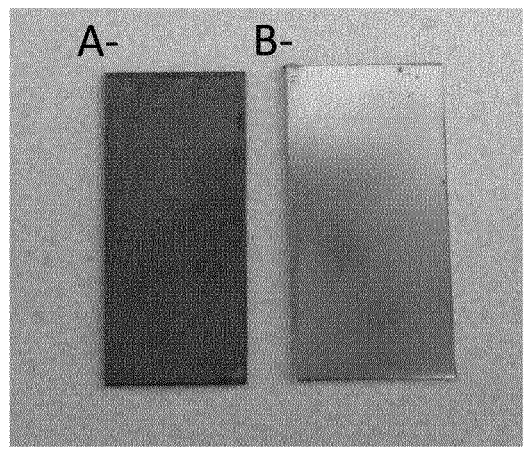

FIG. 3 consists of photos of the steel coupons after one week of immersion in 1N HCl without (A) and with 1 ppm AS171 (B) according to example 66.

Figure 4:
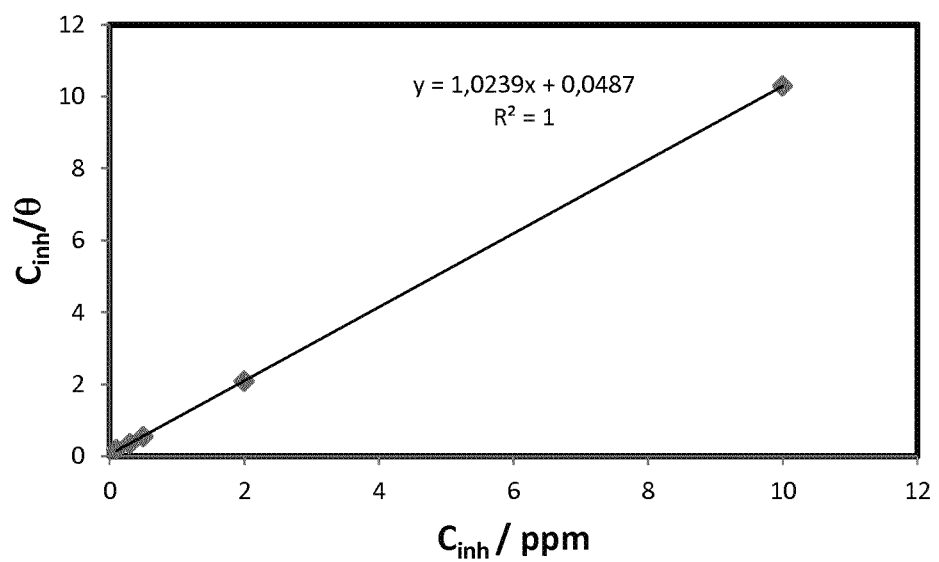

FIG. 4 is the Langmuir adsorption plots for mild steel in 1 M HCl containing different concentrations of AS174 according to example 66.

TEST METHODS

The anti-adhesion bioassays and toxicity tests are adapted from those disclosed in M. Camps, J.-F. Briand, L. Guentas-Dombrowsky, G. Culioli, A. Bazire and Y. Blache, *Mar. Poll. Bull.*, 2011, 62, 1032-1040; and A. Othmani, N. Bouzidi, Y. Viano, Z. Alliche, H. Seridi, Y. Blache, M. El Hattab, J.-F. Briand and G. Culioli, *J Appl Phycol*, 2014, 26, 1573-1584.

The corrosion rates were determined by electrochemical impedance spectroscopy measurements and gravimetry.

Anti-Adhesion Test Method

Bacterial strains were grown on Väätänen nine-salts solution (VNSS). When the stationary phase was reached, the bacterial suspension was centrifuged. Cells were then diluted in sterile artificial sea water (ASW) and introduced in microtiter plates (sterile black PS; Nunc, Fisher Scientific, France) with the tested compound (at eight concentrations in three replicates) in the presence of three controls: (i) non-specific staining control, (ii) adhesion control, and (iii) positive control. The maximum percentage of solvent (DMSO 2%) used to dilute the tested compound was also tested in triplicate as additional control. After incubation during an optimized adhesion time (moderately 15 h), non-adhered bacteria were eliminated and adhered cells were quantified after SYTO 61 (1 µM) staining. A percentage of inhibition was calculated per well. A sigmoid dose-response curve was obtained by plotting the percentage of inhibition as a function of the log of tested compound concentration, after mean (n=3) and standard deviation (SD) calculation per triplicate for each concentration. $EC_{50}$ values were then calculated for each compound.

Toxicity Test Method

After growth on VNSS, bacterial strains were harvested during the exponential phase. The microtiter plates (sterile transparent PS; Nunc, Fisher Scientific) were filled as described in the Anti-adhesion test method using VNSS instead of ASW to allow bacterial growth. The growth was followed by measuring the turbidity ($OD_{600\ nm}$) every hour during 6 or 7 hours. Then, resazurin (50 µM) was added in all the wells, and fluorescence was measured after 2 h to quantify the percent of bacterial viability. The same methodology used with SYTO 61 was applied to calculate a percent of viability after resazurin staining. Only compounds with $EC_{50}$ lower than 200 µM were tested.

Electrochemical Impedance Spectroscopy Test Method

The electrochemical measurements were performed on a 273 A potentiostat (EGG/PAR) coupled to a Solartron 1255 frequency response analyser. EIS measurements were carried out with a solution containing 1N HCl in the absence and presence of the tested compound at a concentration of 200 ppm under unstirred conditions, at open circuit potential with a 10 mV rms amplitude perturbation over a 20 mHz-100 kHz frequency range.

EIS data were registered and analysed using Zview software (Scribners Associates, USA).

A conventional three-electrode cell was used. It comprises a platinum foil as auxiliary electrode, a saturated calomel reference electrode (SCE) and a mild steel coupon as the working electrode with a surface area of 15.7 $cm^2$.

Gravimetry

Weight loss measurements were performed on 2.5×2.0×0.1 cm rectangular mild steel coupons. The mild steel coupons were immersed into non-de-aerated HCl 1N solution in absence and presence of different concentrations of compounds of general formula (I). After the elapsed time, the coupons were taken out, washed, dried and weighed accurately. Experiments were duplicated.

Materials

In examples 64 and 65, the following marine bacterial strains are used.

*Pseudoalteromonas ulvae* (TC14) was isolated in June 2010 in the Military Harbor of Toulon (Mediterranean Sea, France) as described in F. Brian-Jaisson, A. Ortalo-Magné, L. Guentas-Dombrowsky, F. Armougom, Y. Blache, M. Molmeret, *Microb. Ecol.*, 2014, 68, 94-110.

*Pseudoalteromonas lipolytica* (TC8) was isolated in February 2008 in the Toulon Bay (Mediterranean Sea, France) as described in M. Camps, J.-F. Briand, L. Guentas-Dombrowsky, G. Culioli, A. Bazire, Y. Blache, *Mar. Poll. Bull.*, 2011, 62, 1032-1040.

*Paracoccus* sp. (4M6) was isolated in March 2000 in the Morbihan Gulf (Atlantic Ocean, France) as described in B. Grasland, J. Mitalane, R. Briandet, E. Quémener, T. Meylheuc, I. Linossier, K. Vallée-Réhel, D. Haras, *Biofouling*, 2003, 19, 307-313.

*Polaribacter* sp. (TC5) was isolated in June 2010 in the Military Harbor of Toulon (Mediterranean Sea, France) as described in F. Brian-Jaisson, A. Ortalo-Magné, L. Guentas-Dombrowsky, F. Armougom, Y. Blache, M. Molmeret, *Microb. Ecol.*, 2014, 68, 94-110.

*Shewanella* sp. (TC11) was isolated in June 2010 in the Military Harbor of Toulon (Mediterranean Sea, France) as described in F. Brian-Jaisson, A. Ortalo-Magné, L. Guentas-Dombrowsky, F. Armougom, Y. Blache, M. Molmeret, *Microb. Ecol.*, 2014, 68, 94-110.

Example 1

Synthesis of 4-azidophenol (1a)

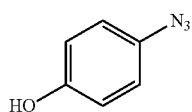

To a stirred solution of 4-aminophenol (2.18 g, 20 mmol) in H$_2$O/HCl (50/50, 20 mL/20 mL) at 0° C. was added NaNO$_2$ (2.76 g, 40 mmol). The reaction mixture was further stirred for 2 h at the same temperature. Then, NaN$_3$ (2.6 g, 40 mmol) was added portion-wise and the reaction mixture was allowed to attain the room temperature while stirring for 3 h. The product was extracted into ethyl acetate (3 times) and the combined organic layer was evaporated to afford 1.92 g (71%) of 4-azidophenol as a dark red oil.

$^1$H NMR (400 MHz, Acetone-d$_6$) δ 8.41 (s, 1H, OH), 6.90 (m, 4H).

$^{13}$C NMR (100 MHz, Acetone-d$_6$) δ 155.9, 131.7, 120.9 (2C), 117.5 (2C).

IR (thin film) v$_{N3}$ 2095 cm$^{-1}$.

Example 2

Synthesis of 4-(2-azidoethyl)-1-bromo-2-methoxybenzene (2a)

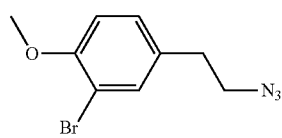

A mixture of 4-(2-chloroethyl)-2-bromo-1-methoxybenzene (1 equiv) and NaN$_3$ (2.6 equiv.) in DMF was stirred for 5 h at 90° C. The mixture was allowed to warm to room temperature and diluted with Et$_2$O. The organic phase was washed with brine and water, dried over Na$_2$SO$_4$, and concentrated under vacuum. The resulting azide was directly used in the next reaction without further purification.

Azide 2a (1.388 g, 94%) was obtained as a dark brown oil.

$^1$H NMR (400 MHz, CDCl$_3$) δ 7.40 (d, J=2.2 Hz, 1H), 7.12 (dd, J=8.4, 2.2 Hz, 1H), 6.85 (d, J=8.4 Hz, 1H), 3.88 (s, 3H), 3.47 (t, J=7.1 Hz, 2H), 2.80 (t, J=7.1 Hz, 2H).

$^{13}$C NMR (100 MHz, CDCl$_3$) δ 154.66, 133.41, 131.59, 128.79, 111.94, 111.55, 56.18, 52.33, 34.04.

IR (thin film) v$_{N3}$ 2090 cm$^{-1}$.

Example 3

Synthesis of 4-(2-azidoethyl)-2-bromophenol (2b)

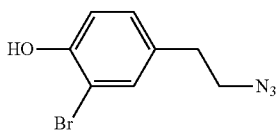

Azide 2b was obtained from 4-(2-chloroethyl)-2-bromophenol using the experimental conditions of example 2.

Azide 2b (2.34 g, 96%) was obtained as a dark brown oil.

$^1$H NMR (400 MHz, CDCl$_3$) δ 7.33 (d, J=2.0 Hz, 1H), 7.07 (dd, J=8.3, 2.0 Hz, 1H), 6.97 (d, J=8.3 Hz, 1H), 5.44 (s, 1H, OH), 3.47 (t, J=7.1 Hz, 2H), 2.80 (t, J=7.1 Hz, 2H).

$^{13}$C NMR (100 MHz, CDCl$_3$) δ 151.1, 132.1, 131.6, 129.4, 116.2, 110.1, 52.3, 34.0.

IR (thin film) v$_{N3}$ 2090 cm$^{-1}$.

Example 4

Synthesis of 4-(2-azidoethyl)phenol (2c)

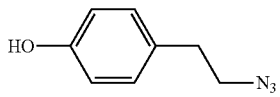

Azide 2c was obtained from 4-(2-chloroethyl)phenol using the experimental conditions of example 2.

Azide 2c (2.5 g, 98%) was obtained as a brown oil.

$^1$H NMR (400 MHz, CDCl$_3$) δ 7.15-7.04 (m, 2H), 6.86-6.76 (m, 2H), 5.20 (s, 1H), 3.46 (t, J=7.2 Hz, 2H), 2.82 (t, J=7.2 Hz, 2H).

$^{13}$C NMR (100 MHz, CDCl$_3$) δ 154.4, 130.3, 130.0 (2C), 115.6 (2C), 52.1, 33.9.

IR (thin film) v$_{N3}$ 2091 cm$^{-1}$.

Example 5

Synthesis of 4-(2-azidoethyl)-2,6-dibromophenol (2d)

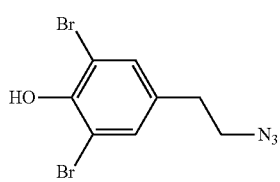

2d

Azide 2d was obtained from 2,6-dibromo-4-(2-chloroethyl)phenol using the experimental conditions of example 2. Azide 2d (1.47 g, 92%) was obtained as a dark brown oil.

$^1$H NMR (400 MHz, CDCl$_3$) δ 7.31 (s, 2H), 5.48 (s, 1H), 3.48 (t, J=6.9 Hz, H), 2.77 (t, J=6.9 Hz, 2H).
$^{13}$C NMR (100 MHz, CDCl3) δ 148.4, 132.8, 132.3 (2C), 109.9 (2C), 52.2, 33.9.
IR (thin film) $v_{N3}$ 2092 cm$^{-1}$.

Example 6

Synthesis of 4-(azidomethyl)-2-bromo-1-methoxybenzene (2e)

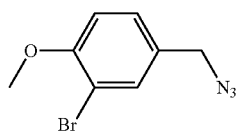

2e

Azide 2e was obtained from 2-bromo-4-(chloromethyl)-1-methoxybenzene using the experimental conditions of example 2. Azide 2e (869 mg, 99%) was obtained as a dark brown oil.

$^1$H NMR (400 MHz, CDCl3) δ 7.51 (d, J=2.2 Hz, 1H), 7.23 (dd, J=8.4, 2.2 Hz, 1H), 6.90 (d, J=8.4 Hz, 1H), 4.26 (s, 2H), 3.90 (s, 3H).
$^{13}$C NMR (100 MHz, CDCl3) δ 155.2, 132.5, 128.4, 128.0, 111.4, 111.1, 55.5, 52.9.
IR (thin film) $v_{N3}$ 2092 cm$^{-1}$.

Example 7

Synthesis of 4-(3-azidopropyl)-2-bromophenol (2f)

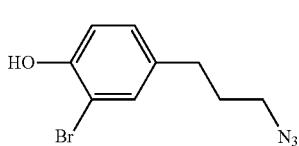

2f

Azide 2f was obtained from 2-bromo-4-(3-chloropropyl)phenol using the experimental conditions of example 2.
Azide 2f (3 g, 92%) was obtained as a dark brown oil.

$^1$H NMR (400 MHz, CDCl$_3$) δ 7.28 (d, J=2.1 Hz, 1H), 7.03 (dd, J=8.3, 2.1 Hz, 1H), 6.95 (d, J=8.3 Hz, 1H), 5.41 (s, 1H), 3.28 (t, J=6.7 Hz, 2H), 2.61 (t, J=7.8 Hz, 2H), 1.86 (m, 2H).
$^{13}$C NMR (100 MHz, CDCl3) δ 150.7, 134.6, 131.7, 129.3, 116.1, 110.2, 50.5, 31.6, 30.6.
IR (thin film) $v_{N3}$ 2093 cm$^{-1}$.

Example 8

Synthesis of 4-(2-azidoethyl)-2-chlorophenol (2q)

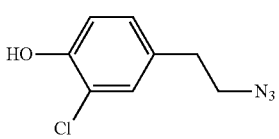

2g

Azide 2g was obtained from 2-chloro-4-(2-chloroethyl)phenol using the experimental conditions of example 2.
Azide 2g (1.56 g, 79%) was obtained as a brown oil.

$^1$H NMR (400 MHz, CDCl$_3$) δ 7.23 (d, J=2.2 Hz, 1H), 7.08 (dd, J=8.4, 2.2 Hz, 1H), 6.88 (d, J=8.4 Hz, 1H), 3.89 (s, 3H), 3.67 (t, J=7.3 Hz, 2H), 2.99 (t, J=7.3 Hz, 2H).
$^{13}$C NMR (100 MHz, CDCl$_3$) δ 154.1, 131.3, 130.7, 128.3, 122.5, 112.2, 56.3, 45.0, 38.1.
IR (thin film) $v_{N3}$ 2090 cm$^{-1}$.

Example 9

Synthesis of 4-(2-azidoethyl)-2-iodophenol (2h)

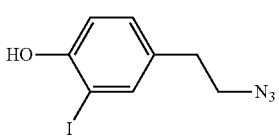

2h

Azide 2h was obtained from 4-(2-chloroethyl)-2-iodophenol using the experimental conditions of example 2.
Azide 2h (2.75 g, 95%) was obtained as a brown oil.

$^1$H NMR (400 MHz, CDCl$_3$) δ 7.63 (d, J=1.4 Hz, 1H), 7.15 (dd, J=8.4, 1.4 Hz, 1H), 6.75 (d, J=8.4 Hz, 1H), 3.83 (s, 3H), 3.65 (t, J=7.2 Hz, 2H), 2.94 (t, J=7.2 Hz, 2H).
$^{13}$C NMR (100 MHz, CDCl$_3$) δ 156.8, 139.4, 132.0, 129.8, 110.7, 85.9, 56.3, 44.9, 37.4.
IR (thin film) $v_{N3}$ 2091 cm$^{-1}$.

Example 10

Synthesis of 2-(4-(2-azidoethyl)phenoxy)-N,N-dimethylethanamine (3a)

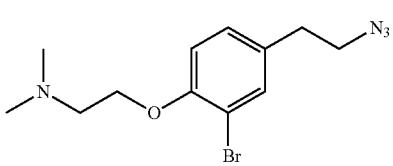

3a

A mixture of azide 2b (3.5 g, 14.5 mmol, 1 equiv.), $K_2CO_3$ (2.5 equiv.), 18-Crown-6 (0.02 equiv.) and 2-chloro-N,N-dimethylethylamine (1.2 equiv.) in anhydrous acetone was stirred at reflux for 15 h. The solvent was evaporated under vacuum and the residue was extracted with chloroform followed by washing with brine (3 times). The organic layers were dried over $Na_2SO_4$, filtered and evaporated under vacuum. The resulting azide was directly used in the next reaction without further purification.

Azide 3a (4.5 g, 99%) was obtained as a brown oil.

$^1$H NMR (400 MHz, $CDCl_3$) δ 7.39 (d, J=2.2 Hz, 1H), 7.09 (dd, J=8.4, 2.2 Hz, 1H), 6.84 (d, J=8.4 Hz, 1H), 4.11 (t, J=5.9 Hz, 2H), 3.46 (t, J=7.1 Hz, 2H), 2.80 (m, 4H), 2.37 (s, 6H).

$^{13}$C NMR (100 MHz, $CDCl_3$) δ 154.1, 133.4, 131.7, 128.6, 113.3, 112.2, 67.9, 57.8, 52.3, 46.1 (2C), 34.0.

IR (thin film) $v_{N3}$ 2093 cm$^{-1}$.

Example 11

Synthesis of 3-(4-(2-azidoethyl)phenoxy)-N,N-dimethylpropan-1-amine (3b)

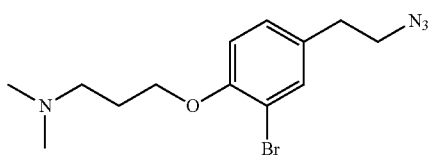

Azide 3b was obtained from azide 2b (3 g, 12.4 mmol) and 2-chloro-N,N-dimethylpropylamine hydrochloride (2.35 g, 14.9 mmol) using the experimental conditions of example 10.

Azide 3b was obtained (4.04 g, 99%) as a brown oil.

$^1$H NMR (400 MHz, $CDCl_3$) δ 7.39 (d, J=1.8 Hz, 1H), 7.08 (dd, J=8.4, 1.8 Hz, 1H), 6.84 (d, J=8.4 Hz, 1H), 4.06 (t, J=6.3 Hz, 2H), 3.46 (t, J=7.1 Hz, 2H), 2.79 (t, J=7.1 Hz, 2H), 2.49 (t, J=7.1 Hz, 2H), 2.25 (s, 6H), 2.02-1.93 (m, 2H).

$^{13}$C NMR (100 MHz, $CDCl_3$) δ 154.2, 133.3, 131.5, 128.6, 113.3, 112.2, 67.3, 56.1, 52.3, 45.4 (2C), 34.1, 27.3.

IR (thin film) $v_{N3}$ 2092 cm$^{-1}$.

Example 12

Synthesis of 2-(4-(2-azidoethyl)phenoxy)-N,N-dimethylethanamine (3d)

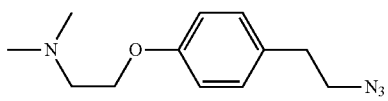

Azide 3d was obtained from azide 2c (0.6 g, 3.7 mmol) and 2-chloro-N,N-dimethylethylamine hydrochloride (0.64 g, 4.4 mmol) using the experimental conditions of example 10.

Azide 3d was obtained (0.84 g, 97%) as a brown oil.

$^1$H NMR (400 MHz, $CDCl_3$) δ 7.08 (d, J=8.1 Hz, 2H), 6.84 (d, J=8.1 Hz, 2H), 4.01 (t, J=5.7 Hz, 2H), 3.41 (t, J=7.2 Hz, 2H), 2.78 (t, J=7.2 Hz, 2H), 2.68 (t, J=5.1 Hz, 2H), 2.29 (s, 6H).

$^{13}$C NMR (100 MHz, $CDCl_3$) δ 157.7, 130.0, 129.6 (2C), 114.6 (2C), 65.9, 58.2, 52.6, 45.8 (2C), 34.4.

IR (thin film) $v_{N3}$ 2091 cm$^{-1}$.

Example 13

Synthesis of 3-(4-(2-azidoethyl)phenoxy)-N,N-dimethylpropan-1-amine (3e)

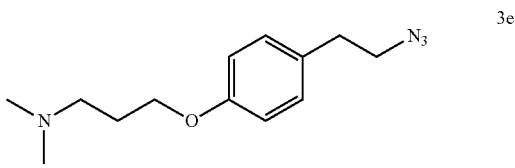 [SMILES: CN(C)CCCOc1ccc(CCN=[N+]=[N-])cc1]

Azide 3e was obtained from azide 2c (0.6 g, 3.7 mmol) and 2-chloro-N,N-dimethylpropylamine hydrochloride (0.69 g, 4.4 mmol) using the experimental conditions of example 10.

Azide 3e was obtained (0.87 g, 95%) as a brown oil.

$^1$H NMR (400 MHz, $CDCl_3$) δ 7.08 (d, J=8.0 Hz, 2H), 6.84 (d, J=8.0 Hz, 2H), 4.02 (t, J=6.3 Hz, 2H), 3.46 (t, J=7.1 Hz, 2H), 2.79 (t, J=7.1 Hz, 2H), 2.49 (t, J=7.1 Hz, 2H), 2.25 (s, 6H), 2.01-1.95 (m, 2H).

$^{13}$C NMR (100 MHz, $CDCl_3$) δ 157.3, 129.8, 129.4 (2C), 114.4 (2C), 67.7, 56.4, 52.4, 45.4 (2C), 34.1, 27.5.

IR (thin film) $v_{N3}$ 2092 cm$^{-1}$.

Example 14

Synthesis of 2-(4-(2-azidoethyl)-2,6-dibromophenoxy)-N,N-dimethylethanamine (3f)

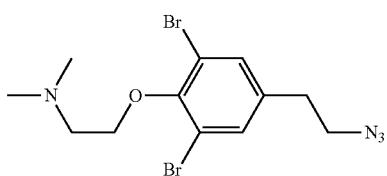

Azide 3f was obtained from azide 2d (0.64 g, 2 mmol) and 2-chloro-N,N-dimethylethylamine hydrochloride (0.35 g, 2.4 mmol) using the experimental conditions of example 10.

Azide 3f was obtained (0.71 g, 90%) as a brown oil.

$^1$H NMR (400 MHz, $CDCl_3$) δ 7.23 (s, 2H), 3.94 (t, J=5.9 Hz, 2H), 3.36 (t, J=7.0 Hz, 2H), 2.72-2.58 (m, 4H), 2.23 (s, 6H).

$^{13}$C NMR (100 MHz, $CDCl_3$) δ 151.9, 136.6, 132.7 (2C), 118.0 (2C), 70.3, 58.5, 51.6, 45.6 (2C), 33.8.

IR (thin film) $v_{N3}$ 2092 cm$^{-1}$.

Example 15

Synthesis of 3-(4-(2-azidoethyl)-2,6-dibromophenoxy)-N,N-dimethylpropan-1-amine (3q)

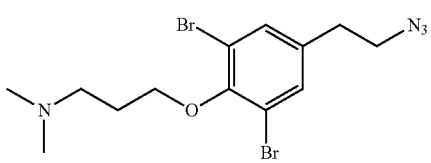

Azide 3g was obtained from azide 2d (0.64 g, 2 mmol) and 2-chloro-N,N-dimethylpropylamine hydrochloride (0.38 g, 2.4 mmol) using the experimental conditions of example 10.

Azide 3g was obtained (0.74 g, 91%) as a brown oil.

$^1$H NMR (400 MHz, CDCl$_3$) δ 7.17 (s, 2H), 3.94 (t, J=6.4 Hz, 2H), 3.40 (t, J=7.0 Hz, 2H), 2.69 (t, J=7.0 Hz, 2H), 2.51-2.41 (m, 2H), 2.19 (s, 6H), 2.01-1.89 (m, 2H).

$^{13}$C NMR (100 MHz, CDCl$_3$) δ 152.2, 136.6, 130.2 (2C), 118.3 (2C), 72.0, 56.3, 51.9, 45.5 (2C), 34.0, 28.3.

IR (thin film) $v_{N3}$ 2090 cm$^{-1}$.

Example 16

Synthesis of 2-(4-(2-azidoethyl)-2-chlorophenoxy)-N,N-dimethylethanamine (3h)

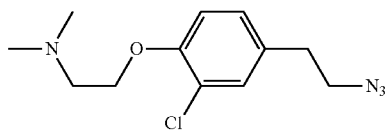

Azide 3h was obtained from azide 2g (0.4 g, 2 mmol) and 2-chloro-N,N-dimethylethylamine hydrochloride (0.35 g, 2.4 mmol) using the experimental conditions of example 10.

Azide 3h was obtained (0.47 g, 88%) as a brown oil.

$^1$H NMR (400 MHz, CDCl$_3$) δ 7.18 (d, J=2.1 Hz, 1H), 7.01 (dd, J=8.4, 2.1 Hz, 1H), 6.84 (d, J=8.4 Hz, 1H), 4.08 (t, J=5.8 Hz, 2H), 3.43 (t, J=7.1 Hz, 2H), 2.81-2.69 (m, 4H), 2.33 (s, 6H).

$^{13}$C NMR (100 MHz, CDCl$_3$) δ 153.3, 131.4, 130.5, 128.0, 123.0, 113.7, 67.9, 58.0, 52.4, 46.1 (2C), 34.2.

IR (thin film) $v_{N3}$ 2091 cm$^{-1}$.

Example 17

Synthesis of 3-(4-(2-azidoethyl)-2-chlorophenoxy)-N,N-dimethylpropan-1-amine (3i)

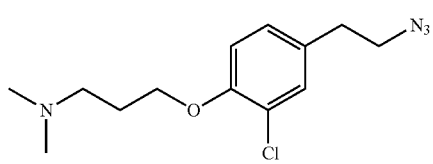

Azide 3i was obtained from azide 2g (0.4 g, 2 mmol) and 2-chloro-N,N-dimethylpropylamine hydrochloride (0.38 g, 2.4 mmol) using the experimental conditions of example 10.

Azide 3i was obtained (0.48 g, 85%) as a brown oil.

$^1$H NMR (400 MHz, CDCl$_3$) δ 7.19 (d, J=2.2 Hz, 1H), 7.02 (dd, J=8.4, 2.2 Hz, 1H), 6.86 (d, J=8.4 Hz, 1H), 4.05 (t, J=6.4 Hz, 2H), 3.44 (t, J=7.1 Hz, 2H), 2.77 (t, J=7.1 Hz, 2H), 2.47 (t, J=7.2 Hz, 2H), 2.23 (s, 6H), 2.02-1.90 (m, 2H).

$^{13}$C NMR (100 MHz, CDCl$_3$) δ 153.5, 131.2, 130.5, 128.0, 123.0, 113.7, 67.5, 56.3, 52.5, 45.6 (2C), 34.3, 27.5.

IR (thin film) $v_{N3}$ 2094 cm$^{-1}$.

Example 18

Synthesis of 2-(4-(2-azidoethyl)-2-iodophenoxy)-N,N-dimethylethanamine (3i)

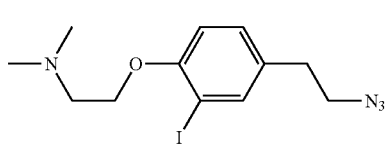

Azide 3j was obtained from azide 2h (0.58 g, 2 mmol) and 2-chloro-N,N-dimethylethylamine hydrochloride (0.35 g, 2.4 mmol) using the experimental conditions of example 10.

Azide 3j was obtained (0.67 g, 93%) as a brown oil.

$^1$H NMR (400 MHz, CDCl$_3$) δ 7.58 (d, J=2.1 Hz, 1H), 7.09 (dd, J=8.3, 2.1 Hz, 1H), 6.71 (d, J=8.3 Hz, 1H), 4.06 (t, J=5.8 Hz, 2H), 3.41 (t, J=7.1 Hz, 2H), 2.83-2.65 (m, 4H), 2.33 (s, 6H).

$^{13}$C NMR (100 MHz, CDCl$_3$) δ 156.3, 139.4, 132.25, 129.7, 112.0, 86.7, 68.0, 57.9, 52.3, 46.2 (2C), 33.8.

IR (thin film) $v_{N3}$ 2093 cm$^{-1}$.

Example 19

Synthesis of 3-(4-(2-azidoethyl)-2-iodophenoxy)-N,N-dimethylpropan-1-amine (3k)

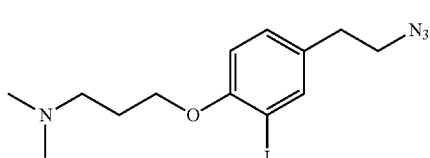

Azide 3k was obtained from azide 2h (0.58 g, 2 mmol) and 2-chloro-N,N-dimethylpropylamine hydrochloride (0.38 g, 2.4 mmol) using the experimental conditions of example 10.

Azide 3k was obtained (0.62 g, 82%) as a brown oil.

$^1$H NMR (400 MHz, CDCl$_3$) δ 7.57 (d, J=2.0 Hz, 1H), 7.07 (dd, J=8.4, 2.0 Hz, 1H), 6.70 (d, J=8.4 Hz, 1H), 3.99 (t, J=6.2 Hz, 2H), 3.40 (t, J=7.1 Hz, 2H), 2.72 (t, J=7.1 Hz, 2H), 2.47 (t, J=7.2 Hz, 2H), 2.21 (s, 6H), 2.00-1.82 (m, 2H).

$^{13}$C NMR (100 MHz, CDCl$_3$) δ 156.4, 139.4, 132.1, 129.7, 112.0, 86.8, 67.4, 56.3, 52.4, 45.5 (2C), 33.9, 27.3.

IR (thin film) $v_{N3}$ 2093 cm$^{-1}$.

Example 20

Synthesis of 2-(4-(3-azidopropyl)-2-bromophenoxy)-N,N-dimethylethanamine (3l)

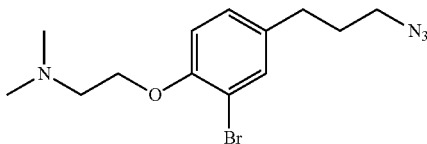

Azide 3l was obtained from azide 2f (0.5 g, 2 mmol) and 2-chloro-N,N-dimethylethylamine hydrochloride (0.35 g, 2.4 mmol) using the experimental conditions of example 10.

Azide 3l was obtained (0.62 g, 95%) as a brown oil.

$^1$H NMR (400 MHz, CDCl$_3$) δ 7.22 (d, J=2.1 Hz, 1H), 6.92 (dd, J=8.4, 2.1 Hz, 1H), 6.70 (d, J=8.4 Hz, 1H), 3.96 (t, J=5.8 Hz, 2H), 3.13 (t, J=6.8 Hz, 2H), 2.65 (t, J=5.8 Hz, 2H), 2.47 (t, J=7.6 Hz, 2H), 1.77-1.65 (m, 2H).

IR (thin film) $v_{N3}$ 2091 cm$^{-1}$.

Example 21

Synthesis of 3-(4-(3-azidopropyl)-2-bromophenoxy)-N,N-dimethylpropan-1-amine (3m)

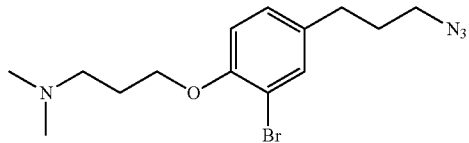

Azide 3m was obtained from azide 2f (0.5 g, 2 mmol) and 2-chloro-N,N-dimethylpropylamine hydrochloride (0.38 g, 2.4 mmol) using the experimental conditions of example 10.

Azide 3m was obtained (0.64 g, 93%) as a brown oil.

$^1$H NMR (400 MHz, CDCl$_3$) δ 7.23 (d, J=2.1 Hz, 1H), 6.92 (dd, J=8.4, 2.1 Hz, 1H), 6.71 (d, J=8.4 Hz, 1H), 3.92 (t, J=6.3 Hz, 2H), 3.14 (t, J=6.7 Hz, 2H), 2.49 (t, J=7.5 Hz, 3H), 2.37 (t, J=7.2 Hz, 2H), 2.13 (s, 6H), 1.92-1.78 (m, 2H), 1.79-1.65 (m, 2H).

$^{13}$C NMR (100 MHz, CDCl$_3$) δ 153.5, 134.1, 132.8, 128.1, 113.1, 111.9, 67.2, 56.0, 50.20, 45.3 (2C), 31.2, 30.2, 27.2.

IR (thin film) $v_{N3}$ 2095 cm$^{-1}$.

Example 22

Synthesis of 2-(4-azidophenoxy)-N,N-dimethylethanamine (3n)

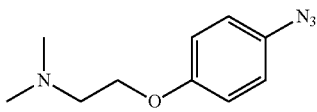

Azide 3n was obtained from azide 1a (0.27 g, 2 mmol) and 2-chloro-N,N-dimethylethylamine hydrochloride (0.35 g, 2.4 mmol) using the experimental conditions of example 10.

Azide 3n was obtained (0.3 g, 74%) as a brown oil.

$^1$H NMR (400 MHz, CDCl$_3$) δ 7.01-6.71 (m, 4H), 3.98 (t, J=5.7 Hz, 2H), 2.66 (t, J=5.7 Hz, 2H), 2.28 (s, 6H).

$^{13}$C NMR (100 MHz, CDCl$_3$) δ 156.2, 132.3, 119.9 (2C), 115.8 (2C), 66.3, 58.2, 45.8 (2C).

IR (thin film) $v_{N3}$ 2096 cm$^{-1}$.

Example 23

Synthesis of 3-(4-azidophenoxy)-N,N-dimethylpropan-1-amine (3o)

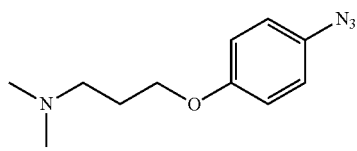

Azide 3o was obtained from azide 1a (0.27 g, 2 mmol) and 2-chloro-N,N-dimethylpropylamine hydrochloride (0.38 g, 2.4 mmol) using the experimental conditions of example 10.

Azide 3o was obtained (0.29 g, 67%) as a brown oil.

$^1$H NMR (400 MHz, CDCl$_3$) δ 7.04-6.63 (m, 4H), 3.95 (t, J=6.4 Hz, 2H), 2.40 (d, J=7.4 Hz, 2H), 2.22 (s, 6H), 1.97-1.86 (m, 2H).

$^{13}$C NMR (100 MHz, CDCl$_3$) δ 156.5, 132.2, 120.0 (2C), 115.8 (2C), 66.6, 56.4, 45.5 (2C), 27.6.

IR (thin film) $v_{N3}$ 2095 cm$^{-1}$.

Example 24

Synthesis of 4-(2-(4-(3-(1-(3-bromo-4-hydroxyphenethyl)-1H-1,2,3-triazol-4-yl)propyl)-1H-1,2,3-triazol-1-yl)ethyl)-2-bromophenol (NT21)

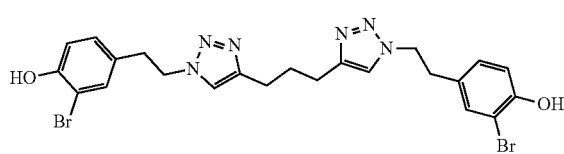

Azide 2b (251.8 mg, 1.04 mmol, 2.6 equiv.) and 1,6-heptadiyne (36.84 mg, 0.4 mmol, 1 equiv.) were dissolved in a 1:2 mixture of water and DMF, CuSO$_4$.5H$_2$O (0.04 equiv) and sodium ascorbate (0.08 equiv) were then added. The resultant mixture was stirred at room temperature for 24 h. The reaction solution was diluted with brine and extracted three times with chloroform. The organic layers were washed with water, dried over Na$_2$SO$_4$ and evaporated under vacuum. The residue was purified by silica gel column chromatography using a mixture of dichloromethane/methanol as the mobile phase.

NT21 was obtained (213 mg, 92%) as a white solid.

$^1$H NMR (400 MHz, DMSO) δ 10.06 (s, 2H, OH), 7.74 (s, 2H), 7.28 (d, J=2.1 Hz, 2H), 6.94 (dd, J=8.2, 2.1 Hz, 2H), 6.82 (d, J=8.2 Hz, 2H), 4.48 (t, J=7.2 Hz, 4H), 3.02 (t, J=7.2 Hz, 4H), 2.58 (t, J=7.4 Hz, 4H), 1.85 (p, J=7.4 Hz, 2H).

$^{13}$C NMR (100 MHz, DMSO) δ 152.8 (2C), 146.5 (2C), 133.1 (2C), 130.1 (2C), 129.2 (2C), 122.3 (2C), 116.4 (2C), 109.3 (2C), 50.7 (2C), 34.7 (2C), 29.1 (2C), 24.4 (1C).

Example 2

Synthesis of 4-(2-(4-(4-(1-(3-bromo-4-hydroxyphenethyl)-1H-1,2,3-triazol-4-yl)butyl)-1H-1,2,3-triazol-1-yl)ethyl)-2-bromophenol (NT22)

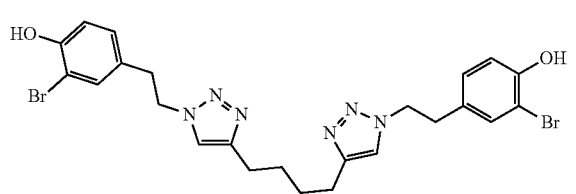

NT22 was obtained from azide 2b (251.8 mg, 1.04 mmol) and 1,7-octadiyne (42.5 mg, 0.4 mmol) using the experimental conditions of example 24.

NT22 was obtained (206 mg, 87%) as a white solid.

$^1$H NMR (400 MHz, DMSO) δ 10.22 (s, 2H, OH), 7.72 (s, 2H), 7.26 (d, J=2.1 Hz, 2H), 6.93 (dd, J=8.2, 2.1 Hz, 2H), 6.84 (d, J=8.2 Hz, 2H), 4.47 (t, J=7.2 Hz, 4H), 3.00 (t, J=7.2 Hz, 4H), 2.59 (t, J=6.2 Hz, 4H), 1.57 (p, J=6.2, 4H).

$^{13}$C NMR (100 MHz, DMSO) δ 152.8 (2C), 146.5 (2C), 132.8 (2C), 129.7 (2C), 128.9 (2C), 121.8 (2C), 116.2 (2C), 109.1 (2C), 50.4 (2C), 34.5 (2C), 28.4 (2C), 24.7 (2C).

Example 26

Synthesis of 4-(2-(4-(6-(1-(3-bromo-4-hydroxyphenethyl)-1H-1,2,3-triazol-4-yl)hexyl)-1H-1,2,3-triazol-1-yl)ethyl)-2-bromophenol (NT25)

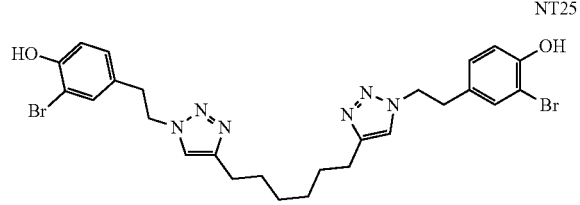 [SMILES: Oc1ccc(CCn2cc(CCCCCCc3cn(CCc4ccc(O)c(Br)c4)nn3)nn2)cc1Br]

NT25 was obtained from azide 2b (251.8 mg, 1.04 mmol) and 1,9-decadiyne (53.7 mg, 0.4 mmol) using the experimental conditions of example 24.

NT25 was obtained (231 mg, 93%) as a white solid.

$^1$H NMR (400 MHz, DMSO) δ 10.08 (s, 2H, OH), 7.72 (s, 2H), 7.26 (d, J=2.0 Hz, 2H), 6.93 (dd, J=8.2, 2.0 Hz, 2H), 6.82 (d, J=8.2 Hz, 2H), 4.47 (t, J=7.2 Hz, 4H), 3.01 (t, J=7.2 Hz, 4H), 2.56 (t, J=7.4 Hz, 4H), 1.66-1.43 (m, 4H), 1.28 (m, 4H).

$^{13}$C NMR (100 MHz, DMSO) δ 152.6 (2C), 146.6 (2C), 132.8 (2C), 129.8 (2C), 128.9 (2C), 121.7 (2C), 116.7 (2C), 109.1 (2C), 50.4 (2C), 34.5 (2C), 29.0 (2C), 28.2 (2C), 24.9 (2C).

Example 27

Synthesis of bis-triazole NT24

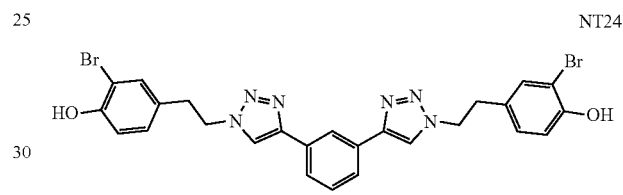

NT24 was obtained from azide 2b (251.8 mg, 1.04 mmol) and 1,3-diethynylbenzene (50.48 mg, 0.4 mmol) using the experimental conditions of example 24.

NT24 was obtained (188 mg, 77%) as a white solid.

$^1$H NMR (400 MHz, DMSO) δ 10.10 (s, 2H, OH), 8.58 (s, 2H), 8.32 (s, 1H), 7.75 (d, J=7.6 Hz, 2H), 7.50 (t, J=7.6 Hz, 1H), 7.37 (d, J=1.4 Hz, 2H), 6.98 (dd, J=8.2, 1.4 Hz, 2H), 6.84 (d, J=8.2 Hz, 2H), 4.61 (t, J=7.0 Hz, 4H), 3.12 (t, J=7.0 Hz, 4H).

$^{13}$C NMR (100 MHz, DMSO) δ 153.2 (2C), 146.4 (2C), 133.4 (2C), 131.9 (2C), 130.2 (2C), 130.0 (1C), 129.4 (2C), 125.0 (2C), 122.15 (1C), 122.1 (2C), 116.7 (2C), 109.6 (2C), 51.3 (2C), 34.8 (2C).

Example 28

Synthesis of 1,4 bis (1-(3-bromo-4-hydroxyphenethyl)-1H-1,2,3-triazol-4-yl) benzene (NT23)

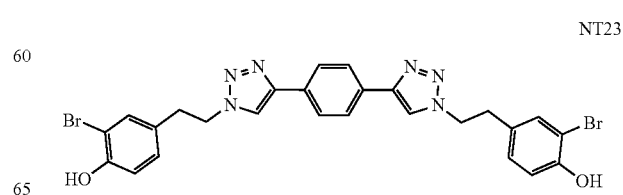

NT23 was obtained from azide 2b (251.8 mg, 1.04 mmol) and 1,4-diethynylbenzene (50.5 mg, 0.4 mmol) using the experimental conditions of example 24.

NT23 was obtained (195 mg, 80%) as a yellow solid.

$^1$H NMR (400 MHz, DMSO) δ 10.11 (s, 2H, OH), 8.55 (s, 2H), 7.88 (s, 4H), 7.37 (d, J=1.9 Hz, 2H), 6.98 (dd, J=8.2, 1.9 Hz, 2H), 6.84 (d, J=8.2 Hz, 2H), 4.60 (t, J=7.1 Hz, 4H), 3.11 (t, J=7.1 Hz, 4H).

$^{13}$C NMR (100 MHz, DMSO) δ 152.7 (2C), 145.8 (2C), 132.9 (2C), 130.2 (2C), 129.7 (2C), 129.0 (2C), 125.6 (4C), 121.4 (2C), 116.2 (2C), 109.1 (2C), 50.8 (2C), 34.3 (2C).

Example 29

Synthesis of bis-triazole NT26

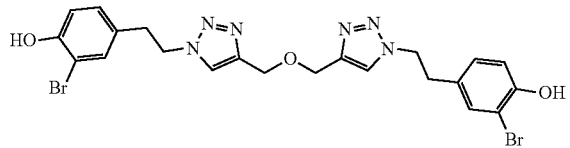

NT26

NT26 was obtained from azide 2b (251.8 mg, 1.04 mmol) and propargyl ether (37.64 mg, 0.4 mmol) using the experimental conditions of example 24.

NT26 was obtained (201 mg, 87%) as a yellow solid.

$^1$H NMR (400 MHz, DMSO) δ 10.09 (s, 2H, OH), 8.01 (s, 2H), 7.33 (d, J=1.6 Hz, 2H), 6.95 (dd, J=8.2, 1.6 Hz, 2H), 6.84 (d, J=8.2 Hz, 2H), 4.54 (m, 8H), 3.05 (t, J=7.1 Hz, 4H).

$^{13}$C NMR (100 MHz, DMSO) δ 153.1 (2C), 144.0 (2C), 133.3 (2C), 130.1 (2C), 129.4 (2C), 124.5 (2C), 116.7 (2C), 109.6 (2C), 62.86 (2C), 51.0 (2C), 34.9 (2C).

Example 30

Synthesis of 1-(3-bromo-4-methoxyphenethyl)-4-(3-(1-(3-bromo-4-methoxyphenethyl)-1H-1,2,3-triazol-4-yl)propyl)-1H-1,2,3-triazole (NT10)

NT10 was obtained from azide 2a (266.3 mg, 1.04 mmol) and 1,6-heptadiyne (36.8 mg, 0.4 mmol) using the experimental conditions of example 24.

NT10 was obtained (221 mg, 91%) as a white solid.

$^1$H NMR (400 MHz, CDCl$_3$) δ 7.24 (d, J=2.1 Hz, 2H), 7.04 (s, 2H), 6.91 (dd, J=8.4, 2.1 Hz, 2H), 6.76 (d, J=8.4 Hz, 2H), 4.47 (t, J=7.1 Hz, 4H), 3.80 (s, 6H), 3.08 (t, J=7.1 Hz, 4H), 2.64 (t, J=7.4 Hz, 4H), 1.94 (p, J=7.4 Hz, 2H).

$^{13}$C NMR (100 MHz, CDCl$_3$) δ 154.9 (2C), 147.2 (2C), 133.4 (2C), 130.7 (2C), 128.9 (2C), 121.5 (2C), 112.1 (2C), 111.7 (2C), 56.3 (2C), 51.4 (2C), 35.6 (2C), 29.1 (2C), 24.7 (1C).

Example 31

Synthesis of 1-(3-bromo-4-methoxyphenethyl)-4-(4-(1-(3-bromo-4-methoxyphenethyl)-1H-1,2,3-triazol-4-yl)butyl)-1H-1,2,3-triazole (NT3)

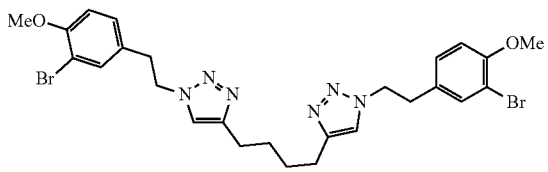

NT3

NT3 was obtained from azide 2a (266.3 mg, 1.04 mmol) and 1,7-octadiyne (42.48 mg, 0.4 mmol) using the experimental conditions of example 24.

NT3 was obtained (238 mg, 96%) as a yellow solid.

$^1$H NMR (400 MHz, CDCl$_3$) δ 7.20 (d, J=2.1 Hz, 2H), 7.03 (s, 2H), 6.89 (dd, J=8.4, 2.1 Hz, 2H), 6.73 (d, J=8.4 Hz, 2H), 4.43 (t, J=7.2 Hz, 4H), 3.78 (s, 6H), 3.04 (t, J=7.2 Hz, 4H), 2.63 (br, 4H), 1.61 (br, 4H).

$^{13}$C NMR (100 MHz, CDCl$_3$) δ 154.8 (2C), 147.6 (2C), 133.3 (2C), 130.7 (2C), 128.7 (2C), 121.2 (2C), 112.0 (2C), 111.6 (2C), 56.2 (2C), 51.3 (2C), 35.4 (2C), 28.8 (2C), 25.2 (2C).

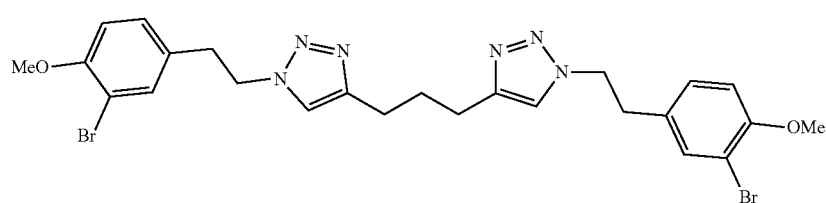

NT10

Example 32

Synthesis of 1-(3-bromo-4-methoxyphenethyl)-4-(6-(1-(3-bromo-4-methoxyphenethyl)-1H-1,2,3-triazol-4-yl)hexyl)-1H-1,2,3-triazole (NT4)

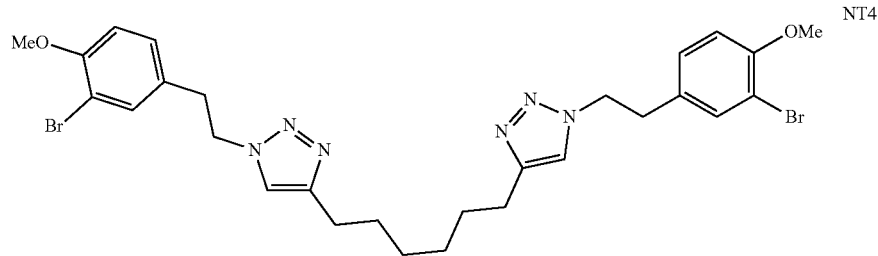 [SMILES: COc1ccc(CCn2cc(CCCCCCc3cn(CCc4ccc(OC)c(Br)c4)nn3)nn2)cc1Br]

NT4 was obtained from azide 2a (266.3 mg, 1.04 mmol) and 1,9-decadiyne (53.7 mg, 0.4 mmol) using the experimental conditions of example 24.

NT4 was obtained (251 mg, 97%) as a yellow oil.

$^1$H NMR (400 MHz, CDCl$_3$) δ 7.23 (d, J=2.1 Hz, 2H), 7.03 (s, 2H), 6.92 (dd, J=8.4, 2.1 Hz, 2H), 6.76 (d, J=8.4 Hz, 2H), 4.46 (t, J=7.2 Hz, 4H), 3.81 (s, 6H), 3.07 (t, J=7.2 Hz, 4H), 2.62 (t, J=7.5 Hz, 4H), 1.58 (br, 4H), 1.32 (br, 4H).

$^{13}$C NMR (100 MHz, CDCl$_3$) δ 154.9 (2C), 148.0 (2C), 133.4 (2C), 130.8 (2C), 128.8 (2C), 121.1 (2C), 112.1 (2C), 111.7 (2C), 56.3 (2C), 51.4 (2C), 35.6 (2C), 29.3 (2C), 28.8 (2C), 25.5 (2C).

Example 33

Synthesis of 1-(3-bromo-4-methoxyphenethyl)-4-(3-(1-(3-bromo-4-methoxyphenethyl)-1H-1,2,3-triazol-4-yl)phenyl)-1H-1,2,3-triazole (NT5)

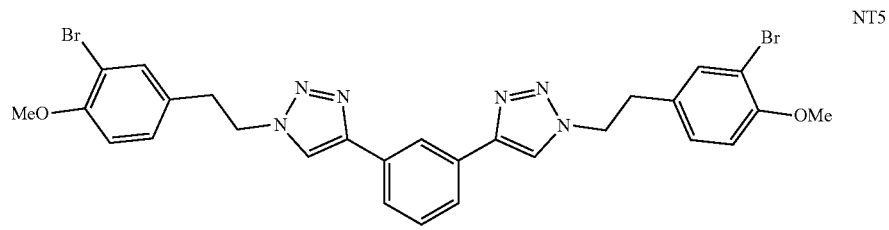 [SMILES: COc1ccc(CCn2cc(-c3cccc(-c4cn(CCc5ccc(OC)c(Br)c5)nn4)c3)nn2)cc1Br]

NT5 was obtained from azide 2a (266.3 mg, 1.04 mmol) and 1,3-diethynylbenzene (50.5 mg, 0.4 mmol) using the experimental conditions of example 24.

NT5 was obtained (230 mg, 90%) as a white solid.

$^1$H NMR (400 MHz, CDCl$_3$) δ 8.14 (t, J=1.4 Hz, 1H), 7.71 (dd, J=7.8, 1.4 Hz, 2H), 7.64 (s, 2H), 7.38 (t, J=7.8 Hz, 1H), 7.30 (d, J=2.2 Hz, 2H), 6.92 (dd, J=8.4, 2.2 Hz, 2H), 6.72 (d, J=8.4 Hz, 2H), 4.52 (t, J=7.2 Hz, 4H), 3.77 (s, 6H), 3.11 (t, J=7.2 Hz, 4H).

$^{13}$C NMR (100 MHz, CDCl$_3$) δ 154.8 (2C), 147.1 (2C), 133.3 (2C), 131.1 (2C), 130.5 (2C), 129.4 (1C), 128.8 (2C), 125.3 (2C), 122.8 (1C), 120.4 (2C), 112.1 (2C), 111.6 (2C), 56.2 (2C), 51.5 (2C), 35.3 (2C).

Example 34

Synthesis of 4-(((1-(3-bromo-4-methoxyphenethyl)-1H-1,2,3-triazol-4-yl)methoxy)methyl)-1-(3-bromo-4-methoxyphenethyl)-1H-1,2,3-triazole (NT6)

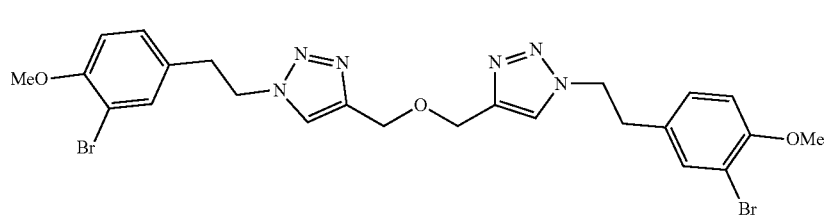

NT6 was obtained from azide 2a (266.3 mg, 1.04 mmol) and propargyl ether (37.6 mg, 0.4 mmol) using the experimental conditions of example 24.

NT6 was obtained (225 mg, 93%) as a brown oil.

$^1$H NMR (400 MHz, CDCl$_3$) δ 7.35 (s, 2H), 7.27 (d, J=2.2 Hz, 2H), 6.93 (dd, J=8.4, 2.2 Hz, 2H), 6.77 (d, J=8.4 Hz, 2H), 4.58 (s, 4H), 4.50 (t, J=7.2 Hz, 6H), 3.81 (s, 6H), 3.10 (t, J=7.2 Hz, 4H).

$^{13}$C NMR (100 MHz, CDCl$_3$) δ 154.9, 144.4, 133.4, 130.5, 128.8, 123.3, 112.2, 111.7, 63.2, 56.3, 51.5, 35.4.

Example 35

Synthesis of bis((1-(3-bromo-4-methoxyphenethyl)-1H-1,2,3-triazol-4-yl)methyl)amine (NT7)

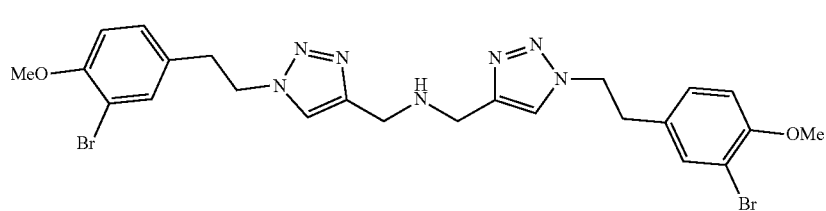

NT7 was obtained from azide 2a (266.3 mg, 1.04 mmol) and dipropargylamine (37.2 mg, 0.4 mmol) using the experimental conditions of example 24.

NT7 was obtained (213 mg, 88%) as a brown solid.

$^1$H NMR (400 MHz, CDCl$_3$) δ 7.34 (s, 2H), 7.24 (d, J=2.1 Hz, 2H), 6.92 (dd, J=8.4, 2.1 Hz, 2H), 6.75 (d, J=8.4 Hz, 2H), 4.48 (t, J=7.2 Hz, 4H), 3.95-3.66 (m, 10H, CH$_2$NH, O CH$_3$), 3.07 (t, J=7.2 Hz, 4H).

$^{13}$C NMR (100 MHz, CDCl$_3$) δ 154.9 (2C), 145.1 (2C), 133.3 (2C), 130.5 (2C), 128.8 (2C), 122.8 (2C), 112.1 (2C), 111.7 (2C), 56.2 (2C), 51.5 (2C), 43.1 (2C), 35.4 (2C).

Example 36

Synthesis of 2-(4-(2-(4-(3-(1-(4-((dimethylamino)methoxy)-3-bromophenethyl)-1H-1,2,3-triazol-4-yl)propyl)-1H-1,2,3-triazol-1-yl)ethyl)-2-bromophenoxy)-N,N-dimethylethanamine (AS158)

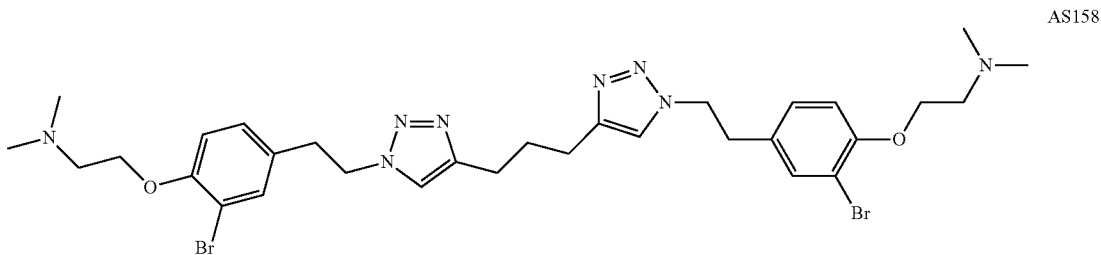

AS158 was obtained from azide 3a (325.6 mg, 1.04 mmol) and 1,6-heptadiyne (36.8 mg, 0.4 mmol) using the experimental conditions of example 24.

AS158 was obtained (267 mg, 93%) as a brown oil.

$^1$H NMR (400 MHz, CDCl$_3$) δ 7.09 (d, J=2.1 Hz, 2H), 7.00 (s, 2H), 6.78 (dd, J=8.4, 2.1 Hz, 2H), 6.65 (d, J=8.4 Hz, 2H), 4.34 (t, J=7.1 Hz, 4H), 3.96 (t, J=5.6 Hz, 4H), 2.94 (t, J=7.1 Hz, 4H), 2.94 (t, J=7.1 Hz, 4H), 2.70 (t, J=5.6 Hz, 4H), 2.51 (t, J=7.4 Hz, 4H), 2.26 (s, 12H), 1.81 (p, J=7.4 Hz, 2H).

$^{13}$C NMR (101 MHz, CDCl$_3$) δ 153.7 (2C), 146.8 (2C), 133.1 (2C), 130.7 (2C), 128.5 (2C), 121.3 (2C), 113.1 (2C), 111.8 (2C), 67.2 (2C), 57.4 (2C), 51.0 (2C), 45.62 (4C), 35.2 (2C), 28.8 (2C), 24.4 (1C).

Example 37

Synthesis of 2-(4-(2-(4-(4-(1-(4-(2-(dimethylamino)ethoxy)-3-bromophenethyl)-1H-1,2,3-triazol-4-yl)butyl)-1H-1,2,3-triazol-1-yl)ethyl)-2-bromophenoxy)-N,N-dimethylethanamine (AS159)

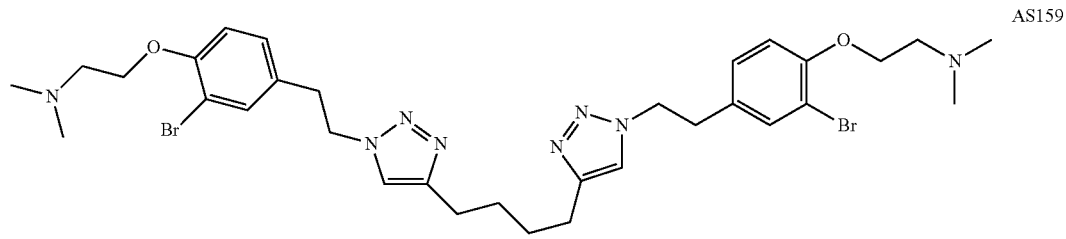

AS159 was obtained from azide 3a (325.6 mg, 1.04 mmol) and 1,7-octadiyne (42.48 mg, 0.4 mmol) using the experimental conditions of example 24.

AS159 was obtained (277 mg, 94%) as a yellow solid.

$^1$H NMR (400 MHz, CDCl$_3$) δ 7.11 (d, J=2.1 Hz, 2H), 6.98 (s, 2H), 6.80 (dd, J=8.4, 2.1 Hz, 2H), 6.66 (d, J=8.4 Hz, 2H), 4.35 (t, J=7.2 Hz, 4H), 3.95 (t, J=5.8 Hz, 4H), 2.96 (t, J=7.2 Hz, 4H), 2.64 (t, J=5.8 Hz, 4H), 2.56 (t, J=5.7 Hz, 4H), 2.22 (s, 12H), 1.63-1.48 (m, 4H).

$^{13}$C NMR (100 MHz, CDCl$_3$) δ 154.0 (2C), 147.4 (2C), 133.1 (2C), 130.7 (2C), 128.5 (2C), 121.0 (2C), 113.1 (2C), 111.9 (2C), 67.7 (2C), 57.6 (2C), 51.1 (2C), 45.96 (4C), 35.3 (2C), 28.6 (2C), 25.0 (2C).

Example 38

Synthesis of 2-(4-(2-(4-(6-(1-(4-(2-(dimethylamino)ethoxy)-3-bromophenethyl)-1H-1,2,3-triazol-4-yl)hexyl)-1H-1,2,3-triazol-1-yl)ethyl)-2-bromophenoxy)-N,N-dimethylethanamine (AS160)

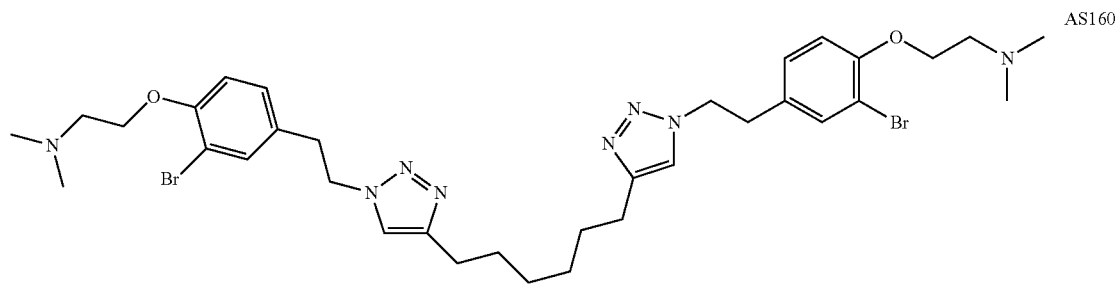

AS160 was obtained from azide 3a (325.6 mg, 1.04 mmol) and 1,9-decadiyne (53.7 mg, 0.4 mmol) using the experimental conditions of example 24.

AS160 was obtained (271 mg, 89%) as a yellow solid.

$^1$H NMR (400 MHz, CDCl$_3$) δ 7.15 (d, J=2.2 Hz, 2H), 6.99 (s, 2H), 6.84 (dd, J=8.4, 2.2 Hz, 2H), 6.69 (d, J=8.4 Hz, 2H), 4.38 (t, J=7.2 Hz, 4H), 4.00 (t, J=5.7 Hz, 4H), 2.99 (t, J=7.2 Hz, 4H), 2.71 (t, J=5.7 Hz, 4H), 2.54 (t, J=7.6 Hz, 4H), 2.28 (s, 12H), 1.64-1.36 (m, 4H), 1.33-1.08 (m, 4H).

$^{13}$C NMR (100 MHz, CDCl$_3$) δ 154.0 (2C), 147.8 (2C), 133.2 (2C), 130.8 (2C), 128.6 (2C), 121.0 (2C), 113.2 (2C), 112.04 (2C), 67.6 (2C), 57.7 (2C), 51.2 (2C), 45.9 (4C), 35.4 (2C), 29.2 (2C), 28.6 (2C), 25.3 (2C).

Example 39

Synthesis of 2-(4-(2-(4-(3-(1-(4-(2-(dimethylamino)ethoxy)-3-bromophenethyl)-1H-1,2,3-triazol-4-yl)phenyl)-1H-1,2,3-triazol-1-yl)ethyl)-2-bromophenoxy)-N,N-dimethylethanamine (AS161)

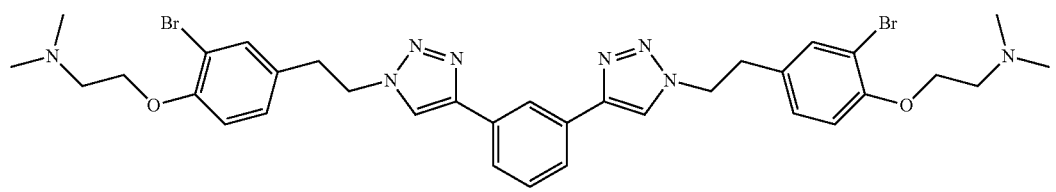

AS161 was obtained from azide 3a (325.6 mg, 1.04 mmol) and 1,3-diethynylbenzene (50.5 mg, 0.4 mmol) using the experimental conditions of example 24.

AS161 was obtained (253 mg, 84%) as a brown oil.

$^1$H NMR (400 MHz, CDCl$_3$) δ 8.09 (t, J=1.6 Hz, 1H), 7.68 (s, 2H), 7.63 (dd, J=7.8, 1.6 Hz, 2H), 7.29 (t, J=7.8 Hz, 1H), 7.21 (d, J=2.1 Hz, 2H), 6.84 (dd, J=8.4, 2.1 Hz, 2H), 6.64 (d, J=8.4 Hz, 2H), 4.45 (t, J=7.2 Hz, 4H), 3.99 (t, J=5.5 Hz, 4H), 3.03 (t, J=7.2 Hz, 4H), 2.75 (t, J=5.5 Hz, 4H), 2.30 (s, 12H).

$^{13}$C NMR (100 MHz, CDCl$_3$) δ 153.8 (2C), 146.8 (2C), 133.2 (2C), 130.9 (2C), 130.6 (2C), 129.2 (1C), 128.6 (2C), 125.0 (2C), 122.6 (1C), 120.4 (2C), 113.1 (2C), 111.9 (2C), 67.0 (2C), 57.2 (2C), 51.3 (2C), 45.4 (4C), 35.1 (2C).

Example 40

Synthesis of 2-(4-(2-(4-(4-(1-(4-(2-(dimethylamino)ethoxy)-3-bromophenethyl)-1H-1,2,3-triazol-4-yl)phenyl)-1H-1,2,3-triazol-1-yl)ethyl)-2-bromophenoxy)-N,N-dimethylethanamine (AS162)

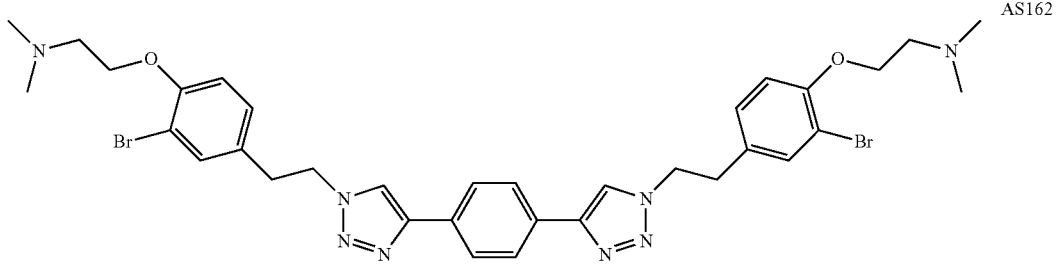

AS162 was obtained from azide 3a (325.6 mg, 1.04 mmol) and 1,4-diethynylbenzene (50.5 mg, 0.4 mmol) using the experimental conditions of example 24.

AS162 was obtained (264 mg, 88%) as a yellow solid.

$^1$H NMR (400 MHz, CDCl$_3$) δ 7.78 (s, 4H), 7.59 (s, 2H), 7.33 (d, J=2.1 Hz, 2H), 6.92 (dd, J=8.2, 2.1 Hz, 2H), 6.76 (d, J=8.2 Hz, 2H), 4.55 (t, J=7.0 Hz, 4H), 4.06 (t, J=5.6 Hz, 4H), 3.14 (t, J=7.0 Hz, 4H), 2.77 (t, J=5.6 Hz, 4H), 2.34 (s, 12H).

$^{13}$C NMR (100 MHz, CDCl$_3$) δ 154.4 (2C), 147.2 (2C), 133.5 (2C), 130.7 (2C), 130.3 (2C), 128.9 (2C), 126.2 (4C), 120.2 (2C), 113.4 (2C), 112.4 (2C), 68.0 (2C), 57.9 (2C), 51.7 (2C), 46.2 (4C), 35.6 (2C).

Example 41

Synthesis of 2-(4-(2-(4-(((1-(4-(2-(dimethylamino)ethoxy)-3-bromophenethyl)-1H-1,2,3-triazol-4-yl)methoxy)methyl)-1H-1,2,3-triazol-1-yl)ethyl)-2-bromophenoxy)-N,N-dimethylethanamine (AS163)

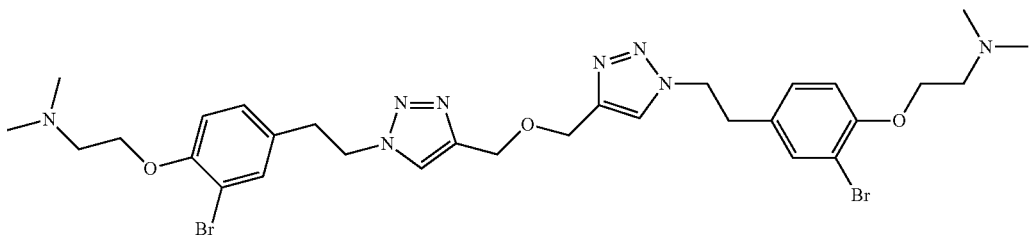

AS163 was obtained from azide 3a (325.6 mg, 1.04 mmol) and propargyl ether (37.6 mg, 0.4 mmol) using the experimental conditions of example 24.

AS163 was obtained (282 mg, 98%) as a yellow solid.

$^1$H NMR (400 MHz, CDCl$_3$) δ 7.32 (s, 2H), 7.14 (d, J=2.1 Hz, 2H), 6.81 (dd, J=8.4, 2.1 Hz, 2H), 6.65 (d, J=8.4 Hz, 2H), 4.46 (s, 4H), 4.38 (t, J=7.2 Hz, 4H), 3.97 (t, J=5.6 Hz, 4H), 2.96 (t, J=7.2 Hz, 4H), 2.70 (t, J=5.6 Hz, 4H), 2.26 (s, 12H).

$^{13}$C NMR (100 MHz, CDCl$_3$) δ 153.8 (2C), 143.9 (2C), 133.1 (2C), 130.5 (2C), 128.5 (2C), 123.1 (2C), 113.1 (2C), 111.8 (2C), 67.2 (2C), 62.9 (2C), 57.4 (2C), 51.1 (2C), 45.6 (4C), 35.1 (2C).

Example 42

Synthesis of bis-triazole AS164

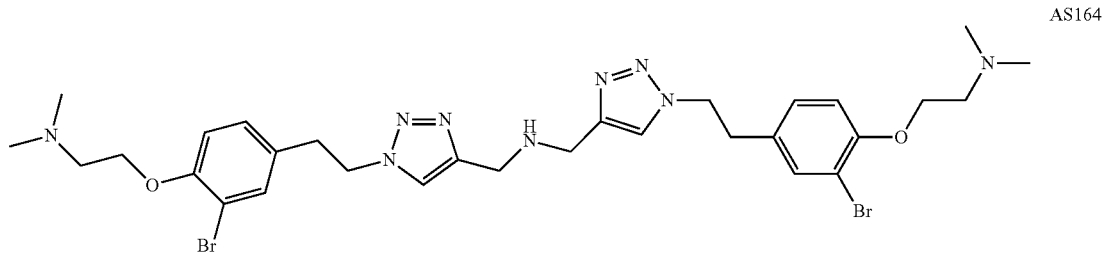

AS164 was obtained from azide 3a (325.6 mg, 1.04 mmol) and dipropargylamine (37.2 mg, 0.4 mmol) using the experimental conditions of example 24.

AS164 was obtained (243 mg, 84%) as a brown solid.

$^1$H NMR (400 MHz, CDCl$_3$) δ 7.33 (s, 2H), 7.22 (d, J=1.8 Hz, 2H), 6.90 (dd, J=8.4, 1.8 Hz, 2H), 6.75 (d, J=8.4 Hz, 2H), 4.46 (t, J=7.2 Hz, 4H), 4.11 (t, J=5.4 Hz, 4H), 3.81 (br, 4H), 3.06 (t, J=7.2 Hz, 4H), 2.89 (t, J=5.4 Hz, 4H), 2.42 (s, 12H).

$^{13}$C NMR (100 MHz, CDCl$_3$) δ 154.0 (2C), 145.3 (2C), 133.4 (2C), 130.9 (2C), 128.8 (2C), 122.7 (2C), 113.3 (2C), 112.1 (2C), 66.8 (2C), 57.2 (2C), 51.4 (2C), 45.3 (4C), 43.1 (2C), 35.4 (2C).

Example 43

Synthesis of 3-(4-(2-(4-(3-(1-(4-(3-(dimethylamino) propoxy)-3-bromophenethyl)-1H-1,2,3-triazol-4-yl) propyl)-1H-1,2,3-triazol-1-yl)ethyl)-2-bromophenoxy)-N,N-dimethylpropan-1-amine (AS168)

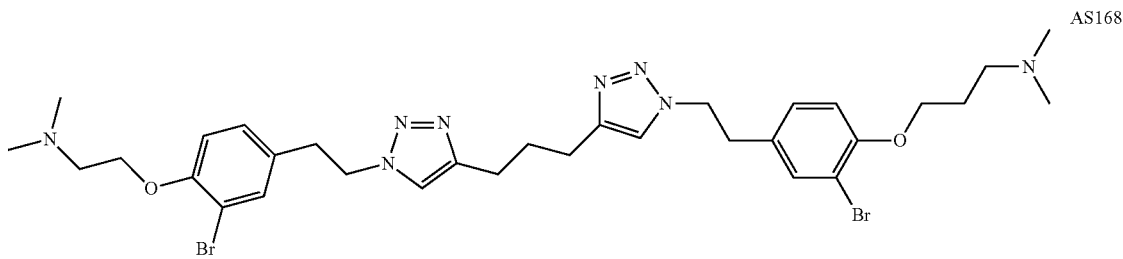

AS168 was obtained from azide 3b (340.3 mg, 1.04 mmol) and 1,6-heptadiyne (36.8 mg, 0.4 mmol) using the experimental conditions of example 24.

AS168 was obtained (266 mg, 89%) as a brown oil.

$^1$H NMR (400 MHz, CDCl$_3$) δ 7.12 (d, J=2.1 Hz, 2H), 6.99 (s, 2H), 6.78 (dd, J=8.4, 2.1 Hz, 2H), 6.65 (d, J=8.4 Hz, 2H), 4.35 (t, J=7.1 Hz, 4H), 3.87 (t, J=6.3 Hz, 4H), 2.95 (t, J=7.1 Hz, 4H), 2.53 (t, J=7.4 Hz, 4H), 2.36 (t, J=7.2 Hz, 4H), 2.11 (s, 12H), 1.90-1.76 (m, 6H).

$^{13}$C NMR (100 MHz, CDCl$_3$) δ 154.0 (2C), 146.8 (2C), 133.0 (2C), 130.4 (2C), 128.5 (2C), 121.3 (2C), 113.1 (2C), 111.9 (2C), 67.0 (2C), 55.8 (2C), 51.1 (2C), 45.2 (4C), 35.3 (2C), 28.8 (2C), 26.9 (2C), 24.4 (1C).

Example 44

Synthesis of 3-(4-(2-(4-(4-(1-(4-(3-(dimethylamino)propoxy)-3-bromophenethyl)-1H-1,2,3-triazol-4-yl)butyl)-1H-1,2,3-triazol-1-yl)ethyl)-2-bromophenoxy)-N,N-dimethylpropan-1-amine (AS169)

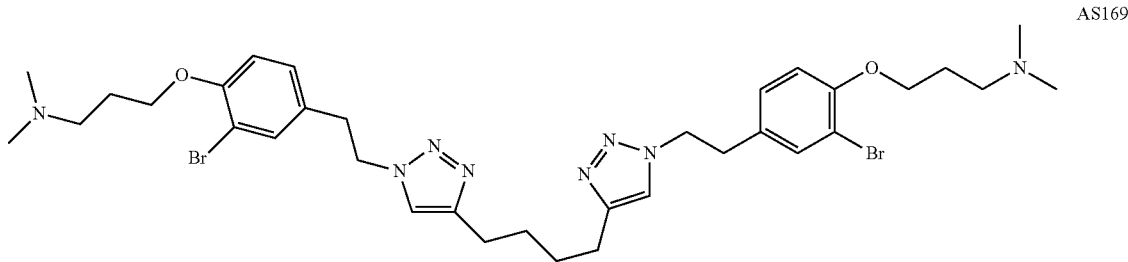

AS169 was obtained from azide 3b (340.3 mg, 1.04 mmol) and 1,7-octadiyne (42.48 mg, 0.4 mmol) using the experimental conditions of example 24.

AS169 was obtained (284 mg, 93%) as a yellow solid.

$^1$H NMR (400 MHz, CDCl$_3$) δ 7.17 (d, J=2.1 Hz, 2H), 7.01 (s, 2H), 6.85 (dd, J=8.4, 2.1 Hz, 2H), 6.72 (d, J=8.4 Hz, 2H), 4.41 (t, J=7.1 Hz, 4H), 3.96 (t, J=6.3 Hz, 4H), 3.02 (t, J=7.1 Hz, 4H), 2.62 (t, J=6.3 Hz, 4H), 2.46 (t, J=7.2 Hz, 4H), 2.20 (s, 12H), 1.97-1.87 (m, 4H), 1.64-1.55 (m, 4H).

$^{13}$C NMR (100 MHz, CDCl$_3$) δ 154.2 (2C), 147.6 (2C), 133.2 (2C), 130.6 (2C), 128.6 (2C), 121.1 (2C), 113.3 (2C), 112.1 (2C), 67.2 (2C), 56.0 (2C), 51.3 (2C), 45.3 (4C), 35.5 (2C), 28.8 (2C), 27.1 (2C), 25.2 (2C).

Example 45

Synthesis of 3-(4-(2-(4-(6-(1-(4-(3-(dimethylamino)propoxy)-3-bromophenethyl)-1H-1,2,3-triazol-4-yl)hexyl)-1H-1,2,3-triazol-1-yl)ethyl)-2-bromophenoxy)-N,N-dimethylpropan-1-amine (AS170)

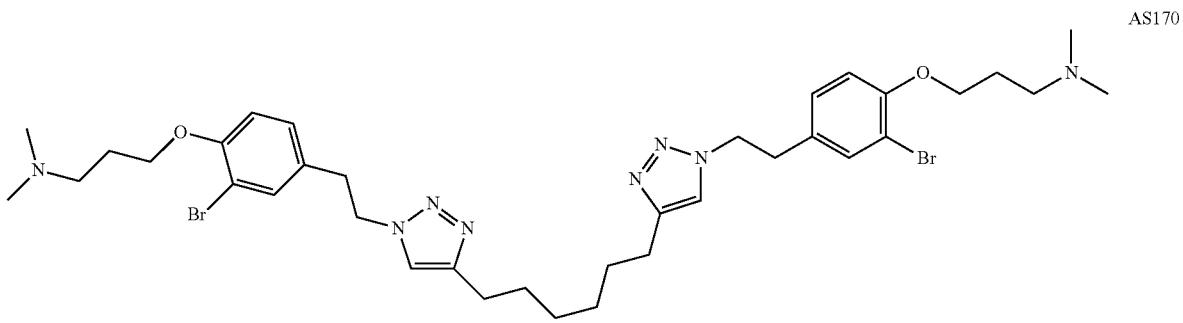

AS170 was obtained from azide 3b (340.3 mg, 1.04 mmol) and 1,9-decadiyne (53.7 mg, 0.4 mmol) using the experimental conditions of example 24.

AS170 was obtained (275 mg, 87%) as a brown solid.

$^1$H NMR (400 MHz, CDCl$_3$) δ 7.18 (d, J=2.1 Hz, 2H), 7.01 (s, 2H), 6.85 (dd, J=8.4, 2.1 Hz, 2H), 6.72 (d, J=8.4 Hz, 2H), 4.41 (t, J=7.2 Hz, 4H), 3.96 (t, J=6.3 Hz, 4H), 3.02 (t, J=7.2 Hz, 4H), 2.58 (t, J=7.6 Hz, 4H), 2.42 (t, J=7.2 Hz, 4H), 2.18 (s, 12H), 1.97-1.83 (m, 4H), 1.65-1.43 (m, 4H), 1.36-1.20 (m, 4H).

$^{13}$C NMR (100 MHz, CDCl$_3$) δ 154.2 (2C), 147.9 (2C), 133.2 (2C), 130.6 (2C), 128.6 (2C), 121.0 (2C), 113.3 (2C), 112.2 (2C), 67.3 (2C), 56.1 (2C), 51.3 (2C), 45.4 (4C), 35.5 (2C), 29.3 (2C), 28.7 (2C), 27.2 (2C), 25.4 (2C).

Example 46

Synthesis of 3-(4-(2-(4-(3-(1-(4-(3-(dimethylamino)propoxy)-3-bromophenethyl)-1H-1,2,3-triazol-4-yl)phenyl)-1H-1,2,3-triazol-1-yl)ethyl)-2-bromophenoxy)-N,N-dimethylpropan-1-amine (AS171)

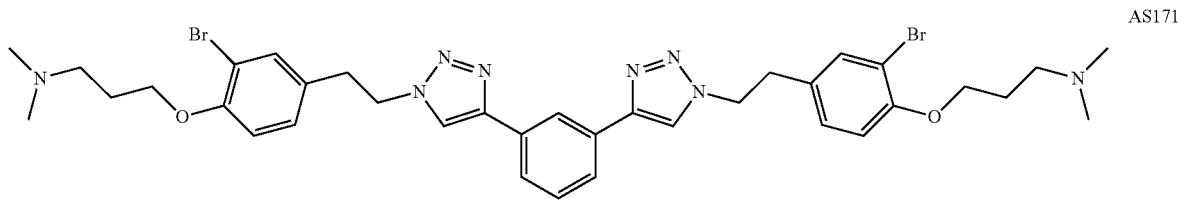

AS171 was obtained from azide 3b (340.3 mg, 1.04 mmol) and 1,3-diethynylbenzene (50.5 mg, 0.4 mmol) using the experimental conditions of example 24.

AS171 was obtained (288 mg, 92%) as a brown oil.

$^{1}$H NMR (400 MHz, CDCl$_{3}$) δ 8.12 (d, J=1.6 Hz, 1H), 7.68 (dd, J=7.7, 1.6 Hz, 2H), 7.64 (s, 2H), 7.35 (t, J=7.7 Hz, 1H), 7.26 (d, J=2.1 Hz, 2H), 6.87 (dd, J=8.4, 2.1 Hz, 2H), 6.70 (d, J=8.4 Hz, 2H), 4.49 (t, J=7.2 Hz, 4H), 3.94 (t, J=6.3 Hz, 4H), 3.07 (t, J=7.2 Hz, 4H), 2.41 (t, J=7.2 Hz, 4H), 2.17 (s, 12H), 1.96-1.79 (m, 4H).

$^{13}$C NMR (100 MHz, CDCl$_{3}$) δ 154.3 (2C), 147.0 (2C), 133.2 (2C), 131.1 (2C), 130.3 (2C), 129.32 (1C), 128.7 (2C), 125.2 (2C), 122.8 (1C), 120.4 (2C), 113.3 (2C), 112.2 (2C), 67.2 (2C), 56.1 (2C), 51.5 (2C), 45.4 (4C), 35.3 (2C), 27.2 (2C).

Example 47

Synthesis of 3-(4-(2-(4-(4-(1-(4-(3-(dimethylamino)propoxy)-3-bromophenethyl)-1H-1,2,3-triazol-4-yl)phenyl)-1H-1,2,3-triazol-1-yl)ethyl)-2-bromophenoxy)-N,N-dimethylpropan-1-amine (AS172)

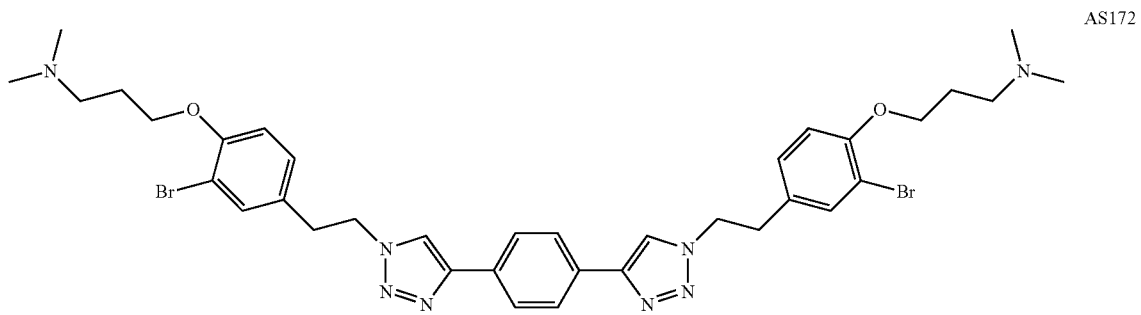

AS172 was obtained from azide 3b (340.3 mg, 1.04 mmol) and 1,4-diethynylbenzene (50.5 mg, 0.4 mmol) using the experimental conditions of example 24.

AS172 was obtained (232 mg, 74%) as a brown solid.

$^{1}$H NMR (400 MHz, CDCl$_{3}$) δ 7.77 (s, 4H), 7.60 (s, 2H), 7.31 (d, J=2.1 Hz, 2H), 6.90 (dd, J=8.2, 2.1 Hz, 2H), 6.74 (d, J=8.2 Hz, 2H), 4.53 (t, J=6.5 Hz, 4H), 3.98 (t, J=5.9 Hz, 4H), 3.12 (t, J=6.5 Hz, 4H), 2.45 (t, J=6.9 Hz, 4H), 2.21 (s, 12H), 2.01-1.84 (m, 4H).

$^{13}$C NMR (100 MHz, CDCl$_{3}$) δ 154.4 (2C), 147.1 (2C), 133.3 (2C), 130.4 (2C), 130.3 (2C), 128.8 (2C), 126.1 (4C), 120.2 (2C), 113.4 (2C), 112.3 (2C), 67.4 (2C), 56.2 (2C), 51.6 (2C), 45.50 (4C), 35.5 (2C), 27.3 (2C).

Example 48

Synthesis of 3-(4-(2-(4-(((1-(4-(3-(dimethylamino)propoxy)-3-bromophenethyl)-1H-1,2,3-triazol-4-yl)methoxy)methyl)-1H-1,2,3-triazol-1-yl)ethyl)-2-bromophenoxy)-N,N-dimethylpropan-1-amine (AS173)

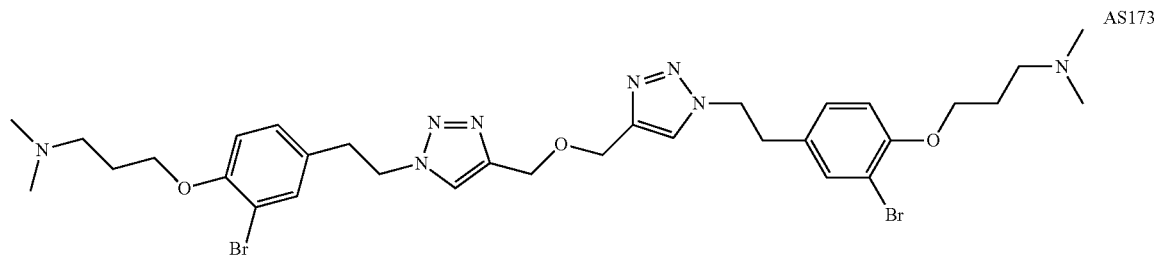

AS173 was obtained from azide 3b (340.3 mg, 1.04 mmol) and propargyl ether (37.6 mg, 0.4 mmol) using the experimental conditions of example 24.

AS173 was obtained (256 mg, 85%) as a brown solid.

$^1$H NMR (400 MHz, CDCl$_3$) δ 7.30 (s, 2H), 7.14 (d, J=2.1 Hz, 2H), 6.80 (dd, J=8.4, 2.1 Hz, 2H), 6.66 (d, J=8.4 Hz, 2H), 4.47 (s, 4H), 4.38 (t, J=7.2 Hz, 4H), 3.88 (t, J=6.3 Hz, 4H), 2.96 (t, J=7.2 Hz, 4H), 2.34 (t, J=7.2 Hz, 4H), 2.10 (s, 12H), 1.86-1.78 (m, 4H).

$^{13}$C NMR (100 MHz, CDCl$_3$) δ 154.1 (2C), 144.0 (2C), 133.0 (2C), 130.2 (2C), 128.5 (2C), 123.1 (2C), 113.1 (2C), 111.9 (2C), 67.1 (2C), 62.9 (2C), 55.9 (2C), 51.2 (2C), 45.22 (4C), 35.1 (2C), 27.0 (2C).

Example 49

Synthesis of bis-triazole AS174

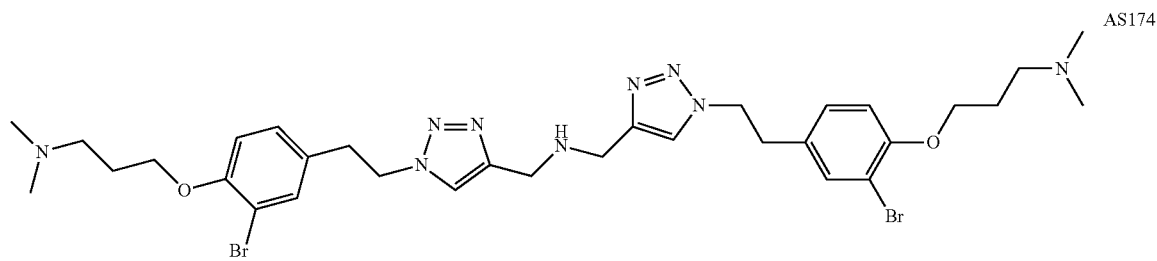

AS174 was obtained from azide 3b (340.3 mg, 1.04 mmol) and dipropargylamine (37.2 mg, 0.4 mmol) using the experimental conditions of example 24.

AS174 was obtained (237 mg, 79%) as a brown solid.

$^1$H NMR (400 MHz, CDCl$_3$) δ 7.25 (s, 2H), 7.15 (d, J=1.8 Hz, 2H), 6.83 (dd, J=8.4, 1.8 Hz, 2H), 6.68 (d, J=8.4 Hz, 2H), 4.41 (t, J=7.0 Hz, 4H), 3.91 (t, J=6.0 Hz, 4H), 3.73 (br, 4H), 3.00 (t, J=7.0 Hz, 4H), 2.54 (d, J=7.5 Hz, 4H), 2.25 (s, 12H), 1.97-1.88 (m, 4H).

$^{13}$C NMR (100 MHz, CDCl$_3$) δ 154.0 (2C), 145.5 (2C), 133.1 (2C), 130.5 (2C), 128.6 (2C), 122.4 (2C), 113.2 (2C), 112.0 (2C), 66.9, 55.5 (2C), 51.2 (2C), 44.4 (4C), 43.1 (2C), 35.3 (2C), 26.3 (2C).

Example 50

Synthesis of 1-(3-bromo-4-methoxybenzyl)-4-(4-(1-(3-bromo-4-methoxybenzyl)-1H-1,2,3-triazol-4-yl)phenyl)-1H-1,2,3-triazole (SA8)

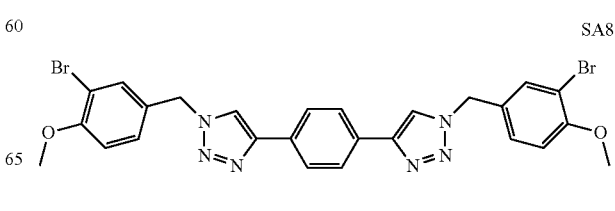

SA8 was obtained from azide 2e (252 mg, 1.04 mmol) and 1,4-diethynylbenzene (50.5 mg, 0.4 mmol) using the experimental conditions of example 24.

SA8 was obtained (171 mg, 70%) as a yellow solid.

$^1$H NMR (400 MHz, DMSO) δ 8.66 (s, 2H), 7.91 (s, 4H), 7.66 (d, J=2.2 Hz, 2H), 7.39 (dd, J=8.5, 2.2 Hz, 2H), 7.13 (d, J=8.5 Hz, 2H), 5.58 (s, 4H), 3.83 (s, 6H).

$^{13}$C NMR (100 MHz, DMSO) δ 155.3 (2C), 146.3 (2C), 132.8 (2C), 130.1 (2C), 129.5 (2C), 129.1 (2C), 125.6 (4C), 121.5 (2C), 112.9 (2C), 110.6 (2C), 56.3 (2C), 51.8 (2C).

Example 51

Synthesis of 2-(4-(2-(4-(4-(1-(4-(2-(dimethylamino)ethoxy)phenethyl)-1H-1,2,3-triazol-4-yl)phenyl)-1H-1,2,3-triazol-1-yl)ethyl)phenoxy)-N,N-dimethylethanamine (SA11)

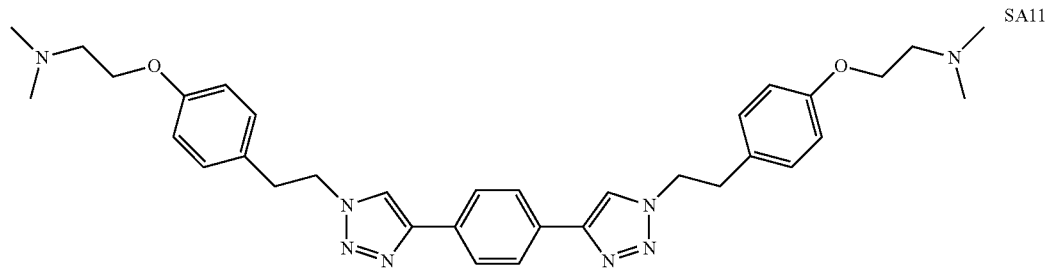

SA11 was obtained from azide 3d (243.4 mg, 1.04 mmol) and 1,4-diethynylbenzene (50.5 mg, 0.4 mmol) using the experimental conditions of example 24.

SA11 was obtained (166 mg, 70%) as a yellow solid.

$^1$H NMR (400 MHz, CDCl$_3$) δ 7.81 (s, 4H), 7.51 (s, 2H), 7.02 (d, J=8.6 Hz, 4H), 6.84 (d, J=8.6 Hz, 4H), 4.59 (t, J=7.2 Hz, 4H), 4.03 (t, J=5.7 Hz, 4H), 3.18 (t, J=7.2 Hz, 4H), 2.72 (t, J=5.7 Hz, 4H), 2.33 (s, 12H).

$^{13}$C NMR (100 MHz, CDCl$_3$) δ 158.1 (2C), 147.2 (2C), 130.6 (2C), 129.8 (4C), 129.2 (2C), 126.2 (4C), 120.1 (2C), 115.0 (4C), 66.1 (2C), 58.3 (2C), 52.1 (2C), 45.9 (4C), 36.1 (2C).

Example 52

Synthesis of 3-(4-(2-(4-(4-(1-(4-(3-(dimethylamino)propoxy)phenethyl)-1H-1,2,3-triazol-4-yl)phenyl)-1H-1,2,3-triazol-1-yl)ethyl)phenoxy)-N,N-dimethylpropan-1-amine (SA12)

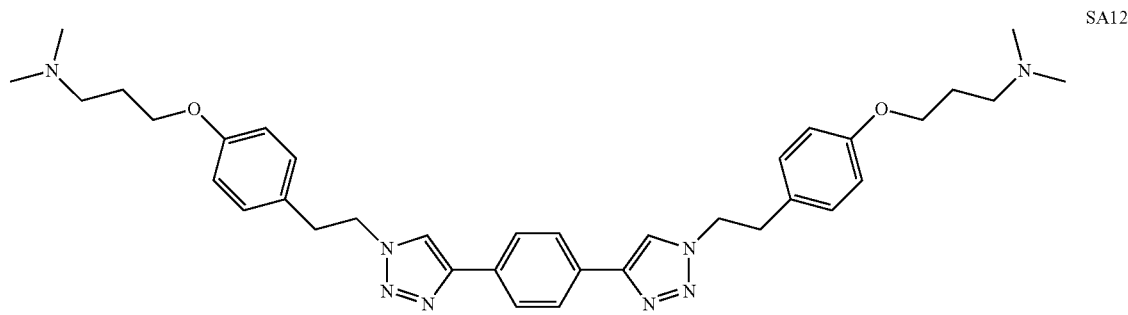

SA12 was obtained from azide 3e (257.9 mg, 1.04 mmol) and 1,4-diethynylbenzene (50.5 mg, 0.4 mmol) using the experimental conditions of example 24.

SA12 was obtained (124 mg, 50%) as a yellow solid.

$^1$H NMR (400 MHz, DMSO) δ 8.57 (s, 2H), 7.88 (s, 4H), 7.13 (d, J=8.6 Hz, 4H), 6.84 (d, J=8.6 Hz, 4H), 4.62 (t, J=7.2 Hz, 4H), 3.97 (t, J=6.1 Hz, 4H), 3.16 (t, J=7.1 Hz, 4H), 2.92-2.81 (m, 4H), 2.53 (s, 12H), 2.04-1.94 (m, 4H).

$^{13}$C NMR (100 MHz, DMSO) δ 157.7 (2C), 146.3 (2C), 130.7 (2C), 130.3 (4C), 130.2 (2C), 126.1 (4C), 121.9 (2C), 115.0 (4C), 65.6 (2C), 55.2 (2C), 51.4 (2C), 43.7 (4C), 35.2 (2C), 25.5 (2C).

Example 53

Synthesis of 2-(4-(3-(4-(4-(1-(3-(4-(2-(dimethylamino)ethoxy)-3-bromophenyl)propyl)-1H-1,2,3-triazol-4-yl)phenyl)-1H-1,2,3-triazol-1-yl)propyl)-2-bromophenoxy)-N,N-dimethylethanamine (SA31)

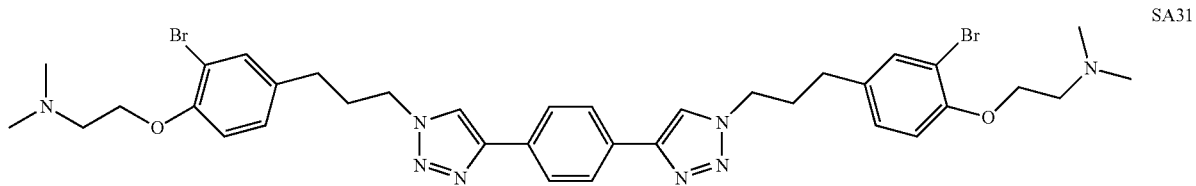

SA31 was obtained from azide 3l (340 mg, 1.04 mmol) and 1,4-diethynylbenzene (50.5 mg, 0.4 mmol) using the experimental conditions of example 24.

SA31 was obtained (215 mg, 69%) as a yellow solid.

$^1$H NMR (400 MHz, CDCl$_3$) δ 7.83 (s, 4H), 7.76 (s, 2H), 7.31 (d, J=2.1 Hz, 2H), 7.00 (dd, J=8.4, 2.1 Hz, 2H), 6.76 (d, J=8.4 Hz, 2H), 4.34 (t, J=7.0 Hz, 4H), 4.04 (t, J=5.8 Hz, 4H), 2.74 (t, J=5.8 Hz, 4H), 2.55 (t, J=7.4 Hz, 4H), 2.32 (s, 12H), 2.25-2.13 (m, 4H).

$^{13}$C NMR (100 MHz, CDCl$_3$) δ 153.8 (2C), 147.3 (2C), 133.9 (2C), 133.1 (2C), 130.3 (2C), 128.4 (2C), 126.1 (4C), 119.8 (2C), 113.4 (2C), 112.2 (2C), 67.9 (2C), 57.9 (2C), 49.5 (2C), 46.1 (4C), 31.6 (2C), 31.3 (2C).

Example 54

Synthesis of 3-(4-(3-(4-(4-(1-(3-(4-(3-(dimethylamino)propoxy)-3-bromophenyl)propyl)-1H-1,2,3-triazol-4-yl)phenyl)-1H-1,2,3-triazol-1-yl)propyl)-2-bromophenoxy)-N,N-dimethylpropan-1-amine (SA32)

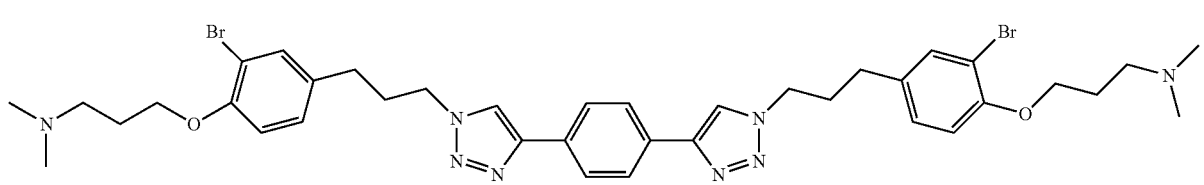

SA32 was obtained from azide 3m (354 mg, 1.04 mmol) and 1,4-diethynylbenzene (50.5 mg, 0.4 mmol) using the experimental conditions of example 24.

SA32 was obtained (203 mg, 63%) as a yellow solid.

$^1$H NMR (400 MHz, CDCl$_3$) δ 7.83 (s, 4H), 7.76 (s, 2H), 7.31 (d, J=1.6 Hz, 2H), 6.99 (dd, J=8.4, 1.6 Hz, 2H), 6.77 (d, J=8.4 Hz, 2H), 4.34 (t, J=7.2 Hz, 4H), 3.98 (t, J=6.2 Hz, 4H), 2.55 (t, J=7.2 Hz, 4H), 2.46 (t, J=7.2 Hz, 4H), 2.28-2.13 (m, 16H), 2.01-1.87 (m, 4H).

$^{13}$C NMR (100 MHz, CDCl$_3$) δ 153.9 (2C), 147.3 (2C), 133.7 (2C), 133.0 (2C), 130.3 (2C), 128.4 (2C), 126.1 (4C), 119.8 (2C), 113.5 (2C), 112.2 (2C), 67.4 (2C), 56.2 (2C), 49.5 (2C), 45.4 (4C), 31.6 (2C), 31.3 (2C), 27.3 (2C).

Example 55

Synthesis of 2-(4-(2-(4-(4-(1-(4-(2-(dimethylamino) ethoxy)-3,5-dibromophenethyl)-1H-1,2,3-triazol-4-yl)phenyl)-1H-1,2,3-triazol-1-yl)ethyl)-2,6-dibromophenoxy)-N,N-dimethylethanamine (SA33)

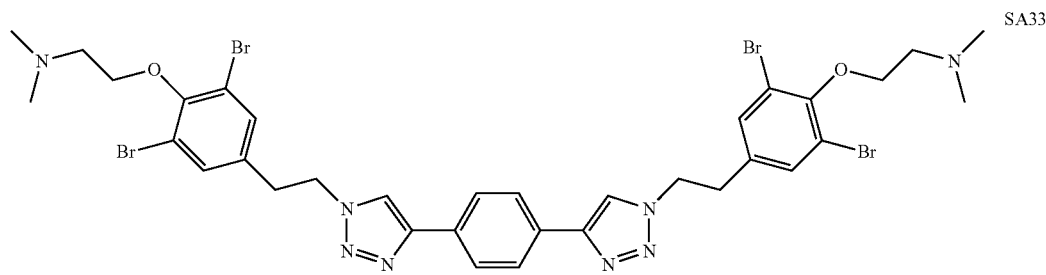

SA33 was obtained from azide 3f (408 mg, 1.04 mmol) and 1,4-diethynylbenzene (50.5 mg, 0.4 mmol) using the experimental conditions of example 24.

SA33 was obtained (237 mg, 65%) as a yellow solid.

$^1$H NMR (400 MHz, CDCl$_3$) δ 7.83 (s, 4H), 7.62 (s, 2H), 7.29 (s, 4H), 4.60 (t, J=7.3 Hz, 4H), 4.07 (t, J=5.8 Hz, 4H), 3.19 (t, J=7.3 Hz, 4H), 2.80 (t, J=5.8 Hz, 4H), 2.36 (s, 12H).

$^{13}$C NMR (100 MHz, CDCl$_3$) δ 152.5 (2C), 147.4 (2C), 135.6 (2C), 132.9 (4C), 130.3 (2C), 126.2 (4C), 120.3 (2C), 118.6 (4C), 70.9 (2C), 58.8 (2C), 51.1 (2C), 45.9 (4C), 35.4 (2C).

Example 56

Synthesis of 3-(4-(2-(4-(4-(1-(4-(3-(dimethylamino) propoxy)-3,5-dibromophenethyl)-1H-1,2,3-triazol-4-yl)phenyl)-1H-1,2,3-triazol-1-yl)ethyl)-2,6-dibromophenoxy)-N,N-dimethylpropan-1-amine (SA34)

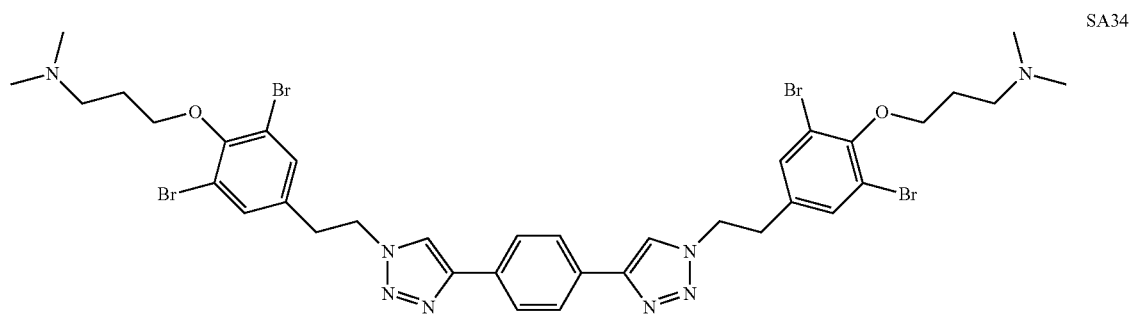

SA34 was obtained from azide 3g (422 mg, 1.04 mmol) and 1,4-diethynylbenzene (50.5 mg, 0.4 mmol) using the experimental conditions of example 24.

SA34 was obtained (274 mg, 73%) as a brown solid.

$^1$H NMR (400 MHz, CDCl$_3$) δ 7.84 (s, 4H), 7.62 (s, 2H), 7.26 (s, 4H), 4.59 (t, J=7.3 Hz, 4H), 4.03 (t, J=6.4 Hz, 4H), 3.19 (t, J=7.3 Hz, 4H), 2.54 (t, 6.4 Hz, 4H), 2.77 (s, 12H), 2.08-1.97 (m, 4H).

$^{13}$C NMR (100 MHz, CDCl$_3$) δ 152.5 (2C), 147.3 (2C), 135.5 (2C), 132.9 (4C), 130.3 (2C), 126.2 (4C), 120.3 (2C), 118.6 (4C), 72.1 (2C), 56.3 (2C), 51.2 (2C), 45.6 (4C), 35.4 (2C), 28.3 (2C).

Example 57

Synthesis of 1,4 bis (1-(3-iodo-4-hydroxyphenethyl)-1H-1,2,3-triazol-4-yl) benzene (SA43)

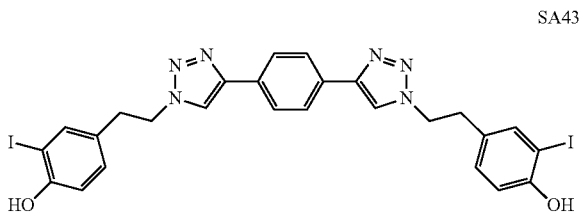 [SMILES: Oc1ccc(CCn2cc(-c3ccc(-c4cn(CCc5ccc(O)c(I)c5)nn4)cc3)nn2)cc1I]

SA43 was obtained from azide 2h (301 mg, 1.04 mmol) and 1,4-diethynylbenzene (50.5 mg, 0.4 mmol) using the experimental conditions of example 24.

SA43 was obtained (135 mg, 48%) as a yellow solid.

$^1$H NMR (400 MHz, DMSO) δ 8.55 (s, 2H), 7.88 (s, 4H), 7.51 (d, J=1.9 Hz, 2H), 6.97 (dd, J=7.9, 1.9 Hz, 2H), 6.78 (d, J=7.9 Hz, 2H), 4.57 (t, J=6.8 Hz, 4H), 3.07 (t, J=6.8 Hz, 4H).

$^{13}$C NMR (100 MHz, DMSO) δ 156.5 (2C), 145.8 (2C), 138.6 (2C), 130.2 (2C), 129.7 (2C), 129.0 (2C), 125.6 (4C), 121.5 (2C), 115.1 (2C), 85.3 (2C), 50.9 (2C), 34.2 (2C).

Example 58

Synthesis of 2-(4-(2-(4-(4-(1-(4-(2-(dimethylamino)ethoxy)-3-iodophenethyl)-1H-1,2,3-triazol-4-yl)phenyl)-1H-1,2,3-triazol-1-yl)ethyl)-2-iodophenoxy)-N,N-dimethylethanamine (SA45)

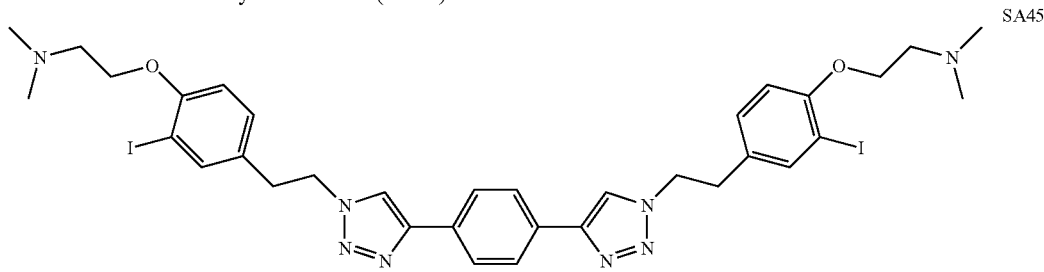

SA45 was obtained from azide 3j (374 mg, 1.04 mmol) and 1,4-diethynylbenzene (50.5 mg, 0.4 mmol) using the experimental conditions of example 24.

SA45 was obtained (230 mg, 68%) as a yellow solid.

$^1$H NMR (400 MHz, CDCl$_3$) δ 7.79 (s, 4H), 7.58 (s, 2H), 7.56 (d, J=2.1 Hz, 2H), 6.96 (dd, J=8.4, 2.1 Hz, 2H), 6.67 (d, J=8.4 Hz, 2H), 4.54 (t, J=7.2 Hz, 4H), 4.04 (t, J=5.8 Hz, 4H), 3.12 (t, J=7.2 Hz, 4H), 2.77 (t, J=5.8 Hz, 4H), 2.34 (s, 12H).

$^{13}$C NMR (100 MHz, CDCl$_3$) δ 156.7 (2C), 147.2 (2C), 139.6 (2C), 131.3 (2C), 130.3 (2C), 129.9 (2C), 126.2 (4C), 120.2 (2C), 112.2 (2C), 86.9 (2C), 68.2 (2C), 58.0 (2C), 51.7 (2C), 46.3 (4C), 35.4 (2C).

Example 59

Synthesis of 3-(4-(2-(4-(4-(1-(4-(3-(dimethylamino)propoxy)-3-iodophenethyl)-1H-1,2,3-triazol-4-yl)phenyl)-1H-1,2,3-triazol-1-yl)ethyl)-2-iodophenoxy)-N,N-dimethylpropan-1-amine (SA46)

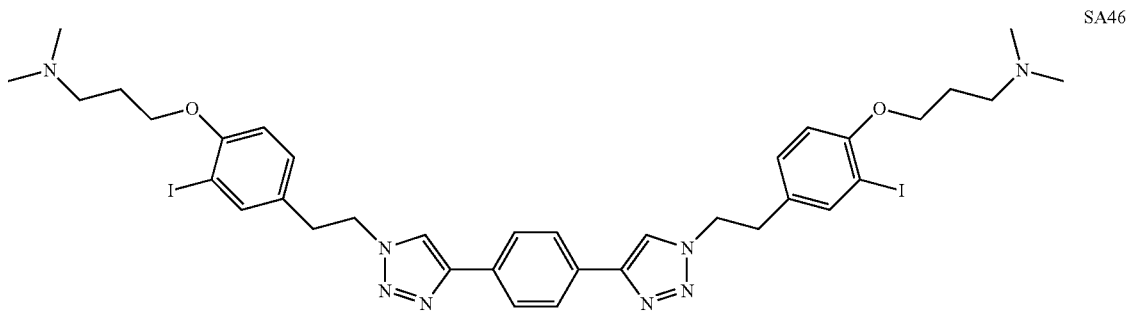

SA46 was obtained from azide 3k (384 mg, 1.04 mmol) and 1,4-diethynylbenzene (50.5 mg, 0.4 mmol) using the experimental conditions of example 24.

SA46 was obtained (185 mg, 53%) as a brown solid.

$^1$H NMR (400 MHz, CDCl$_3$) δ 7.79 (s, 4H), 7.59 (s, 2H), 7.54 (d, J=1.4 Hz, 2H), 6.99-6.90 (dd, J=8.4, 1.4 Hz, 2H), 6.65 (d, J=8.4 Hz, 2H), 4.54 (t, J=7.1 Hz, 4H), 3.99 (t, J=5.9 Hz, 4H), 3.12 (t, J=7.1 Hz, 4H), 2.75-2.64 (m, 4H), 2.35 (s, 12H), 2.09-1.96 (m, 4H).

$^{13}$C NMR (100 MHz, CDCl$_3$) δ 156.5 (2C), 147.2 (2C), 139.5 (2C), 131.3 (2C), 130.3 (2C), 129.9 (2C), 126.2 (4C), 120.2 (2C), 112.2 (2C), 86.9 (2C), 67.2 (2C), 55.9 (2C), 51.7 (2C), 44.5 (4C), 35.4 (2C), 26.4 (2C).

Example 60

Synthesis of 2-(4-(2-(4-(4-(1-(4-(2-(dimethylamino)ethoxy)-3-chlorophenethyl)-1H-1,2,3-triazol-4-yl)phenyl)-1H-1,2,3-triazol-1-yl)ethyl)-2-chlorophenoxy)-N,N-dimethylethanamine (SA63)

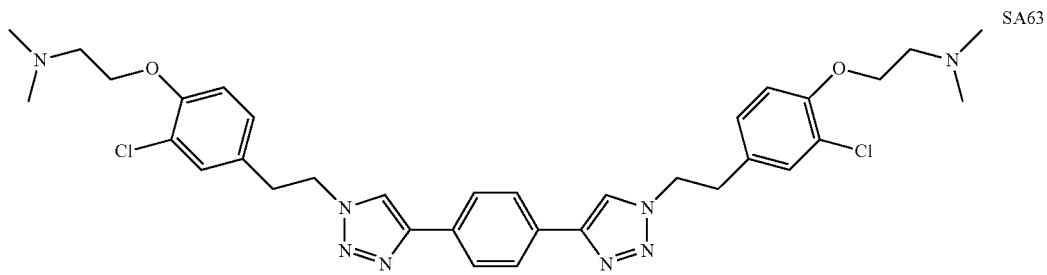

SA63 was obtained from azide 3h (284 mg, 1.04 mmol) and 1,4-diethynylbenzene (50.5 mg, 0.4 mmol) using the experimental conditions of example 24.

SA63 was obtained (178 mg, 67%) as a yellow solid.

$^{1}$H NMR (400 MHz, CDCl$_3$) δ 7.79 (s, 4H), 7.59 (s, 2H), 7.16 (d, J=1.8 Hz, 2H), 6.88 (dd, J=8.4, 1.8 Hz, 2H), 6.79 (d, J=8.4 Hz, 2H), 4.56 (t, J=7.2 Hz, 4H), 4.07 (t, J=5.7 Hz, 4H), 3.15 (t, J=7.2 Hz, 4H), 2.77 (t, J=5.7 Hz, 4H), 2.35 (s, 12H).

$^{13}$C NMR (101 MHz, CDCl$_3$) δ 153.5 (2C), 147.2 (2C), 130.4 (4C), 130.3 (2C), 128.1 (2C), 126.2 (4C), 123.2 (2C), 120.2 (2C), 113.7 (2C), 67.7 (2C), 57.9 (2C), 51.7 (2C), 46.1 (4C), 35.7 (2C).

Example 61

Synthesis of 3-(4-(2-(4-(4-(1-(4-(3-(dimethylamino)propoxy)-3-chlorophenethyl)-1H-1,2,3-triazol-4-yl)phenyl)-1H-1,2,3-triazol-1-yl)ethyl)-2-chlorophenoxy)-N,N-dimethylpropan-1-amine (SA64)

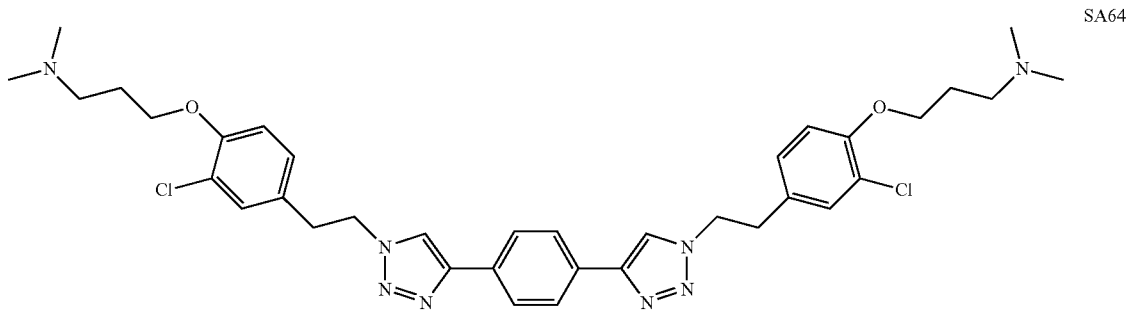

SA64 was obtained from azide 3i (293 mg, 1.04 mmol) and 1,4-diethynylbenzene (50.5 mg, 0.4 mmol) using the experimental conditions of example 24.

SA64 was obtained (116 mg, 42%) as a yellow solid.

$^{1}$H NMR (400 MHz, CDCl$_3$) δ 7.83 (s, 4H), 7.56 (s, 2H), 7.18 (d, J=2.1 Hz, 2H), 6.90 (dd, J=8.4, 2.1 Hz, 2H), 6.82 (d, J=8.4 Hz, 2H), 4.59 (t, J=7.2 Hz, 4H), 4.05 (t, J=6.2 Hz, 4H), 3.18 (t, J=7.2 Hz, 4H), 2.62 (d, J=6.2 Hz, 4H), 2.34 (s, 12H), 2.10-1.97 (m, 4H).

$^{13}$C NMR (101 MHz, CDCl$_3$) δ 153.6 (2C), 147.3 (2C), 130.5 (2C), 130.4 (2C), 130.2 (2C), 128.2 (2C), 126.3 (4C), 123.3 (2C), 120.2 (2C), 113.8 (2C), 67.3 (2C), 56.1 (2C), 51.8 (2C), 45.1 (4C), 35.8 (2C), 26.9 (2C).

Example 62

Synthesis of 2-(4-(4-(4-(1-(4-(2-(dimethylamino) ethoxy)phenyl)-1H-1,2,3-triazol-4-yl)phenyl)-1H-1, 2,3-triazol-1-yl)phenoxy)-N,N-dimethylethanamine (SA61)

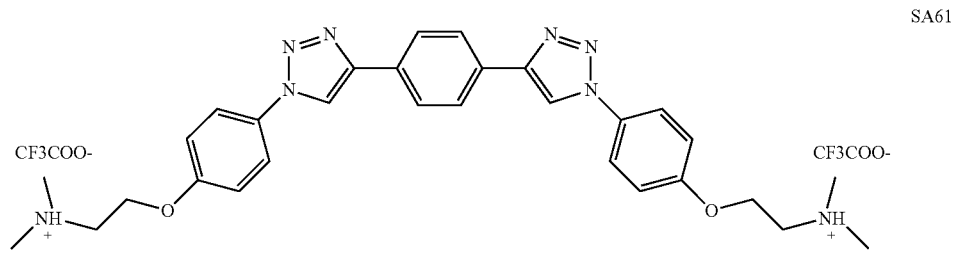

SA61 was obtained from azide 3n (214 mg, 1.04 mmol) and 1,4-diethynylbenzene (50.5 mg, 0.4 mmol) using the experimental conditions of example 24. Then, the product was dissolved in TFA (0.5 mL), precipitated in ether and washed with ether to yield bis-triazole SA61 (227 mg, 74%) as a white solid.

$^1$H NMR (400 MHz, DMSO) δ 10.26 (brs, 2H, NH), 9.29 (s, 2H), 8.07 (s, 4H), 7.90-7.93 (m, 4H), 7.23-7.26 (m, 4H), 4.43 (t, J=5.0 Hz, 4H), 3.69-3.44 (m, 4H), 2.91 (s, 12H).

$^{13}$C NMR (101 MHz, DMSO) δ 157.6 (2C), 146.9 (2C), 130.8 (2C), 130.1 (2C), 125.9 (4C), 121.7 (4C), 119.8 (2C), 115.8 (4C), 62.7 (2C), 55.4 (2C), 42.85 (4C).

Example 63

Synthesis of 3-(4-(4-(4-(1-(4-(3-(dimethylamino) propoxy)-3-bromophenyl)-1H-1,2,3-triazol-4-yl) phenyl)-1H-1,2,3-triazol-1-yl)-2-bromophenoxy)-N, N-dimethylpropan-1-amine (SA66)

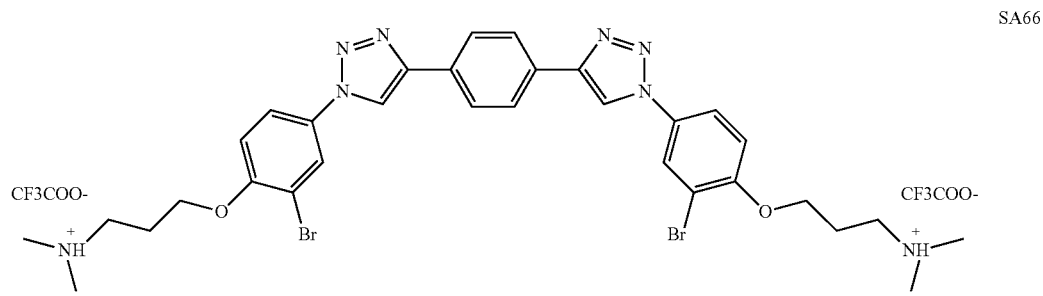

A first bis-triazole compound was obtained from azide 3o (229 mg, 1.04 mmol) and 1,4-diethynylbenzene (50.5 mg, 0.4 mmol) using the experimental conditions of example 24.

Said bis-triazole compound (79.5 mg, 0.1 mmol) was then diluted in CH$_2$Cl$_2$/TFA (1 mL/1 mL) and bromine (Br$_2$) (64 mg, 0.4 mmol) in CH$_2$Cl$_2$ (1 mL) was added dropwise. The mixture was stirred at room temperature for 12 h. Then, the product was precipitated in ether and washed with ether to yield Bis-triazole SA66 (78 mg, 82%) as a white solid.

$^1$H NMR (400 MHz, DMSO) δ 9.54 (brs, NH, 2H), 9.37 (s, 2H), 8.23 (d, J=2.6 Hz, 2H), 8.05 (s, 4H), 7.98 (dd, J=8.9, 2.6 Hz, 2H), 7.38 (d, J=8.9 Hz, 2H), 4.25 (t, J=6.0 Hz, 4H), 3.35-3.22 (m, 4H), 2.86 (d, J=5 Hz, 12H) 2.33-2.04 (m, 4H).

$^{13}$C NMR (100 MHz, DMSO) δ 154.6 (2C), 146.9 (2C), 130.7 (2C), 130.0 (2C), 125.9 (4C), 124.5 (2C), 120.7 (2C), 120.0 (2C), 114.5 (2C), 111.7 (2C), 66.6 (2C), 54.3 (2C), 42.4 (4C), 23.8 (2C).

Example 64

Anti-Biofilm Properties of Compounds According to the Invention

Table 1 below gives the amount of five different marine bacterial strains (TC14, TC8, 4M6, TC5 and TC11) that adhere on a microtiter plate in the presence of a compound of the invention at a 200 micromolar concentration according to the Anti-adhesion test method disclosed herein.

TABLE 1

| | | % of adhesion at 200 μM | | | | |
|---|---|---|---|---|---|---|
| cpd | yield | TC14 | TC8 | 4M6 | TC5 | TC11 |
| nt3 | 96% | 53.3 ± 6.3 | 56.9 ± 1.7 | 50.9 ± 0.3 | | |
| nt6 | 93% | 38.4 ± 7.4 | 42.7 ± 6.5 | 44.9 ± 3.1 | | |
| nt7 | 88% | 37.4 ± 0.1 | 48.2 ± 2.1 | 46.3 ± 2.7 | | |
| nt10 | 91% | 50.4 ± 2.2 | 50.0 ± 4.9 | 49.2 ± 0.8 | | |
| nt21 | 92% | 53.0 ± 4.0 | 63. ± 8.1 | 83.4 ± 3.9 | | |
| nt22 | 87% | 54.4 ± 1.7 | 85.6 ± 2.1 | 52.4 ± 2.3 | | |
| nt23 | 80% | 31.0 ± 6.1 | 58.3 ± 8.7 | 31.8 ± 3.5 | | |
| nt24 | 77% | 56.7 ± 1.3 | 66.51 ± 11.59 | 61.5 ± 4.2 | | |
| nt26 | 87% | 40.2 ± 3.3 | 50.34 ± 5.79 | 47.8 ± 0.1 | | |
| nt27 | 63% | 29.3 ± 7.5 | 28.9 ± 17.0 | 27.8 ± 16.3 | | |
| as158 | 93% | 55.8 ± 3.8 | 57.0 ± 2.2 | 51.5 ± 3.0 | | |
| as159 | 94% | 61.5 ± 1.0 | 58.4 ± 4.3 | 57.4 ± 1.6 | | |
| as160 | 89% | 67.4 ± 4.0 | 54.3 ± 10.8 | 59.5 ± 2.2 | | |
| as162 | 88% | 0 ± 5.3 | 14. ± 11.8 | 10.9 ± 8.1 | 21.5 ± 6.6 | 4.3 ± 7.5 |
| as163 | 98% | 34.8 ± 2.7 | 34.6 ± 5.1 | 40.4 ± 7.8 | | |
| as164 | 84% | 40.8 ± 5.0 | 47.1 ± 1.0 | 51.7 ± 4.3 | | |
| as168 | 89% | 53.8 ± 5.9 | 59.9 ± 6.4 | 77.1 ± 2.4 | | |
| as172 | 74% | 0.5 ± 0.8 | 5.3 ± 2.5 | 5.1 ± 1.4 | 12.67 ± 5.7 | 4.6 ± 0.4 |
| as173 | 85% | 41.7 ± 1.6 | 51.6 ± 1. | 53.7 ± 4.0 | | |
| as174 | 79% | 45.0 ± 0.8 | 55.4 ± 0.4 | 56.3 ± 2.4 | | |
| SA8 | 70% | 23.3 ± 3.8 | 24.1 ± 2.6 | 33.1 ± 4.4 | 38.3 ± 0.1 | 16.4 ± 8.0 |
| SA12 | 50% | 42.4 ± 8.6 | 30.0 ± 21.9 | 14.3 ± 7.3 | 66.2 ± 2.8 | 41.0 ± 4.1 |
| SA32 | 63% | 34.3 ± 2.6 | 17.7 ± 11.1 | 26.7 ± 5.6 | 53.4 ± 13.8 | 17.4 ± 2.9 |
| SA33 | 65% | 6.3 ± 1.3 | 6.8 ± 4.3 | 7.4 ± 8.3 | 0.7 ± 0.7 | 4.4 ± 2.7 |
| SA34 | 73% | 13.0 ± 7.7 | 10.2 ± 3.1 | 8.2 ± 3.5 | 7.9 ± 7.3 | 7.0 ± 3.12 |
| SA43 | 48% | 6.8 ± 1.2 | 10.5 ± 12.0 | 13.6 ± 8.9 | 23.8 ± 0.1 | 4.6 ± 0.1 |
| SA45 | 68% | 42.1 ± 2.9 | 30.0 ± 16.3 | 3.2 ± 4.6 | 37.5 ± 13.3 | 9.3 ± 0.5 |
| SA46 | 53% | 30.2 ± 3.5 | 17.4 ± 14.3 | 26.6 ± 3.4 | 22.4 ± 14.7 | 5.8 ± 1.2 |
| SA61 | 74% | 47.8 ± 1.7 | 45.6 ± 1.2 | 40.2 ± 0.3 | 89.4 ± 0.8 | 19.3 ± 16.9 |
| SA63 | 67% | 30.6 ± 5.3 | 29.0 ± 3.2 | 43.6 ± 3.3 | 37.3 ± 6.0 | 37.0 ± 1.0 |
| SA64 | 42% | 28.4 ± 14.0 | 20.2 ± 21.1 | 31.0 ± 12.4 | 42.9 ± 4.5 | 42.6 ± 5.6 |
| SA66 | 82% | 19.0 ± 6.5 | 31.7 ± 2.2 | 24.5 ± 6.9 | 23.3 ± 4.0 | 45.5 ± 1.1 |

At a 200 micromolar concentration, the compounds of the invention are able to inhibit at least 40% of the adhesion of one of the bacterial strains that were tested.

Compounds AS162, AS163, AS172, NT23, NT27, SA33, SA34 and SA43 all inhibit at least 65% of the adhesion of at least two marine bacterial strains.

Compounds AS162, AS172, SA33, SA34 and SA43 all inhibit at least 85% of the adhesion of at least four marine bacterial strains and compounds AS162 and AS172 totally inhibit the adhesion of bacterial strain TC14.

Example 65

Toxicity of Compounds According to the Invention

Table 2 below gives the $EC_{50}$ (effective concentration to inhibit 50% of the adhesion). $LC_{50}$ (necessary concentration to kill 50% of the bacteria), and the selectivity index IS ($LC_{50}/EC_{50}$) of compounds of general formula (I) on five different bacterial strains according to the Toxicity test method disclosed herein. Two comparative examples, using respectively tributyltin oxide (TBTO) and zinc ethane-1.2-diylbis(dithiocarbamate) (ZINEB) are also given.

TABLE 2

| | EC50 (μM) | | | | | LC50 (μM) |
|---|---|---|---|---|---|---|
| Cpd | TC14 | TC8 | 4M6 | TC5 | TC11 | TC14 |
| nt6 | 159.8 ± 33.5 | 180.8 ± 21.3 | 164.1 ± 6.3 | | | — |
| nt7 | 138.4 ± 8.7 | 187.9 ± 3.0 | 194.5 ± 8.0 | | | — |
| nt10 | — | — | 182.4 ± 15.2 | | | — |
| nt23 | 40.9 ± 11.4 | — | 59.9 ± 7.7 | | | — |
| nt26 | 127.1 ± 27.5 | 194.9 ± 10.7 | 198.3 ± 4.1 | | | — |
| nt27 | 59.9 ± 27.2 | 80.3 ± 18.9 | 88.3 ± 46.2 | | | — |
| as162 | 0.97 ± 0.8 | 5.1 ± 1.0 | 5.1 ± 1.04 | 15.5 ± 0.1 | 12.6 ± 5.1 | 257.7 |
| as163 | 91.8 ± 17.9 | 101.6 ± 46.2 | 146.2 ± 81.9 | | | — |
| as164 | 126.2 ± 21.5 | 176.5 ± 3 | — | | | — |
| as172 | 0.39 ± 0.28 | 15.0 ± 3.3 | 3.6 ± 3.8 | 11.0 ± 0.3 | 15.6 ± 2.9 | 224.7 |
| as173 | 121.7 ± 59.1 | — | — | | | — |
| as174 | — | 185.2 ± 16.2 | — | | | — |
| TBTO | — | 7.0 ± 3.0 | 4.0 ± 3.0 | | | — |
| ZINEB | — | 47.0 ± 24.0 | 23.0 ± 1 | | | — |
| SA8 | 99.5 ± 4.5 | 158.6 ± 28.5 | 162.7 ± 23.6 | 151.6 ± 6.7 | 122.6 ± 7.1 | |
| SA12 | 186.9 ± 16.5 | 177.2 ± 80.1 | 73.2 ± 10.7 | | 172.9 ± 22.4 | |
| SA32 | 115.3 ± 20.5 | 109.3 ± 37.2 | 3.1 ± 8.6 | 114.0 ± 28.6 | 61.1 ± 18.5 | |
| SA33 | 20.4 ± 1.2 | 42.5 ± 16.9 | 11.3 ± 9.1 | 19.2 ± 2.1 | 32.0 ± 8.1 | 254.1 |
| SA34 | 13.1 ± 1.0 | 50.5 ± 10.9 | 1.5 ± 2.1 | 4.6 ± 6.3 | 27.2 ± 0.5 | 132 |

TABLE 2-continued

| | | | | | | | |
|---|---|---|---|---|---|---|---|
| SA43 | 20.7 ± 5.2 | 30.3 ± 31.3 | 53.8 ± 50.9 | 58.0 ± 1.61 | 1.1 ± 0.6 | | 236.9 |
| SA45 | 175.0 ± 21.2 | 135.1 ± 34.3 | 14.2 ± 3.2 | 146.8 ± 32.4 | 129.4 ± 13.2 | | |
| SA46 | 74.4 ± 8.3 | 71.5 ± 4.1 | 48.3 ± 48.9 | 70.6 ± 8.9 | 22.2 ± 13.6 | | |
| SA61 | 194.2 ± 13.7 | 184.4 ± 0.6 | 178.8 ± 44.9 | | 139.9 ± 63.5 | | |
| SA63 | 121.7 ± 10.7 | 138.4 ± 10.6 | 96.6 ± 36.2 | 132.7 ± 9.2 | 135.5 ± 5.1 | | |
| SA64 | 146.6 ± 14.4 | 121.3 ± 76.8 | 43.3 ± 14.6 | 150.5 ± 8.1 | 152.5 ± 20.4 | | |
| SA66 | 103.9 ± 4.6 | 140.8 ± 16.5 | 44.2 ± 25.2 | 50.2 ± 10.9 | 164.8 ± 37.8 | | |

| | LC50 (μM) | | | | IS: LC50/EC50 | | | | |
|---|---|---|---|---|---|---|---|---|---|
| Cpd | TC8 | 4M6 | TC5 | TC11 | TC14 | TC8 | 4M6 | TC5 | TC11 |
| nt6 | — | — | | | — | — | — | | |
| nt7 | — | — | | | — | — | — | | |
| nt10 | — | — | | | — | — | — | | |
| nt23 | — | — | | | — | — | — | | |
| nt26 | — | — | | | — | — | — | | |
| nt27 | — | — | | | — | — | — | | |
| as162 | 66.1 | 97.6 | 382 | 334.3 | 265.7 | 12.9 | 19.2 | 24.6 | 26.5 |
| as163 | — | — | | | — | — | — | | |
| as164 | — | — | | | — | — | — | | |
| as172 | 165.1 | 82.3 | 122.2 | 293 | 576.1 | 10.9 | 22.9 | 11.1 | 18.9 |
| as173 | — | — | | | — | — | — | | |
| as174 | — | — | | | — | — | — | | |
| TBTO | 4.8 | 1.1 | | | — | 0.7 | 0.25 | | |
| ZINEB | 61.0 | 31.0 | | | — | 1.3 | 1.3 | | |
| SA8 | | | | | | | | | |
| SA12 | | | | | | | | | |
| SA32 | | | | | | | | | |
| SA33 | 199.3 | 126.4 | 92.64 | 134.8 | 12.45 | 4.7 | 11.2 | 4.8 | 4.2 |
| SA34 | 174.2 | 113.5 | 94.3 | 115.9 | 10.1 | 3.5 | 75.7 | 20.5 | 4.3 |
| SA43 | 270.3 | 351.5 | 320.5 | 88.4 | 11.4 | 8.9 | 6.5 | 5.5 | 80.4 |
| SA45 | | | | | | | | | |
| SA46 | | | | | | | | | |
| SA61 | | | | | | | | | |
| SA63 | | | | | | | | | |
| SA64 | | | | | | | | | |
| SA66 | | | | | | | | | |

Compounds AS162 and AS172 exhibit an $EC_{50}$ comparable to that of TBTO and lower than that of ZINEB. The $LC_{50}$ values show that compounds AS162 and AS172 are less toxic than TBTO and ZINEB. The selectivity index of AS162 and AS172 is higher than 10 thus showing that these compounds are non-toxic and environmentally friendly unlike TBTO and ZINEB.

Compounds SA33, SA34 and SA43 exhibit an $EC_{50}$ comparable to that of ZINEB and the $LC_{50}$ values show that these compounds are less toxic than ZINEB.

Example 66

Anti-Corrosion Properties of Compounds According to the Invention

Electrochemical impedance spectroscopic (EIS) studies have been conducted to investigate corrosion inhibition processes of compounds of the invention according to the Electrochemical impedance spectroscopic test method described herein.

Figure 1:
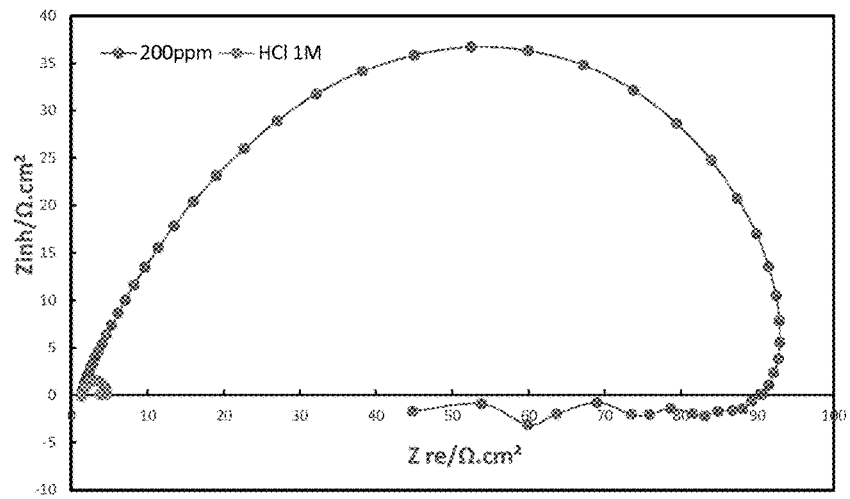
FIG. 1 is a Nyquist diagram for mild steel in 1 N HCl without and with 200 ppm of AS164 according to example 66.

FIG. 1 shows Nyquist plots obtained from AC impedance measurements for mild steel in 1N HCl in the absence and in the presence of AS164 at a concentration of 200 ppm.

The EIS spectra show a depressed capacitive loop in the high frequency range followed by an inductive loop that is observed in the low frequency range. The high frequency capacitive loop can be ascribed to the charge transfer reaction. The low frequency inductive loop may be attributed to the relaxation process obtained by adsorption species like $Cl^-_{ads}$ and $H^+_{ads}$ on the electrode. It may also correspond to the re-dissolution of the passivated surface at low frequencies. The same shape of EIS spectra were obtained both in the blank and in the presence of AS164. This suggests that AS164 does not change the corrosion mechanism.

The diameter of the high frequency loop dramatically increased in the presence of AS164 compounds indicative of a strong corrosion inhibitive effect. The high frequency loop was analyzed in terms of an equivalent circuit involving a parallel combination of $R_{ct}$ and the constant phase element of double layer (CPE). The inhibition efficiency, IE (%), was estimated from the measured $R_{ct}$ values using the following equation:

$$IE\ (\%) = \frac{(R_{ct} - R_{ct}^o)}{R_{ct}} \times 100$$

wherein $R_{ct}^o$ and $R_{ct}$ are the charge-transfer resistance values in the absence and presence of AS164 respectively.

AS164 exhibits an excellent inhibition efficiency (IE %) of around 95%.

Weight loss experiments were done to confirm the corrosion inhibitive properties of AS164. The first trials were performed in a concentration range of 25-200 ppm of AS164 which corresponds to a molar concentration range of $3.5 \cdot 10^{-5}$ M to $2.8 \cdot 10^{-4}$ M. This concentration range was chosen to be comparable with that used in the many reported results corresponding to mild steel exposed in such aggressive acidic corrosion medium in presence of corrosion inhibitive species (see for representative examples AK Singh et al., Corros. Sci. 53 (2011) 1288-97 and Zhang et al., Corros. Sci. 90 (2015) 284-95).

Figure 2:
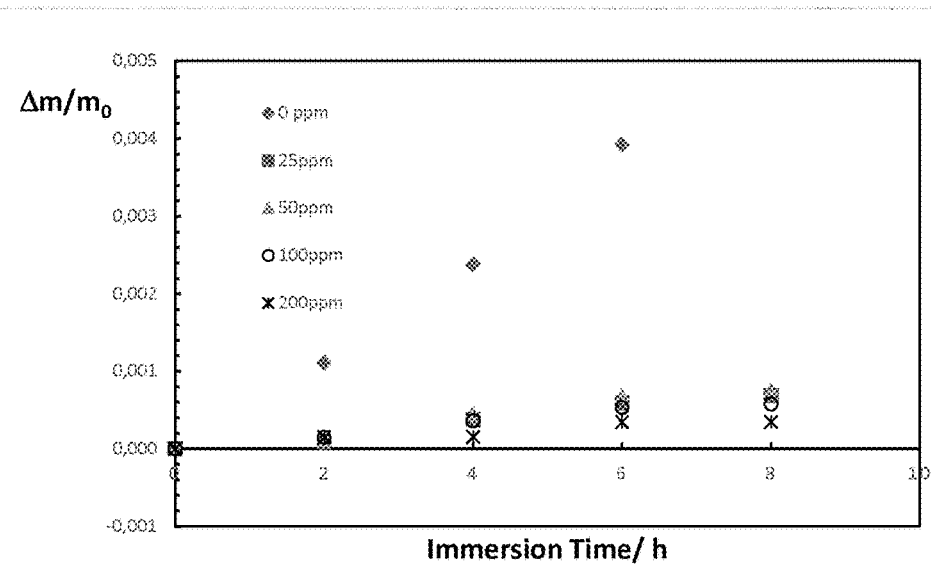
FIG. 2 shows the relative weight loss changes as a function of immersion time diagram for mild steel in 1 N HCl without and with 25, 50, 100 or 200 ppm of AS158 according to example 66.

The relative weight loss change was found to be linearly related to the immersion time as shown in FIG. 2.

The corrosion rate CR, expressed in g cm$^{-2}$ h$^{-1}$, corresponds to the slope of the straight lines shown in FIG. 2. The inhibition efficiency, IE (%), was estimated from the weight loss experiments using the following equation:

$$IE\ (\%) = \frac{(CR^\circ - CR)}{CR^\circ} \times 100$$

wherein $CR^\circ$ and $CR$ are respectively the corrosion rate in the absence and presence of AS164.

The inhibition efficiency of AS164 was found to be greater than 97%.

Inhibition efficiencies were measured for the following compounds according to the invention: AS158, AS159, AS160, AS161, AS162, AS163, AS164, AS168, AS169, AS170, AS171, AS172, AS173, AS174, SA11, SA12, SA31, SA32, SA33, SA34, SA45, SA46, SA61, SA63, SA64 and SA66 in a concentration range of 0.1 to 10 ppm. The results are shown in Table 3 below.

TABLE 3

| Sample | Concentration | IE % |
|---|---|---|
| AS158 | 10 ppm (1.42 · 10$^{-5}$M) | 97.17 |
| | 2 ppm (2.84 · 10$^{-6}$M) | 95.98 |
| | 0.5 ppm (0.71 · 10$^{-6}$M) | 91.72 |
| | 0.3 ppm (0.42 · 10$^{-6}$M) | 87.00 |
| | 0.1 ppm (0.14 · 10$^{-6}$M) | 53.41 |
| AS159 | 10 ppm (1.36 · 10$^{-5}$M) | 97.30 |
| | 2 ppm (2.72 · 10$^{-6}$M) | 95.63 |
| | 0.5 ppm (0.68 · 10$^{-6}$M) | 91.95 |
| | 0.3 ppm (0.41 · 10$^{-6}$M) | 89.62 |
| | 0.1 ppm (0.13 · 10$^{-6}$M) | 39.96 |
| AS160 | 10 ppm (1.31 · 10$^{-5}$M) | 97.03 |
| | 2 ppm (2.62 · 10$^{-6}$M) | 96.06 |
| | 0.5 ppm (0.65 · 10$^{-6}$M) | 92.66 |
| | 0.3 ppm (0.39 · 10$^{-6}$M) | 92.14 |
| | 0.1 ppm (0.13 · 10$^{-6}$M) | 71.40 |
| AS161 | 10 ppm (1.33 · 10$^{-5}$M) | 98.33 |
| | 2 ppm (2.66 · 10$^{-6}$M) | 97.10 |
| | 0.5 ppm (0.66 · 10$^{-6}$M) | 94.07 |
| | 0.3 ppm (0.40 · 10$^{-6}$M) | 86.21 |
| | 0.1 ppm (0.13 · 10$^{-6}$M) | 86.75 |
| AS162 | 10 ppm (1.33 · 10$^{-5}$M) | 97.30 |
| | 2 ppm (2.66 · 10$^{-6}$M) | 97.73 |
| | 0.5 ppm (0.66 · 10$^{-6}$M) | 92.92 |
| | 0.3 ppm (0.40 · 10$^{-6}$M) | 93.35 |
| | 0.1 ppm (0.13 · 10$^{-6}$M) | 48.81 |
| AS163 | 10 ppm (1.38 · 10$^{-5}$M) | 97.07 |
| | 2 ppm (2.77 · 10$^{-6}$M) | 96.52 |
| | 0.5 ppm (0.69 · 10$^{-6}$M) | 94.54 |
| | 0.3 ppm (0.41 · 10$^{-6}$M) | 89.36 |
| | 0.1 ppm (0.13 · 10$^{-6}$M) | 82.24 |
| AS164 | 10 ppm (1.38 · 10$^{-5}$M) | 97.20 |
| | 2 ppm (2.77 · 10$^{-6}$M) | 92.42 |
| | 0.5 ppm (0.69 · 10$^{-6}$M) | 89.20 |
| | 0.3 ppm (0.41 · 10$^{-6}$M) | 90.49 |
| | 0.1 ppm (0.13 · 10$^{-6}$M) | 57.10 |
| AS171 | 10 ppm (1.28 · 10$^{-5}$M) | 98.51 |
| | 2 ppm (2.56 · 10$^{-6}$M) | 97.25 |
| | 0.5 ppm (0.64 · 10$^{-6}$M) | 91.72 |
| | 0.3 ppm (0.38 · 10$^{-6}$M) | 86.91 |
| | 0.1 ppm (0.13 · 10$^{-6}$M) | 53.82 |
| AS172 | 10 ppm (1.28 · 10$^{-5}$M) | 98.15 |
| | 2 ppm (2.56 · 10$^{-6}$M) | 96.44 |
| | 0.5 ppm (0.64 · 10$^{-6}$M) | 91.11 |
| | 0.3 ppm (0.38 · 10$^{-6}$M) | 92.94 |
| | 0.1 ppm (0.13 · 10$^{-6}$M) | 40.16 |
| AS173 | 10 ppm (1.33 · 10$^{-5}$M) | 97.95 |
| | 2 ppm (2.67 · 10$^{-6}$M) | 95.77 |
| | 0.5 ppm (0.67 · 10$^{-6}$M) | 92.47 |
| | 0.3 ppm (0.4 · 10$^{-6}$M) | 86.70 |
| | 0.1 ppm (0.13 · 10$^{-6}$M) | 46.78 |
| AS174 | 10 ppm (1.33 · 10$^{-5}$M) | 97.17 |
| | 2 ppm (2.67 · 10$^{-6}$M) | 95.98 |
| | 0.5 ppm (0.67 · 10$^{-6}$M) | 91.72 |
| | 0.3 ppm (0.4 · 10$^{-6}$M) | 87.00 |
| | 0.1 ppm (0.13 · 10$^{-6}$M) | 53.41 |
| SA11 | 10 ppm (1.68 · 10$^{-5}$M) | 97.11 |
| | 2 ppm (3.36 · 10$^{-6}$M) | 96.95 |
| | 0.5 ppm (0.84 · 10$^{-6}$M) | 95.49 |
| | 0.3 ppm (0.50 · 10$^{-6}$M) | 93.32 |
| | 0.1 ppm (0.17 · 10$^{-6}$M) | 90.50 |
| SA12 | 10 ppm (1.6 · 10$^{-5}$M) | 95.73 |
| | 2 ppm (3.21 · 10$^{-6}$M) | 96.89 |
| | 0.5 ppm (0.80 · 10$^{-6}$M) | 94.65 |
| | 0.3 ppm (0.48 · 10$^{-6}$M) | 69.97 |
| | 0.1 ppm (0.16 · 10$^{-6}$M) | 39.30 |
| SA31 | 10 ppm (1.28 · 10$^{-5}$M) | 96.56 |
| | 2 ppm (2.56 · 10$^{-6}$M) | 96.17 |
| | 0.5 ppm (0.64 · 10$^{-6}$M) | 95.44 |
| | 0.3 ppm (0.38 · 10$^{-6}$M) | 93.00 |
| | 0.1 ppm (0.13 · 10$^{-6}$M) | 80.79 |
| SA32 | 10 ppm (1.23 · 10$^{-5}$M) | 95.58 |
| | 2 ppm (2.47 · 10$^{-6}$M) | 96.54 |
| | 0.5 ppm (0.62 · 10$^{-6}$M) | 96.30 |
| | 0.3 ppm (0.37 · 10$^{-6}$M) | 95.43 |
| | 0.1 ppm (0.12 · 10$^{-6}$M) | 79.01 |
| SA33 | 10 ppm (1.10 · 10$^{-5}$M) | 96.03 |
| | 2 ppm (2.22 · 10$^{-6}$M) | 96.25 |
| | 0.5 ppm (0.55 · 10$^{-6}$M) | 95.89 |
| | 0.3 ppm (0.33 · 10$^{-6}$M) | 95.37 |
| | 0.1 ppm (0.11 · 10$^{-6}$M) | 87.08 |
| SA34 | 10 ppm (1.07 · 10$^{-5}$M) | 95.69 |
| | 2 ppm (2.13 · 10$^{-6}$M) | 96.25 |
| | 0.5 ppm (0.53 · 10$^{-6}$M) | 92.23 |
| | 0.3 ppm (0.32 · 10$^{-6}$M) | 70.39 |
| | 0.1 ppm (0.11 · 10$^{-6}$M) | 52.40 |
| SA45 | 10 ppm (1.18 · 10$^{-5}$M) | 96.09 |
| | 2 ppm (2.23 · 10$^{-6}$M) | 95.23 |
| | 0.5 ppm (0.59 · 10$^{-6}$M) | 94.67 |
| | 0.3 ppm (0.35 · 10$^{-6}$M) | 93.01 |
| | 0.1 ppm (0.12 · 10$^{-6}$M) | 78.07 |
| SA46 | 10 ppm (1.14 · 10$^{-5}$M) | 94.96 |
| | 2 ppm (2.29 · 10$^{-6}$M) | 96.05 |
| | 0.5 ppm (0.57 · 10$^{-6}$M) | 94.51 |
| | 0.3 ppm (0.34 · 10$^{-6}$M) | 90.47 |
| | 0.1 ppm (0.11 · 10$^{-6}$M) | 82.23 |
| SA61 | 10 ppm (1.30 · 10$^{-5}$M) | 95.93 |
| | 2 ppm (2.61 · 10$^{-6}$M) | 95.55 |
| | 0.5 ppm (0.65 · 10$^{-6}$M) | 94.34 |
| | 0.3 ppm (0.39 · 10$^{-6}$M) | 91.92 |
| | 0.1 ppm (0.13 · 10$^{-6}$M) | 87.42 |
| SA63 | 10 ppm (1.50 · 10$^{-5}$M) | 96.95 |
| | 2 ppm (3.01 · 10$^{-6}$M) | 95.98 |
| | 0.5 ppm (0.75 · 10$^{-6}$M) | 95.82 |
| | 0.3 ppm (0.45 · 10$^{-6}$M) | 95.02 |
| | 0.1 ppm (0.15 · 10$^{-6}$M) | 90.68 |
| SA64 | 10 ppm (1.45 · 10$^{-5}$M) | 96.64 |
| | 2 ppm (2.89 · 10$^{-6}$M) | 96.37 |
| | 0.5 ppm (0.72 · 10$^{-6}$M) | 95.90 |
| | 0.3 ppm (0.43 · 10$^{-6}$M) | 94.18 |
| | 0.1 ppm (0.14 · 10$^{-6}$M) | 90.59 |
| SA66 | 10 ppm (1.05 · 10$^{-5}$M) | 96.48 |
| | 2 ppm (2.10 · 10$^{-6}$M) | 95.16 |
| | 0.5 ppm (0.52 · 10$^{-6}$M) | 90.41 |
| | 0.3 ppm (0.31 · 10$^{-6}$M) | 88.30 |
| | 0.1 ppm (0.10 · 10$^{-6}$M) | 85.79 |

The results show that all tested compounds exhibit an inhibition efficiency >89% at a concentration of 0.5 ppm (submicromolar concentration).

From the visual inspection of the mild steel specimens, it is clear that mild steel is severely corroded in the 1N HCl medium without a compound of the invention whereas the mild steel plate does not show any sign of corrosion in the presence of a compound of the invention. For example, FIG. 3 shows the difference in corrosion of the mild steel coupon with and without 1 ppm of AS171 after one week of immersion in the corrosive medium.

The linear relationships of Cinh/θ vs Cinh depicted in FIG. 4 suggest that the adsorption of AS174 from 1 N HCl solutions on the mild steel coupon obeyed the Langmuir adsorption isotherm. A strong correlation ($r^2 > 0.99$) for the Langmuir adsorption isotherm plots was found for all tested compounds of Table 3.

The invention claimed is:

1. Compound corresponding to the general formula (I):

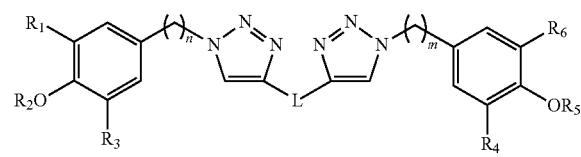

(I)

L is selected from an unsubstituted alkanediyl radical, —$(CR_aR_b)_p$—X—$(CR_aR_b)_q$— or an unsubstituted arylene directly branched with the triazole groups;

$R_1$, $R_3$, $R_4$ and $R_6$ are independently selected from H, Br, Cl, I and F;

$R_2$ and $R_5$ are independently selected from H or a substituted or unsubstituted alkyl;

X is selected from O, NR', S or S=O;

R', $R_a$ and $R_b$ are independently H or ($C_1$-$C_6$)alkyl;

n and m are independently 0, 1, 2, 3 or 4;

p and q are independently 1, 2 or 3;

and salts thereof;

with the proviso that said compound is not

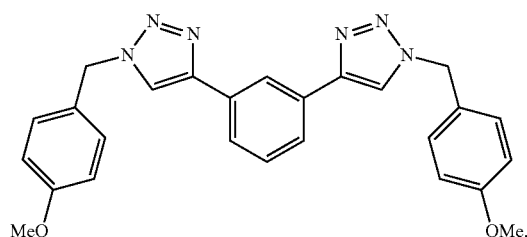 [SMILES: COc1ccc(Cn2cc(-c3cccc(-c4cn(Cc5ccc(OC)cc5)nn4)c3)nn2)cc1]

2. Compound of general formula (I) according to claim 1, wherein L is selected from an unsubstituted alkanediyl radical having 1 to 10 carbon atoms; —$(CH_2)_p$—O—$(CH_2)_q$—; —$(CH_2)_p$—NH—$(CH_2)_q$—; or an unsubstituted arylene directly branched with the triazole groups.

3. Compound of general formula (I) according to claim 1, wherein p and q are independently 1 or 2.

4. Compound of general formula (I) according to claim 1, wherein $R_1$, $R_3$, $R_4$ and $R_6$ are all H or are all Br; or wherein at least one of $R_1$ and $R_3$ is Br, Cl or I and at least one of $R_4$ and $R_6$ is Br, Cl or I.

5. Compound of general formula (I) according to claim 1, wherein $R_2$ and $R_5$ are independently selected from H, unsubstituted ($C_1$-$C_6$)alkyl, and ($C_1$-$C_6$)alkyl substituted by at least one group selected from amino, ($C_1$-$C_6$)alkylamino, (di($C_1$-$C_6$)alkyl)amino or an ammonium salt thereof.

6. Compound of general formula (I) according to claim 1, wherein n and m are independently 0, 1, 2 or 3.

7. Compound of general formula (I) according to claim 1, wherein:

$R_1$ and $R_6$ are identical;

$R_2$ and $R_5$ are identical;

$R_3$ and $R_4$ are identical; and n and m are identical.

8. Compound of general formula (I) according to claim 1, wherein:

L is selected from an unsubstituted alkanediyl radical having 3 to 6 carbon atoms, —$CH_2$—O—$CH_2$—, —$CH_2$—NH—$CH_2$, or an unsubstituted phenylene directly branched with the triazole groups;

$R_1$, $R_3$, $R_4$ and $R_6$ are independently selected from H, Br, Cl and I;

$R_2$ and $R_5$ are independently selected from H, unsubstituted ($C_1$-$C_6$)alkyl, and ($C_1$-$C_6$)alkyl substituted by a (di($C_1$-$C_6$)alkyl)amino group or an ammonium salt thereof;

n and m are 0, 1, 2 or 3.

9. Compound of general formula (I) according to claim 1, corresponding to one of the following formulae:

AS168

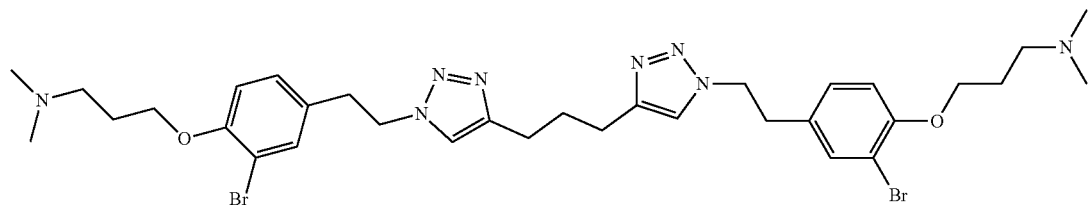

-continued
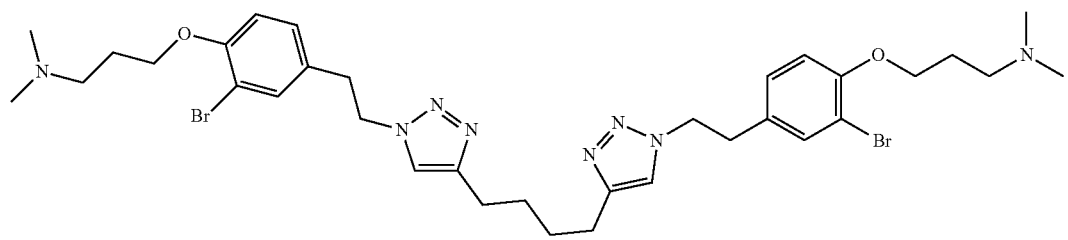
AS169
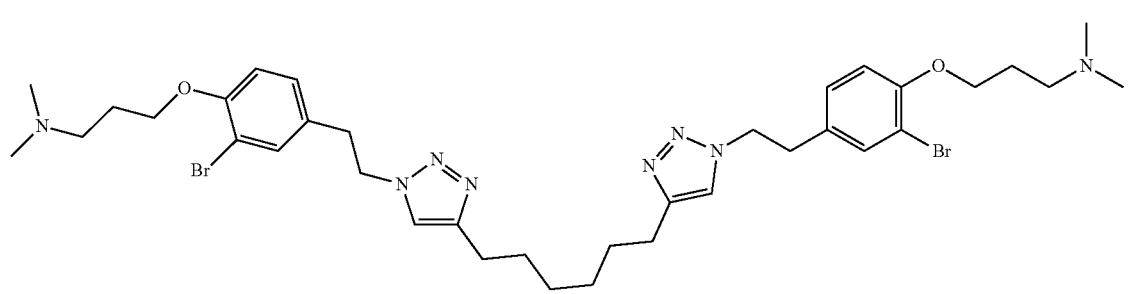
AS170
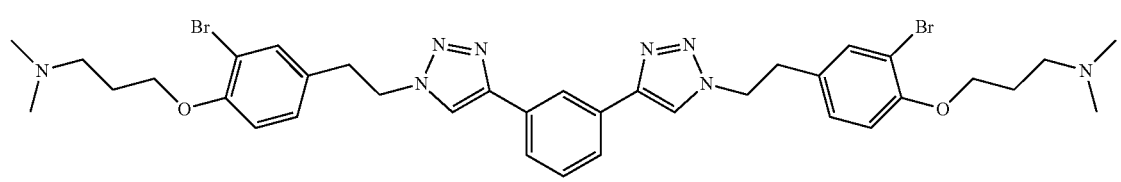
AS171
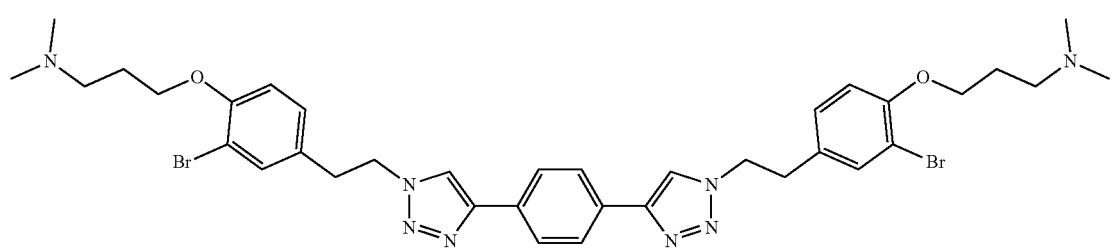
AS172
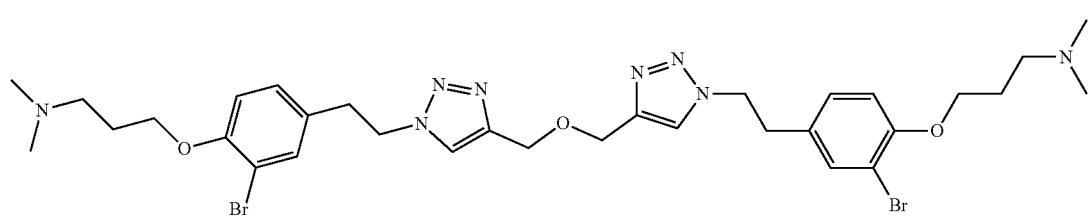
AS173
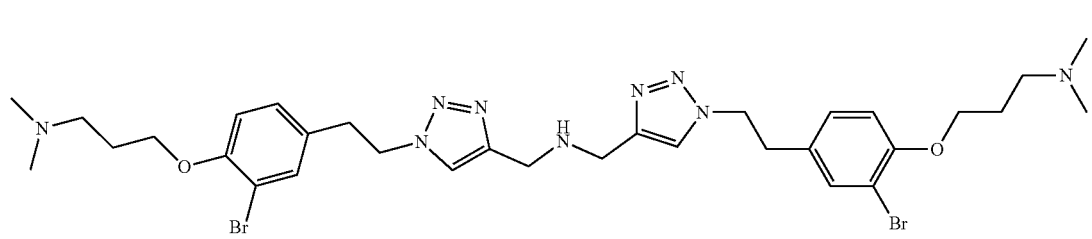
AS174
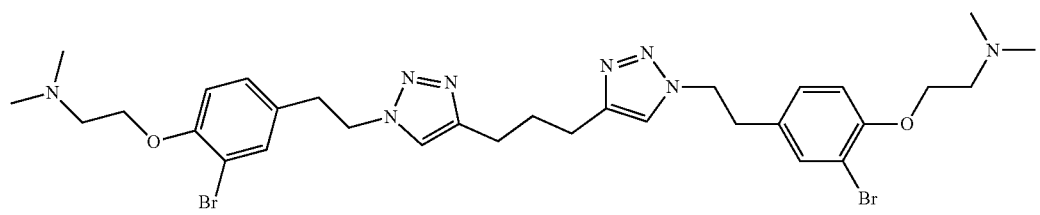
AS158

-continued
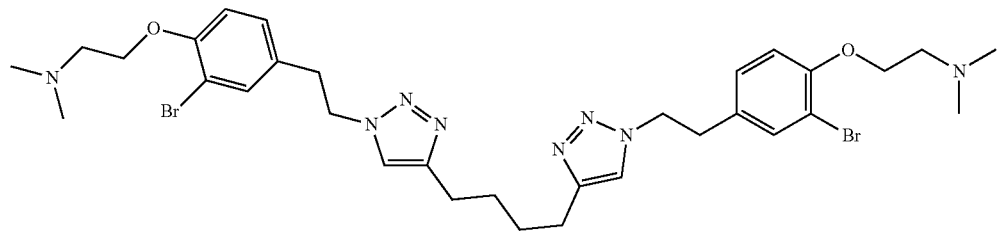
AS159
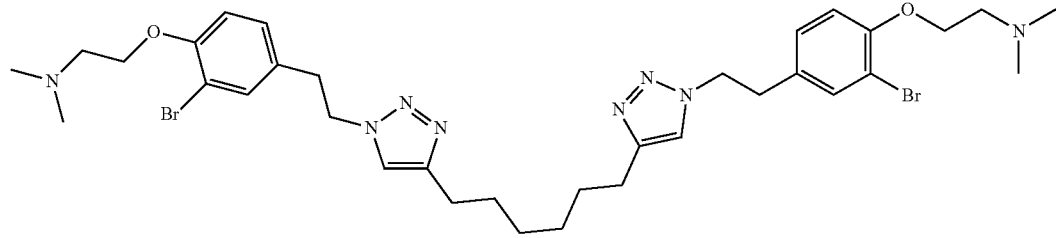
AS160
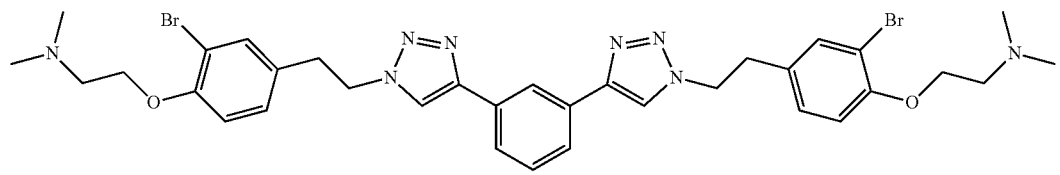
AS161
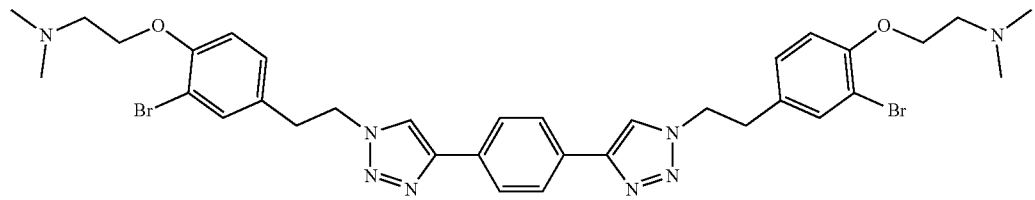
AS162
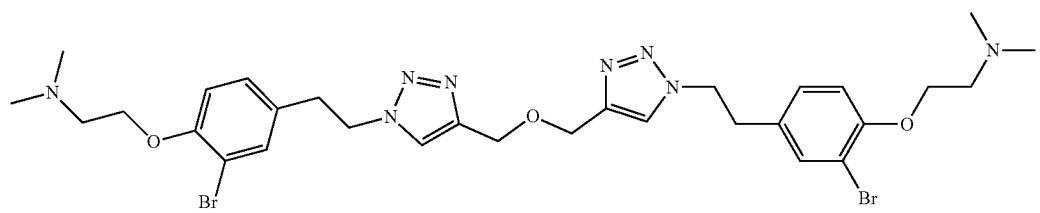
AS163
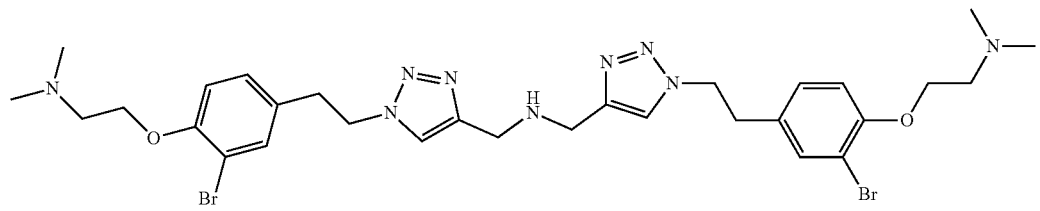
AS164
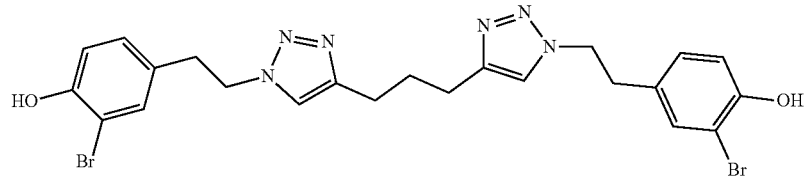
NT21

-continued
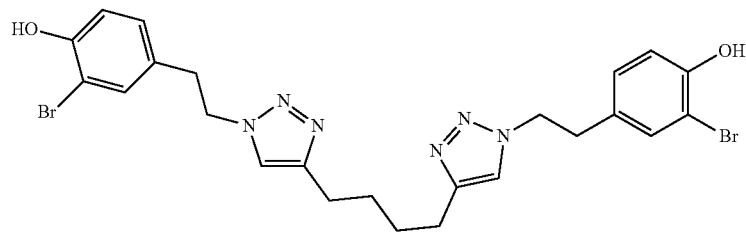
NT22
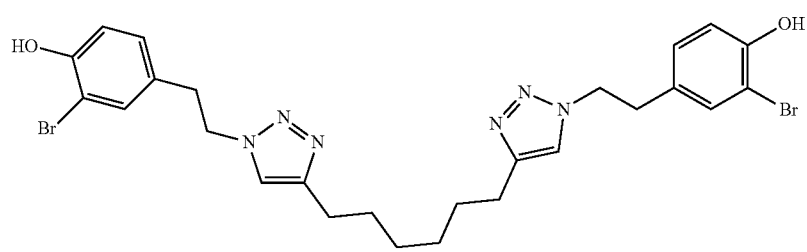
NT25
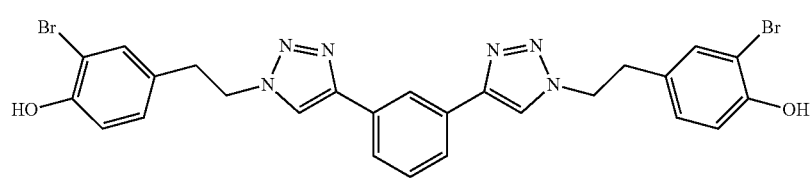
NT24
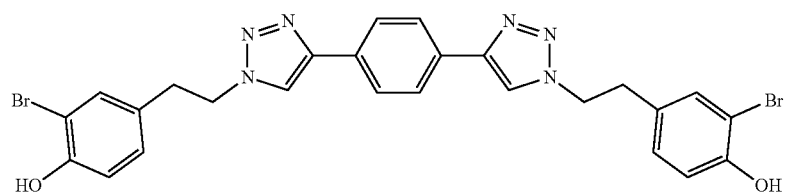
NT23
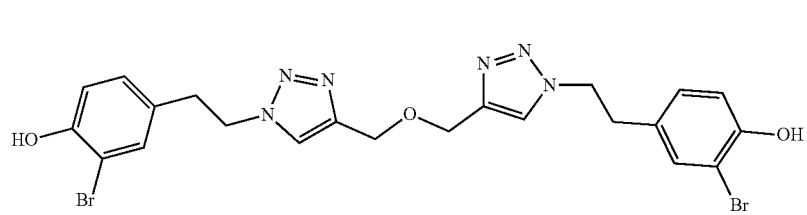
NT26
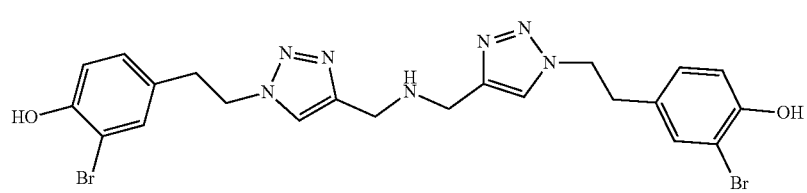
NT27
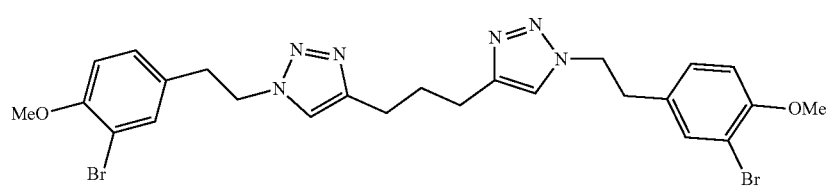
NT10

-continued
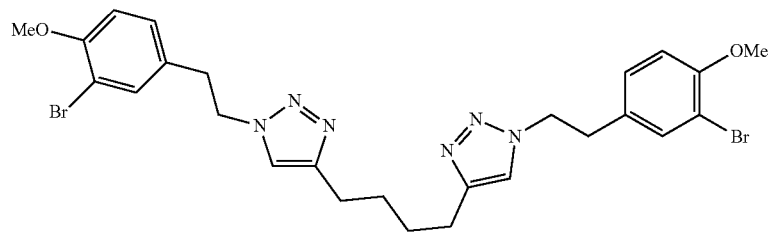
NT3
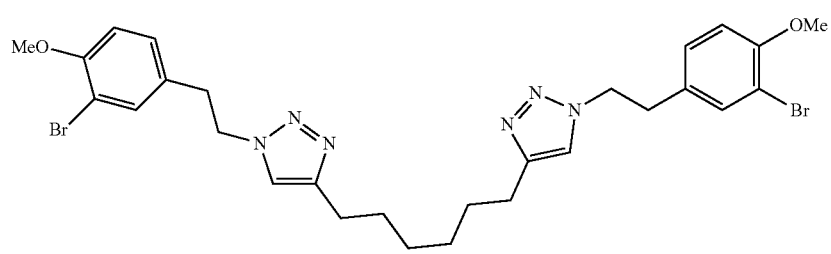
NT4
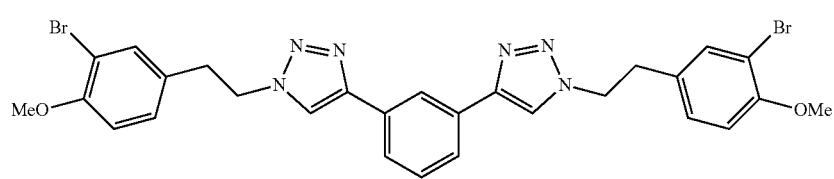
NT5
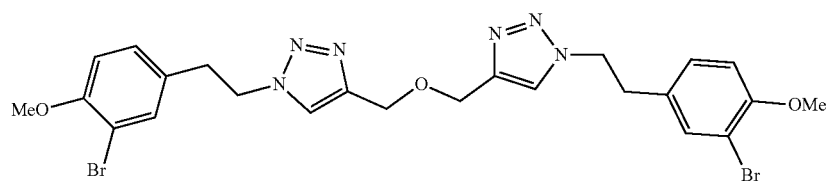
NT6
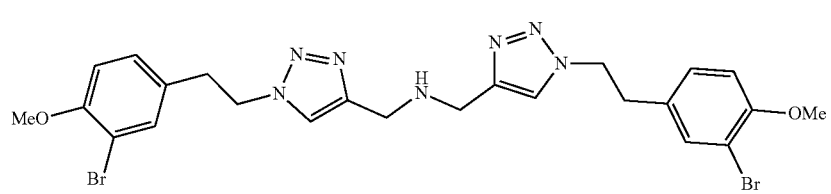
NT7
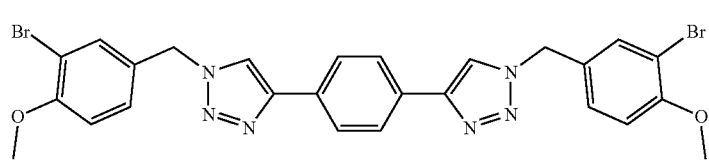
SA8
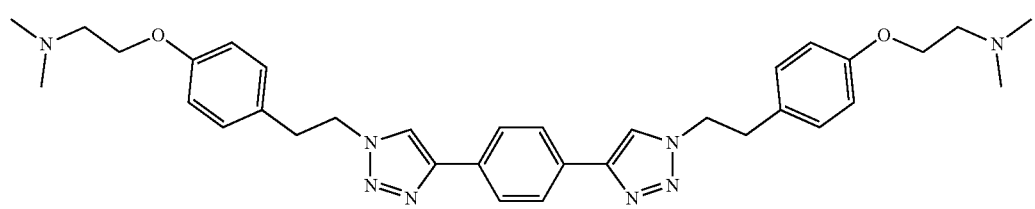
SA11

-continued
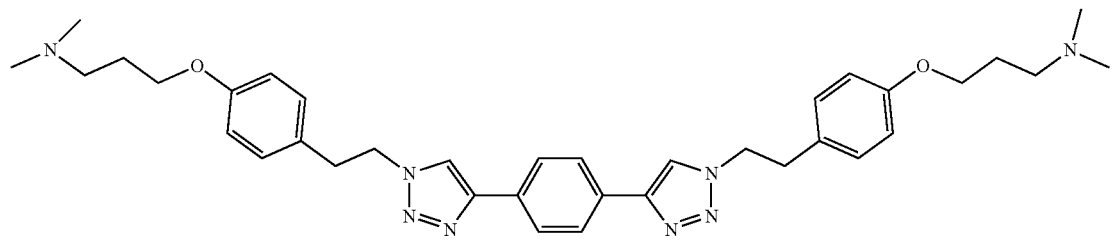
SA12
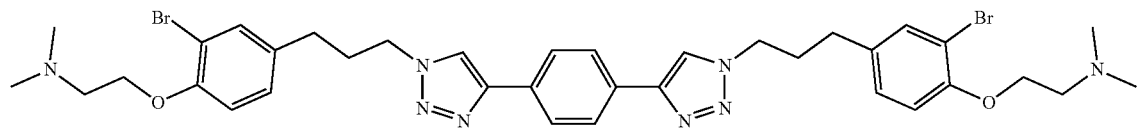
SA31
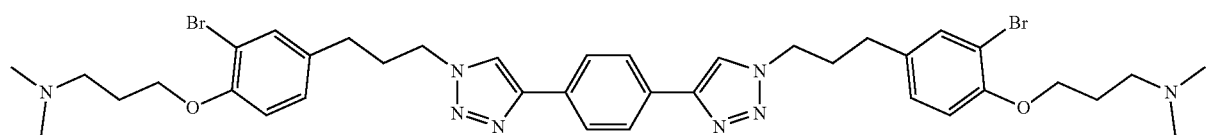
SA32
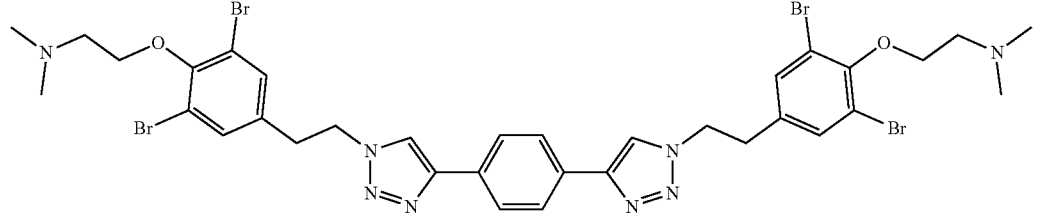
SA33
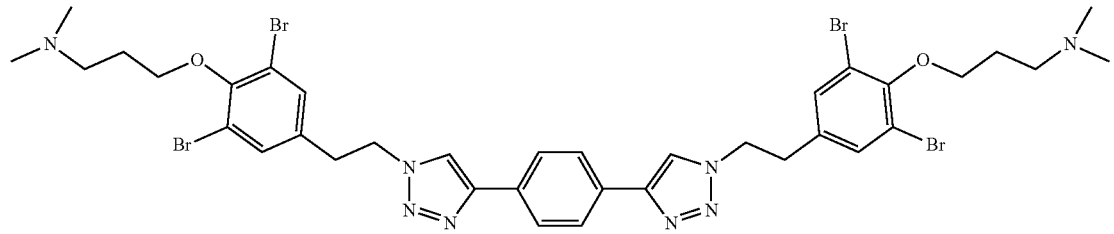
SA34
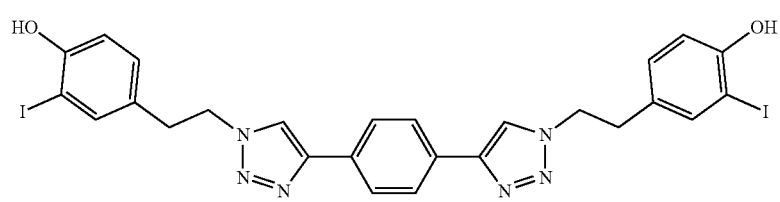
SA43
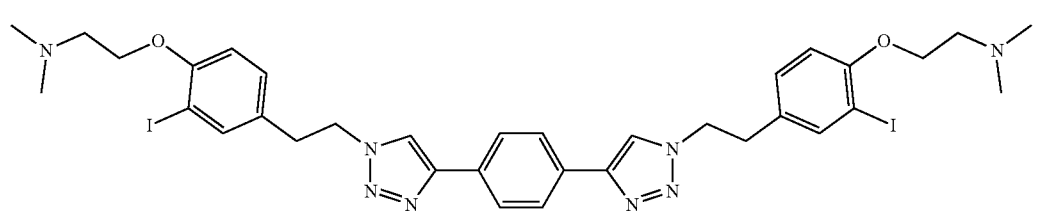
SA45

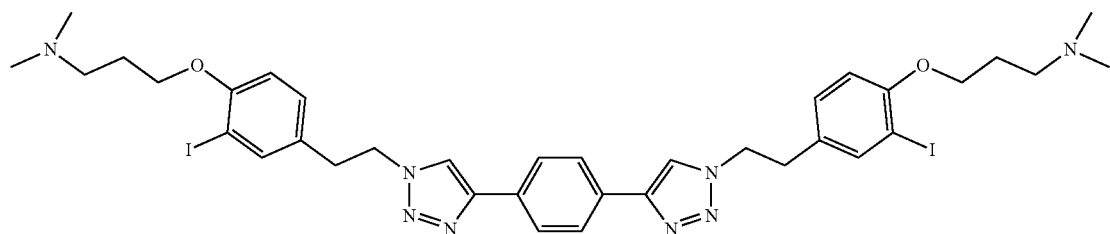

SA46

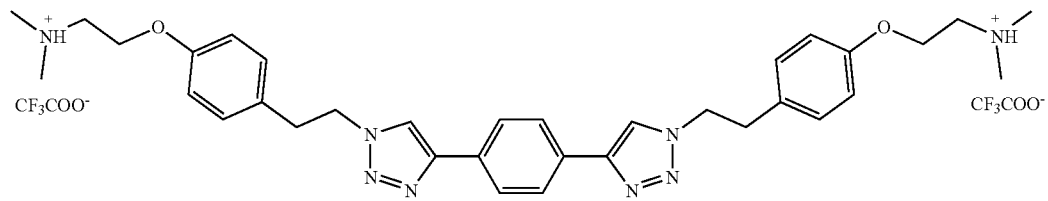

SA61

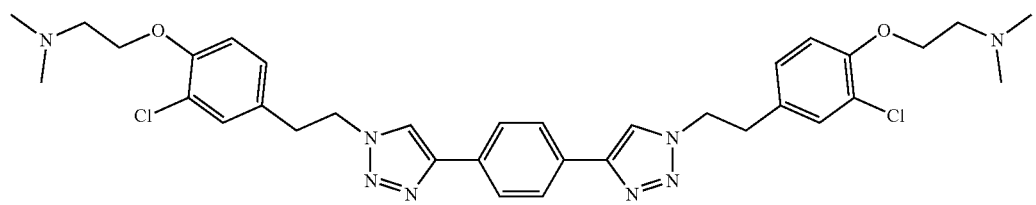

SA63

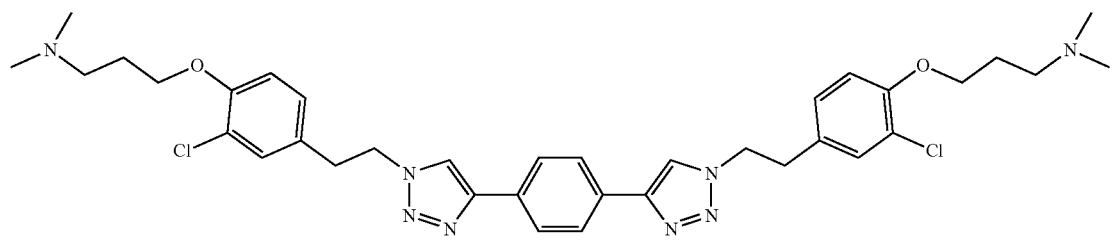

SA64

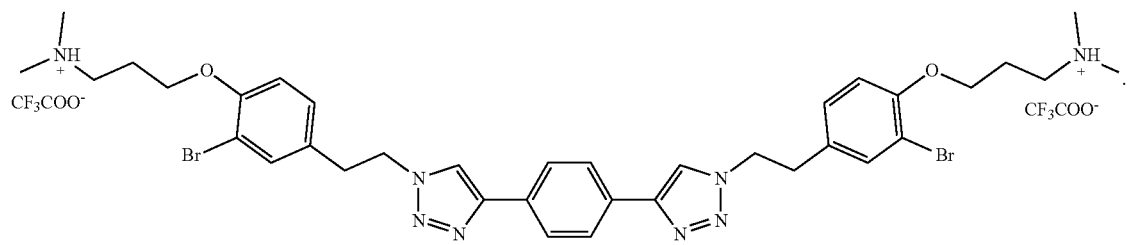

SA66

10. Composition comprising a compound of general formula (I) according to claim 1 and a carrier.

11. A method to prevent biofilm formation on a surface with a compound of general formula (I) according to claim 1, comprising contacting the surface with an effective amount of the compound.

12. A method to prevent corrosion of a surface with a compound of general formula (I) according to claim 1, comprising contacting the surface with an effective amount of the compound.

* * * * *